(12) United States Patent
Chew et al.

(10) Patent No.: US 11,560,592 B2
(45) Date of Patent: Jan. 24, 2023

(54) METHOD FOR RESETTING AN ARRAY

(71) Applicant: 10x Genomics, Inc., Pleasanton, CA (US)

(72) Inventors: Jennifer Chew, Pleasanton, CA (US); Zachary Bent, Pleasanton, CA (US); Alvaro J Gonzalez Lozano, Pleasanton, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 0 days.

(21) Appl. No.: 17/548,047

(22) Filed: Dec. 10, 2021

(65) Prior Publication Data

US 2022/0098661 A1     Mar. 31, 2022

Related U.S. Application Data

(63) Continuation of application No. PCT/US2021/034212, filed on May 26, 2021.

(60) Provisional application No. 63/041,481, filed on Jun. 19, 2020, provisional application No. 63/030,190, filed on May 26, 2020.

(51) Int. Cl.
*C12Q 1/68* (2018.01)
*C12Q 1/6874* (2018.01)
*C12Q 1/6825* (2018.01)

(52) U.S. Cl.
CPC ......... *C12Q 1/6874* (2013.01); *C12Q 1/6825* (2013.01)

(58) Field of Classification Search
USPC ......... 435/6.1, 6.11, 91.1, 183, 283.1, 287.1, 435/287.2; 436/94, 501; 536/23.1, 24.3, 536/24.33
See application file for complete search history.

(56) References Cited

U.S. PATENT DOCUMENTS

| | | |
|---|---|---|
| 4,683,195 A | 7/1987 | Mullis |
| 4,683,202 A | 7/1987 | Mullis |
| 4,800,159 A | 1/1989 | Mullis |
| 4,883,867 A | 11/1989 | Lee |
| 4,965,188 A | 10/1990 | Mullis |
| 4,988,617 A | 1/1991 | Landegren et al. |
| 5,002,882 A | 3/1991 | Lunnen |
| 5,130,238 A | 7/1992 | Malek |
| 5,308,751 A | 5/1994 | Ohkawa |
| 5,321,130 A | 6/1994 | Yue |
| 5,410,030 A | 4/1995 | Yue |
| 5,436,134 A | 7/1995 | Haugland |
| 5,455,166 A | 10/1995 | Walker |

(Continued)

FOREIGN PATENT DOCUMENTS

| | | |
|---|---|---|
| CN | 1680604 | 10/2005 |
| CN | 101221182 | 7/2008 |

(Continued)

OTHER PUBLICATIONS

Chapter 6: Alkaline Hydrolysis, pp. 1-12 from Carcass Disposal: A Comprehensive Review, published on Aug. 2004.*

(Continued)

*Primary Examiner* — Frank W Lu
(74) *Attorney, Agent, or Firm* — Fish & Richardson P.C.

(57) ABSTRACT

Provided herein are methods for resetting an array to which a biological sample has been applied that include treating the array with a set of biological sample removal conditions.

28 Claims, 36 Drawing Sheets

(56) References Cited

U.S. PATENT DOCUMENTS

| | | |
|---|---|---|
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,641,658 A | 6/1997 | Adams |
| 5,648,245 A | 7/1997 | Fire et al. |
| 5,658,751 A | 8/1997 | Yue |
| 5,750,341 A | 5/1998 | Macevicz |
| 5,763,175 A | 6/1998 | Brenner |
| 5,830,711 A | 11/1998 | Barany et al. |
| 5,837,832 A | 11/1998 | Chee et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,925,545 A | 7/1999 | Reznikoff et al. |
| 5,958,775 A | 9/1999 | Wickstrrom |
| 5,965,443 A | 10/1999 | Reznikoff et al. |
| 6,013,440 A | 1/2000 | Lipshutz |
| 6,027,889 A | 2/2000 | Barany et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,300,063 B1 | 10/2001 | Lipshutz et al. |
| 6,309,824 B1 | 10/2001 | Drmanac |
| 6,344,316 B1 | 2/2002 | Lockhart |
| 6,355,431 B1 | 3/2002 | Chee |
| 6,368,801 B1 | 4/2002 | Faruqi |
| 6,401,267 B1 | 6/2002 | Drmanac |
| 6,404,907 B1 | 6/2002 | Gilchrist |
| 6,432,360 B1 | 8/2002 | Church et al. |
| 6,503,713 B1 | 1/2003 | Rana |
| 6,506,561 B1 | 1/2003 | Cheval et al. |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,914,981 B2 | 3/2011 | Barany et al. |
| 7,955,794 B2 | 6/2011 | Shen et al. |
| 7,960,119 B2 | 6/2011 | Chee |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,288,103 B2 | 10/2012 | Oliphant |
| 8,383,338 B2 | 2/2013 | Kitzman |
| 8,460,865 B2 | 6/2013 | Chee |
| 8,481,257 B2 | 7/2013 | Van Eijk |
| 8,481,292 B2 | 7/2013 | Casbon |
| 8,481,698 B2 | 7/2013 | Lieberman et al. |
| 8,507,204 B2 | 8/2013 | Pierce et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 9,005,891 B2 | 4/2015 | Sinicropi et al. |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,598 B2 | 6/2016 | Chee |
| 9,376,716 B2 | 6/2016 | Van Eijk |

(56) References Cited

U.S. PATENT DOCUMENTS

| | | |
|---|---|---|
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,657,335 B2 | 5/2017 | Van Eijk |
| 9,670,542 B2 | 6/2017 | Van Eijk |
| 9,702,004 B2 | 7/2017 | Van Eijk |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,144,966 B2 | 12/2018 | Cantor |
| 10,208,982 B2 | 2/2019 | Bannish et al. |
| 10,273,541 B2 | 4/2019 | Hindson et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,550,429 B2 | 2/2020 | Harada et al. |
| 10,633,648 B2 | 4/2020 | Seelig et al. |
| 10,724,078 B2 | 7/2020 | Van Driel et al. |
| 10,774,372 B2 | 9/2020 | Chee et al. |
| 10,774,374 B2 | 9/2020 | Frisen et al. |
| 10,787,701 B2 | 9/2020 | Chee |
| 10,829,803 B2 | 11/2020 | Terbrueggen et al. |
| 10,913,975 B2 | 2/2021 | So et al. |
| 10,914,730 B2 | 2/2021 | Chee et al. |
| 10,927,403 B2 | 2/2021 | Chee et al. |
| 11,008,607 B2 | 5/2021 | Chee |
| 11,046,996 B1 | 6/2021 | Chee et al. |
| 11,067,567 B2 | 7/2021 | Chee |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |
| 11,390,912 B2 | 7/2022 | Frisen et al. |
| 11,401,545 B2 | 8/2022 | Chee |
| 2001/0055764 A1 | 12/2001 | Empendocles et al. |
| 2002/0040275 A1 | 4/2002 | Cravatt |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0224419 A1 | 12/2003 | Corcoran |
| 2003/0232348 A1 | 12/2003 | Jones et al. |
| 2003/0232382 A1 | 12/2003 | Brennan |
| 2004/0033499 A1 | 2/2004 | Ilsley et al. |
| 2004/0067492 A1 | 4/2004 | Peng et al. |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 | 11/2004 | Reznikoff et al. |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0260653 A1 | 11/2005 | LaBaer |
| 2005/0266417 A1 | 12/2005 | Barany et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |

(56) References Cited

U.S. PATENT DOCUMENTS

| | | |
|---|---|---|
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0233802 A1 | 9/2009 | Bignell et al. |
| 2009/0253581 A1 | 10/2009 | van Eijk et al. |
| 2009/0283407 A1 | 11/2009 | Van Eijk |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0069263 A1 | 3/2010 | Shendure et al. |
| 2010/0105052 A1 | 4/2010 | Drmanac et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0111409 A1 | 5/2011 | Sinicropi et al. |
| 2011/0152111 A1 | 6/2011 | Illumina |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0252702 A1 | 10/2012 | Muratani et al. |
| 2012/0258871 A1 | 10/2012 | Kozlov et al. |
| 2012/0289414 A1 | 11/2012 | Mitra et al. |
| 2013/0005594 A1 | 1/2013 | Terbrueggen et al. |
| 2013/0005600 A1 | 1/2013 | Olek |
| 2013/0035239 A1 | 2/2013 | Kong et al. |
| 2013/0079232 A1 | 3/2013 | Kain et al. |
| 2013/0171621 A1 | 7/2013 | Luo et al. |
| 2013/0244884 A1 | 9/2013 | Jacobson et al. |
| 2013/0261019 A1 | 10/2013 | Lin et al. |
| 2013/0338042 A1 | 12/2013 | Shen et al. |
| 2014/0066318 A1 | 3/2014 | Frisen et al. |
| 2014/0121118 A1 | 5/2014 | Warner |
| 2014/0274731 A1 | 9/2014 | Raymond et al. |
| 2014/0323330 A1 | 10/2014 | Glezer et al. |
| 2014/0342921 A1 | 11/2014 | Weiner |
| 2015/0000854 A1 | 1/2015 | Gann-Fetter et al. |
| 2016/0019337 A1 | 1/2016 | Roberts et al. |
| 2016/0024576 A1 | 1/2016 | Chee |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0333403 A1 | 11/2016 | Chee |
| 2017/0016053 A1 | 1/2017 | Beechem et al. |
| 2017/0029875 A1 | 2/2017 | Zhang et al. |
| 2017/0058339 A1 | 3/2017 | Chee |
| 2017/0058340 A1 | 3/2017 | Chee |
| 2017/0058345 A1 | 3/2017 | Chee |
| 2017/0067096 A1 | 3/2017 | Wassie et al. |
| 2017/0088881 A1 | 3/2017 | Chee |
| 2017/0089811 A1 | 3/2017 | Tillberg et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0241911 A1 | 8/2017 | Rockel et al. |
| 2017/0335410 A1 | 11/2017 | Driscoll et al. |
| 2017/0349940 A1 | 12/2017 | Morin et al. |
| 2018/0051322 A1 | 2/2018 | Church et al. |
| 2018/0057873 A1 | 3/2018 | Zhou et al. |
| 2018/0094316 A1 | 4/2018 | Oliphant et al. |
| 2018/0112261 A1 | 4/2018 | Van Driel et al. |
| 2018/0163265 A1 | 6/2018 | Zhang et al. |
| 2018/0179591 A1 | 6/2018 | van Eijk |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2019/0055594 A1 | 2/2019 | Samusik et al. |
| 2019/0085383 A1 | 3/2019 | Church et al. |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0194709 A1 | 6/2019 | Church et al. |
| 2019/0203275 A1 | 7/2019 | Frisen et al. |
| 2019/0218276 A1 | 7/2019 | Regev et al. |
| 2019/0233880 A1 | 8/2019 | Mir |
| 2019/0262831 A1 | 8/2019 | West et al. |
| 2019/0264268 A1 | 8/2019 | Frisen et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0330617 A1 | 10/2019 | Church et al. |
| 2019/0360043 A1 | 11/2019 | Pham et al. |
| 2019/0367969 A1 | 12/2019 | Belhocine et al. |
| 2020/0010891 A1 | 1/2020 | Beechem et al. |
| 2020/0024641 A1 | 1/2020 | Nolan et al. |
| 2020/0048690 A1 | 2/2020 | Chee |
| 2020/0063195 A1 | 2/2020 | Chee |
| 2020/0063196 A1 | 2/2020 | Chee |
| 2020/0080136 A1 | 3/2020 | Zhang et al. |
| 2020/0109443 A1 | 4/2020 | Chee |
| 2020/0199565 A1 | 6/2020 | Chen et al. |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0239946 A1 | 7/2020 | Dewal |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0095331 A1 | 4/2021 | Fan et al. |
| 2021/0123040 A1 | 4/2021 | Macosko et al. |
| 2021/0140982 A1 | 5/2021 | Uytingco et al. |
| 2021/0150707 A1 | 5/2021 | Weisenfeld et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0198741 A1 | 7/2021 | Williams |
| 2021/0199660 A1 | 7/2021 | Williams et al. |

(56) References Cited

U.S. PATENT DOCUMENTS

| | | |
|---|---|---|
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0106632 A1 | 4/2022 | Galonska et al. |
| 2022/0106633 A1 | 4/2022 | Engblom et al. |
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0241780 A1 | 8/2022 | Tentori et al. |

FOREIGN PATENT DOCUMENTS

| | | |
|---|---|---|
| CN | 108949924 | 12/2018 |
| EP | 1782737 | 5/2007 |
| EP | 1910562 | 4/2008 |
| EP | 1923471 | 5/2008 |
| EP | 2002017 | 12/2008 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/17390 | 3/2000 |
| WO | WO 2001/06012 | 1/2001 |
| WO | WO 2001/009363 | 2/2001 |
| WO | WO 2001/042796 | 6/2001 |
| WO | WO 2001/090415 | 11/2001 |
| WO | WO 2001/096608 | 12/2001 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 11/2003 |
| WO | WO 2004/015080 | 2/2004 |
| WO | WO 2004/067759 | 8/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2009/032167 | 3/2009 |
| WO | WO 2009/152928 | 12/2009 |
| WO | WO 2010/019826 | 2/2010 |
| WO | WO 2010/027870 | 3/2010 |
| WO | WO 2010/126614 | 11/2010 |
| WO | WO 2011/008502 | 1/2011 |
| WO | WO 2011/062933 | 5/2011 |
| WO | WO 2011/068088 | 6/2011 |
| WO | WO 2012/049316 | 4/2012 |
| WO | WO 2012/071428 | 5/2012 |
| WO | WO 2012/129242 | 9/2012 |
| WO | WO 2012/159089 | 11/2012 |
| WO | WO 2013/123442 | 8/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/144713 | 9/2014 |
| WO | WO 2014/152397 | 9/2014 |
| WO | WO 2014/210223 | 12/2014 |
| WO | WO 2014/210225 | 12/2014 |
| WO | WO 2015/161173 | 10/2015 |
| WO | WO 2016/138496 | 9/2016 |
| WO | WO 2016/138500 | 9/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/075293 | 5/2017 |
| WO | WO 2017/096158 | 7/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/045181 | 3/2018 |
| WO | WO 2018/064640 | 4/2018 |
| WO | WO 2018/085599 | 5/2018 |
| WO | WO 2018/091676 | 5/2018 |
| WO | WO 2018/136856 | 7/2018 |
| WO | WO 2018/144582 | 8/2018 |
| WO | WO 2018/209398 | 11/2018 |

(56) References Cited

FOREIGN PATENT DOCUMENTS

| WO | WO 2019/023214 | 1/2019 |
|---|---|---|
| WO | WO 2019/032760 | 2/2019 |
| WO | WO 2019/068880 | 4/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/053655 | 3/2020 |
| WO | WO 2020/056381 | 3/2020 |
| WO | WO 2020/061064 | 3/2020 |
| WO | WO 2020/061066 | 3/2020 |
| WO | WO 2020/061108 | 3/2020 |
| WO | WO 2020/076979 | 4/2020 |
| WO | WO 2020/112604 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/176788 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/243579 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/119320 | 6/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/087273 | 4/2022 |
| WO | WO 2022/099037 | 5/2022 |
| WO | WO 2022/109181 | 5/2022 |
| WO | WO 2022/140028 | 6/2022 |
| WO | WO 2022/147005 | 7/2022 |
| WO | WO 2022/147296 | 7/2022 |

OTHER PUBLICATIONS

The definition of "plant fiber". Printed on Apr. 8, 2022.*
"What pH Levels Are Considered Strong & Weak?" Printed on Aug. 5, 2022.*
U.S. Appl. No. 60/416,118, filed Oct. 3, 2002, Fan et al.
U.S. Appl. No. 61/267,363, filed Dec. 7, 2009, Fan et al.
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpdlbFVhalpexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwdl9It/e54d99fb08a8fl500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
Adiconis et al., "Comparative analysis of RNA sequencing methods for degraded or low-input samples," Nat Methods, Jul. 2013, 10(7):623-9.
Alam, "Proximity Ligation Assay (PLA)," Curr Protoc Immunol., Nov. 2018, 123(1):e58, 8 pages.
Andresen et al., "Helicase-dependent amplification: use in OnChip amplification and potential for point-of-care diagnostics," Expert Rev Mol Diagn., Oct. 2009, 9(7):645-650.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Blanco et al., "A practical approach to FRET-based PNA fluorescence in situ hybridization," Methods, Dec. 2010, 52(4):343-51.
Bullard et al., "Direct comparison of nick-joining activity of the nucleic acid ligases from bacteriophage T4," Biochem, J. 2006, 398(1):135-144.
Burton et al., "Coverslip Mounted-Immersion Cycled in Situ RT-PCR for the Localization of mRNA in Tissue Sections," Biotechniques, 1998, 24(1):92-100.
Chen et al., "DNA hybridization detection in a microfluidic Channel using two fluorescently labelled nucleic acid probes," Biosensors and Bioelectronics, 2008, 23(12):1878-1882.
Chen et al., "Expansion microscopy," Science, 2015, 347(6221):543-548.
Chen et al., "Nanoscale imaging of RNA with expansion microscopy," Nat Methods, Aug. 2016, 13(8):679-84.
Chen et al., "RNA imaging. Spatially resolved, highly multiplexed RNA profiling in single cells," Science, Apr. 2015, 348(6233):aaa6090, 21 pages.
Chen et al., "Spatially resolved, highly multiplexed RNA profiling in single cells," Science, 2015, 348(6233):aaa6090, 21 pages.
Chrisey et al., "Covalent attachment of synthetic DNA to self-assembled monolayer films," Nucleic Acids Res., Aug. 1996, 24(15):3031-9.
Corces et al., "An improved ATAC-seq protocol reduces background and enables interrogation of frozen tissues," Nat. Methods, 2017, 14(10):959-962.
Credle et al., "Multiplexed analysis of fixed tissue RNA using Ligation in situ Hybridization," Nucleic Acids Research, 2017, 45(14):e128, 9 pages.

(56) References Cited

OTHER PUBLICATIONS

Cujec et al., "Selection of v-abl tyrosine kinase substrate sequences from randomized peptide and cellular proteomic libraries using mRNA display," Chemistry and Biology, 2002, 9(2):253-264.
Dahl et al., "Circle-to-circle amplification for precise and sensitive DNA analysis," Proc. Natl. Acad. Sci., 2004, 101(13):4548-4553.
Darmanis et al., "ProteinSeq: High-Performance Proteomic Analyses by Proximity, Ligation and Next Generation Sequencing," PLos One, 2011, 6(9):e25583, 10 pages.
Deamer et al., "Characterization of nucleic acids by nanopore analysis," Acc Chem Res., Oct. 2002, 35(10):817-25.
Deng et al., "Spatial Epigenome Sequencing at Tissue Scale and Cellular Level," BioRxiv, Mar. 2021, 40 pages.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Eberwine, "Amplification of mRNA populations using aRNA generated from immobilized oligo(dT)-T7 primed cDNA," BioTechniques, 1996, 20(4):584-91.
Eldridge et al., "An in vitro selection strategy for conferring protease resistance to ligand binding peptides," Protein Eng Des Sel., 2009, 22(11):691-698.
Eng et al., "Profiling the transcriptome with RNA SPOTs," Nat Methods., 2017, 14(12):1153-1155.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
Fluidigm, "Equivalence of Imaging Mass Cytometry and Immunofluorescence on FFPE Tissue Sections," White Paper, 2017, 12 pages.
Forster et al., "A human gut bacterial genome and culture collection for improved metagenomic analyses," Nature Biotechnology, 2019, 37(2):186-192.
Fu et al., "Repeat subtraction-mediated sequence capture from a complex genome," Plant J., Jun. 2010, 62(5):898-909.
Fullwood et al., "Next-generation DNA sequencing of paired-end tags (PET) for transcriptome and genome analyses," Genome Res., 2009, 19(4):521-532.
Gao et al., "Q&A: Expansion microscopy", BMC Biology, 15:50, 9 pages, 2017.
Gill et al., "Nucleic acid isothermal amplification technologies: a review," Nucleosides Nucleotides Nucleic Acids, Mar. 2008, 27(3):224-43.
Glass et al., "SIMPLE: a sequential immunoperoxidase labeling and erasing method," J. Histochem. Cytochem., Oct. 2009, 57(10):899-905.
Gloor, "Gene targeting in Drosophila," Methods Mol Biol., 2004, 260:97-114.
Goryshin et al., "Tn5 in vitro transposition," J Biol Chem., Mar. 1998, 273(13):7367-74.
Grokhovsky, "Specificity of DNA cleavage by ultrasound," Molecular Biology, 2006, 40(2):276-283.
Gu et al., "Protein tag-mediated conjugation of oligonucleotides to recombinant affinity binders for proximity ligation," N Biotechnol., 2013, 30(2):144-152.
Gupta et al., "Single-cell isoform RNA sequencing characterizes isoforms in thousands of cerebellar cells," Nature Biotechnol., Oct. 2018, 36:1197-1202.
Hahnke et al., "Striptease on glass: validation of an improved stripping procedure for in situ microarrays," J Biotechnol., Jan. 2007, 128(1):1-13.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Hu et al., "High reproducibility using sodium hydroxide-stripped long oligonucleotide DNA microarrays," Biotechniques, Jan. 2005, 38(1):121-4.
Hycultbiotech.com, [online], "Immunohistochemistry, Paraffin" Apr. 2010, retrieved on Apr. 16, 2020, retrieved from URL<https://hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Kennedy-Darling et al., "Measuring the Formaldehyde Protein-DNA Cross-Link Reversal Rate," Analytical Chemistiy, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS One, 2012, 7(6):e37441, 10 pages.
Kozlov et al., "A method for rapid protease substrate evaluation and optimization," Comb Chem High Throughput Screen, 2006, 9(6):481-87.
Lage et al., "Whole genome analysis of genetic alterations in small DNA samples using hyperbranched strand displacement amplification and array-CGH," Genome Research, 2003, 13(2):294-307.
Lampe et al., "A purified mariner transposase is sufficient to mediate transposition in vitro," EMBO J., Oct. 1996, 15(19):5470-9.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.

(56) References Cited

OTHER PUBLICATIONS

Lee et al., "Improving the efficiency of genomic loci capture using oligonucleotide arrays for high throughput resequencing," BMC Genomics, Dec. 2009, 10:646, 12 pages.

Li et al., "A photocleavable fluorescent nucleotide for DNA sequencing and analysis," Proc. Natl. Acad. Sci., 2003, 100(2):414-419.

Li et al., "An activity-dependent proximity ligation platform for spatially resolved quantification of active enzymes in single cells," Nat Commun, Nov. 2017, 8(1):1775, 12 pages.

Li et al., "RASL-seq for Massively Parallel and Quantitative Analysis of Gene Expression," Curr Protoc Mol Biol., Apr. 2012, 4(13):1-10.

Li et al., "Review: a comprehensive summary of a decade development of the recombinase polymerase amplification," Analyst, Dec. 2018, 144(1):31-67.

Lin et al., "Highly multiplexed imaging of single cells using a high-throughput cyclic immunofluorescence method," Nat Commun., Sep. 2015, 6:8390, 7 pages.

Lovatt et al., "Transcriptome in vivo analysis (TIVA) of spatially defined single cells in live tissue," Nature Methods, 2013, 11(2):190-196.

Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.

Lundberg et al., "High-fidelity amplification using a thermostable DNA polymerase isolated from Pyrococcus furiosus," Gene, 1991, 108(1):1-6.

Lundberg et al., "Homogeneous antibody-based proximity extension assays provide sensitive and specific detection of low-abundant proteins in human blood," Nucleic Acids Res., 2011, 39(15):e102, 8 pages.

Lundin et al., "Increased throughput by parallelization of library preparation for massive sequencing," PLoS One, Apr. 2010, 5(4):e10029, 7 pages.

Lyck et al., "Immunohistochemical markers for quantitative studies of neurons and glia in human neocortex," J Histochem Cytochem, 2008, 56(3):201-21.

MacIntyre, "Unmasking antigens for immunohistochemistry.," Br J Biomed Sci., 2001, 58(3):190-6.

McCloskey et al., "Encoding PCR products with batch-stamps and barcodes," Biochem. Genet., 2007, 45(11-12):761-767.

Meers et al., "Improved CUT&RUN chromatin profiling tools," Elife, Jun. 2019, 8:e46314, 16 pages.

Miele et al., "Mapping cis- and trans-chromatin interaction networks using chromosome conformation capture (3C)," Methods Mol Biol., 2009, 464:105-21.

Morlan et al., "Selective depletion of rRNA enables whole transcriptome profiling of archival fixed tissue," PLoS One, Aug. 2012, 7(8):e42882, 8 pages.

Motea et al., "Terminal deoxynucleotidyl transferase: the story of a misguided DNA polymerase," Biochim Biophys Acta., May 2010, 1804(5):1151-66.

Nandakumar et al., "How an RNA Ligase Discriminates RNA versus DNA Damage," Molecular Cell, 2004, 16:211-221.

Ncbi.nlm.nih.gov, [online], "Molecular Inversion Probe Assay," available on or before Oct. 14, 2014, via Internet Archive: Wayback Machine URL<https://web.archive.org/web/20141014124037/https://ncbi.nlm.nih.gov/probe/docs/techmip/>, retrieved on Jun. 16, 2021, retrieved from URL<https://ncbi.nlm.nih.gov/probe/docs/techmip/>, 2 pages.

Ng et al., "Gene identification signature (GIS) analysis for transcriptome characterization and genome annotation," Nature Methods, 2005, 2(2):105-111.

Nichols et al., "RNA Ligases," Curr Protoc Mol Biol., Oct. 2008, 84(1):3.15.1-3.15.4.

Niklas et al., "Selective permeabilization for the high-throughput measurement of compartmented enzyme activities in mammalian cells," Anal Biochem, Sep. 2011, 416(2):218-27.

Ohtsubo et al., "Bacterial insertion sequences," Curr Top Microbiol Immunol., 1996, 204:1-26.

Pandey et al., "Inhibition of terminal deoxynucleotidyl transferase by adenine dinucleotides. Unique inhibitory action of Ap5A," FEBS Lett., Mar. 1987, 213(1):204-8.

Park et al., "Single cell trapping in larger micro wells capable of supporting cell spreading and proliferation," Microfluid Nanofluid, 2010, 8:263-268.

PCT International Search Report and Written Opinion in International Appln. No. PCT/US2021/034212, dated Sep. 16, 2021, 16 pages.

Pellestor et al., "The peptide nucleic acids (PNAs), powerful tools for molecular genetics and cytogenetics," Eur J Hum Genet., Sep. 2004, 12(9):694-700.

Picelli et al., "Tn5 transposase and tagmentation procedures for massively scaled sequencing projects," Genome Res., Dec. 2014, 24(12):2033-40.

Pipenburg et al., "DNA detection using recombination proteins," PLoS Biol., Jul. 2006, 4(7):e204, 7 pages.

Plasterk, "The Tc1/mariner transposon family," Curr Top Microbiol Immunol., 1996, 204:125-43.

Plongthongkum et al., "Advances in the profiling of DNA modifications: cytosine methylation and beyond," Nature Reviews Genetics, Aug. 2014, 15(10):647-661.

U.S. Appl. No. 61/267,363, filed Dec. 7, 2009, 33 pages.

Raab et al., "Human tRNA genes function as chromatin insulators," EMBO J., Jan. 2012, 31(2):330-50.

Reznikoff, "Tn5 as a model for understanding DNA transposition," Mol Microbiol., Mar. 2003, 47(5):1199-206.

Ristic et al., "Detection of Protein-Protein Interactions and Post-translational Modifications Using the Proximity Ligation Assay: Application to the Study of the SUMO Pathway," Methods Mol. Biol., 2016, 1449:279-90.

Rodriques et al., "Slide-seq: A scalable technology for measuring genome-wide expression at high spatial resolution," Science, 2019, 363(6434):1463-1467.

Roy et al., "Assessing long-distance RNA sequence connectivity via RNA-templated DNA-DNA ligation," eLife, 2015, 4:e03700, 21 pages.

Schweitzer et al., "Multiplexed protein profiling on microarrays by rolling-circle amplification," Nature Biotechnology, Apr. 2002, 20(4):359-365.

Shelbourne et al., "Fast copper-free click DNA ligation by the ring-strain promoted alkyne-azide cycloaddition reaction," Chem. Commun., 2011, 47(22):6257-6259.

Shendure et al., "Accurate multiplex polony sequencing of an evolved bacterial genome," Science, 2005, 309(5741):1728-1732.

Simonis et al., "Nuclear organization of active and inactive chromatin domains uncovered by chromosome conformation capture-on-chip (4C)," Nat Genet., Nov. 2006, 38(11):1348-54.

Skene et al., "An efficient targeted nuclease strategy for high-resolution mapping of DNA binding sites," Elife, Jan. 2017, 6:e21856, 35 pages.

Spitale et al., "Structural imprints in vivo decode RNA regulatory mechanisms," Nature, 2015, 519(7544):486-90.

Stoddart et al., "Single-nucleotide discrimination in immobilized DNA oligonucleotides with a biological nanopore," PNAS USA., May 2009, 106(19):7702-7707.

Stroh et al., "Quantum dots spectrally distinguish multiple species within the tumor milieu in vivo," Nat Med., Jun. 2005, 11(6):678-82.

Taylor et al., "Mitochondrial DNA mutations in human disease," Nature Reviews Genetics, May 2005, 6(5):389-402.

Tentori et al., "Detection of Isoforms Differing by a Single Charge Unit in Individual Cells," Chem. Int. Ed., 2016, 55(40):12431-5.

Tian et al., "Antigen peptide-based immunosensors for rapid detection of antibodies and antigens," Anal Chem, 2009, 81(13):5218-5225.

Tolbert et al., "New methods for proteomic research: preparation of proteins with N-terminal cysteines for labeling and conjugation," Angewandte Chemie International Edition, Jun. 2002, 41(12):2171-4.

(56) References Cited

OTHER PUBLICATIONS

Trejo et al., "Extraction-free whole transcriptome gene expression analysis of FFPE sections and histology-directed subareas of tissue," PLoS One, Feb. 2019, 14(2):e0212031, 22 pages.
U.S. Appl. No. 60/416,118 Fan et al., Multiplex Nucleic Acid Analysis Using Archived or Fixed Samples, filed Oct. 3, 2002, 22 pages.
Vandernoot et al., "cDNA normalization by hydroxyapatite chromatography to enrich transcriptome diversity in RNA-seq applications," Biotechniques, Dec. 2012, 53(6):373-80.
Velculescu et al., "Serial analysis of gene expression," Science, Oct. 1995, 270(5235):484-7.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Waichman et al., "Functional immobilization and patterning of proteins by an enzymatic transfer reaction," Analytical chemistry, 2010, 82(4):1478-85.
Wang et al., "Concentration gradient generation methods based on microfluidic systems," RSC Adv., 2017, 7:29966-29984.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Wu et al., "Detection DNA Point Mutation with Rolling-Circle Amplification Chip," IEEE, 2010 4th International Conference on Bioinformatics and Biomedical Engineering, Jun. 2010, 4 pages.
Yeakley et al., "Profiling alternative splicing on fiber-optic arrays," Nature biotechnology, 2002, 20:353-358.
Yeakley et al., "A trichostatin A expression signature identified by TempO-Seq targeted whole transcriptome profiling," PLoS One, May 2017, 12(5):e0178302, 22 pages.
Yin et al., "Genetically encoded short peptide tag for versatile protein labeling by Sfp phosphopantetheinyl transferase," PNAS, 2005, 102(44):15815-20.
Zhang et al., "Archaeal RNA ligase from thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Multiplex ligation-dependent probe amplification (MLPA) for ultrasensitive multiplexed microRNA detection using ribonucleotide-modified DNA probes," Chem. Commun., 2013, 49:10013-10015.
Zhang et al., "Stripping custom microRNA microarrays and the lessons learned about probe-slide interactions," Anal Biochem., Mar. 2009, 386(2):222-7.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Asp et al., "Spatially Resolved Transcriptomes—Next Generation Tools for Tissue Exploration," Bioessays, Oct. 2020, 42(10):e1900221, 16 pages.
Balakrishnan et al., "Flap endonuclease 1," Annu Rev Biochem., Jun. 2013, 82:119-138.
Bergenstråhle et al., "Seamless integration of image and molecular analysis for spatial transcriptomics workflows," BMC Genomics, Jul. 2020, 21(1):482, 7 pages.
Berger el al., "Universal bases for hybridization, replication and chain termination," Nucleic Acid Res., Aug. 2000, 28(15):2911-2914.
Blair et al., "Microarray temperature optimization using hybridization kinetics," Methods Mol Biol., 2009, 529:171-96.
Bolotin et al., "MiXCR: software for comprehensive adaptive immunity profiling," Nat Methods., May 2015, 12(5):380-1.
Chen et al., "Parallel single nucleotide polymorphism genotyping by surface invasive cleavage with universal detection," Anal Chem., Apr. 2005, 77(8):2400-5.
Chester et al., "Dimethyl sulfoxide-mediated primer Tm reduction: a method for analyzing the role of renaturation temperature in the polymerase chain reaction." Anal Biochem, Mar. 1993, 209(2):284-90.
Ciaccio et al., "Systems analysis of EGF receptor signaling dynamics with microwestern arrays," Nat Methods, Feb. 2010, 7(2):148-55.
Gerard et al.. "Excess dNTPs minimize RNA hydrolysis during reverse transcription," Biotechniques, Nov. 2002, 33(5):984, 986, 988, 990.
Hessner et al., "Genotyping of factor V G1691A (Leiden) without the use of PCR by invasive cleavage of oligonucleotide probes," Clin Chem., Aug. 2000, 46(8 Pt 1):1051-6.
Hoffman et al., "Formaldehyde crosslinking: a tool for the study of chromatin complexes," J Biol Chem., Oct. 2015, 290(44):26404-11.
Hughes et al., "Microfluidic Western blotting," PNAS, Dec. 2012, 109(52):21450-21455.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Krzywkowski et al., "Chimeric padlock and iLock probes for increased efficiency of targeted RNA detection," RNA, Jan. 2019, 25(1):82-89.
Krzywkowski et al.,, "Fidelity of RNA templated end-joining by chlorella virus DNA ligase and a novel iLock assay with improved direct RNA detection accuracy," Nucleic Acids Research, Oct. 2017, 45(18):e161, 9pages.
Lvamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Nilsson et al., "RNA-templated DNA ligation for transcript analysis," Nucleic Acids Res., Jan. 2001, 29(2):578-81.
Olivier, "The Invader assay for SNP genotyping," Mutat. Res., Jun. 2005, 573(1-2):103-110.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perocchi et al., "Antisense artifacts in transcriptome microarray experiments are resolved by actinomycin D," Nucleic Acids Res., 2007, 35(19):e128, 7 pages.
Picelli et al., "Full-length RNA-seq from single cells using Smart-seq2," Nat Protoc., Jan. 2014, 9(1):171-81.
Schouten et al., "Relative quantification of 40 nucleic acid sequences by multiplex ligation-dependent probe amplification," Nucleic Acids Res., Jun. 2002, 30(12):e57, 13 pages.

(56) References Cited

OTHER PUBLICATIONS

Singh et al., "High-throughput targeted long-read single cell sequencing reveals the clonal and transcriptional landscape of lymphocytes," Nat Commun., Jul. 2019, 10(1):3120, 13 pages.
Sountoulidis et al., "SCRINSHOT, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Sutherland et al., "Utility of formaldehyde cross-linking and mass spectrometry in the study of protein-protein interactions," J. Mass Spectrom., Jun. 2008, 43(6):699-715.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Tu et al., "TCR sequencing paired with massively parallel 3' RNA-seq reveals clonotypic T cell signatures," Nature Immunology, Dec. 2019, 20(12):1692-1699.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
U.S. Appl. No. 16/353,937, filed Mar. 14, 2019, Frisen et al.
U.S. Appl. No. 17/707,189, filed Mar. 29, 2022, Chell et al.
Dalma-Weiszhausz et al., "The affymetrix GeneChip platform: an overview," Methods Enzymol., 2006, 410:3-28.
Illumina.com [online], "Ribo-Zero® rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Lahiani et al., "Enabling Histopathological Annotations on Immunofluorescent Images through Virtualization of Hematoxylin and Eosin," J Pathol Inform., Feb. 2018, 9:1, 8 pages.
Lou et al., "A review of room temperature storage of biospecimen tissue and nucleic acids for anatomic pathology laboratories and biorepositories," Clin Biochem., Mar. 2014, 47(4-5):267-73.
Lykidis et al., "Novel zinc-based fixative for high quality DNA, RNA and protein analysis." Nucleic Acids Res., Jun. 2007, 35(12):e85, 10 pages.
Miller et al., "Chapter 11—Solid and Suspension Microarrays for Microbial Diagnostics." Methods in Microbiology, 2015, 42:395-431.
Nadji et al., "Immunohistochemistry of tissue prepared by a molecular-friendly fixation and processing system," Appl Immunohistochem Mol Morphol., Sep. 2005, 13(3):277-82.
Niedringhaus et al., "Landscape of next-generation sequencing technologies," Anal Chem., Jun. 2011, 83(12):4327-41.
Passow et al., "RNAlater and flash freezing storage methods nonrandomly influence observed gene expression in RNAseq experiments," bioRxiv, Jul. 2018, 28 pages.
Porreca et al., "Polony DNA sequencing," Curr Protoc Mol Biol., Nov. 2006, Chapter 7, Unit 7.8, pp. 7.8.1-7.8.22.
Qiu et al., "Combination probes with intercalating anchors and proximal fluorophores for DNA and RNA detection," Nucleic Acids Research, Sep. 2016, 44(17):e138, 12 pages.
Schwers et al., "A high-sensitivity, medium-density, and target amplification-free planar waveguide microarray system for gene expression analysis of formalin-fixed and paraffin-embedded tissue." Clin. Chem., Nov. 2009, 55(11):1995-2003.
Vickovic et al., "SM-Omics: An automated Platform for High-Throughput Spatial Multi-Omics," bioRxiv, Oct. 2020, 40 pages.
Wang et al., "Optimization of Process Conditions for Infected Animal Tissues by Alkaline Hydrolysis Technology," Procedia Environmental Sciences, 2016, 31:366-374.
Wohnhaas et al., "DMSO cryopreservation is the method of choice to preserve cells for droplet-based single-cell RNA sequencing," Scientific Reports, Jul. 2019, 9(1):10699, 14 pages.
Zhao et al.,, "Isothermal Amplification of Nucleic Acids," Chemical Reviews, Nov. 2015, 115(22):12491-12545.
Burgess, "Spatial transcriptomics coming of age," Nat Rev Genet., Jun. 2019, 20(6):317, 1 page.
Ho et al., "Characterization of an ATP-Dependent DNA Ligase Encoded by Chlorella Virus PBCV-1," Journal of Virology, Mar. 1997, 71(3):1931-1937.
Hsuih et al., "Novel, Ligation-Dependent PCR Assay for Detection of Hepatitis C Virus in Serum," Journal of Clinical Microbiology, Mar. 1996, 34(3):501-507.
Kumar et al., "Template-directed oligonucleotide strand ligation, covalent intramolecular DNA circularization and catenation using click chemistry," J Am Chem Soc., May 2007, 129(21):6859-64.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ozsolak et al., "Digital transcriptome profiling from attomole-level RNA samples," Genome Res., Apr. 2010, 20(4):519-25.
Vandenbroucke et al., "Quantification of splice variants using real-time PCR," Nucleic Acids Research, 2001, 29(13):e68, 7 pages.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwdl9It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms," Nucl. Acids Res., 2000, 28(20):E87, 8 pages.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.

(56) References Cited

OTHER PUBLICATIONS

Armani et al, "2D-PCR: a method of mapping DNA in tissue sections," Lab Chip, 2009, 9(24):3526-34.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Birney et al., "Identification and analysis of functional elements in 1% of the human genome by the ENCODE pilot project," Nature, 2007, 447(7146):799-816.
Blanchard et al., "High-density oligonucleotide arrays," Biosensors & Bioelectronics, 1996, 11(6-7):687-690.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Constantine et al., "Use of genechip high-density oligonucleotide arrays for gene expression monitoring," Life Sceience News, Amersham Life Science, 1998, pp. 11-14.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Czarnik, "Encoding methods for combinatorial chemistry," Curr Opin Chem Biol., Jun. 1997, 1(1):60-6.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Dean et al., "Comprehensive human genome amplification using multiple displacement amplification," Proc Natl. Acad. Sci. USA, 2002, 99(8):5261-66.
Duncan et al., "Affinity chromatography of a sequence-specific DNA binding protein using Teflon-linked oligonucleotides," Anal. Biochem., 1988, 169(1):104-108.
Eguiluz et al., "Multitissue array review: a chronological description of tissue array techniques, applications and procedures," Pathology Research and Practice, 2006, 202(8):561-568.
Ellington et al., "Antibody-based protein multiplex platforms: technical and operational challenges," Clin Chem, 2010, 56(2):186-193.
Fodor et al., "Light-directed, spatially addressable parallel chemical synthesis," Science, 1995, 251(4995):767-773.
Frese et al., "Formylglycine aldehyde Tag—protein engineering through a novel post-translational modification," ChemBioChem., 2009, 10(3):425-27.
Fu et al., "Counting individual DNA molecules by the stochastic attachment of diverse labels," PNAS, 2011, 108(22):9026-9031.
Fu et al., "Continuous Polony Gels for Tissue Mapping with High Resolution and RNA Capture Efficiency," bioRxiv, 2021, 20 pages.
Ganguli et al., "Pixelated spatial gene expression analysis from tissue," Nat Commun., Jan. 2018, 9(1):202, 9 pages.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Gracia Villacampa et al., "Genome-wide Spatial Expression Profiling in FFPE Tissues," bioRxiv, 2020, pp. 38 pages.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hayes et al., "Electrophoresis of proteins and nucleic acids: I-Theory," BMJ, Sep. 1989, 299(6703):843-6.
He et al., "In situ synthesis of protein arrays," Current Opinion in Biotechnology, 2008, 19(1):4-9.
Hejatko et al., "In situ hybridization technique for mRNA detection in whole mount *Arabidopsis* samples," Nature Protocols, 2006, 1(4):1939-1946.
Ke et al., "In situ sequencing for RNA analysis in preserved tissue and cells," Nat Methods., Sep. 2013, Supplementary Materials, 29 pages.
Kristensen et al., "High-Throughput Methods for Detection of Genetic Variation," BioTechniques, Feb. 2001, 30(2):318-332.
Kurz et al., "cDNA—protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Landegren et al., "Reading bits of genetic information: methods for single-nucleotide polymorphism analysis," Genome Res., Aug. 1998, 8(8):769-76.
Leriche et al., "Cleavable linkers in chemical biology," Bioorganic & Medicinal Chemistry, 2012, 20:571-582.

(56) References Cited

OTHER PUBLICATIONS

Linnarsson, "Recent advances in DNA sequencing methods—general principles of sample preparation," Experimental Cell Research, 2010, 316(8):1339-1343.

Liu et al., "High-Spatial-Resolution Multi-Omics Atlas Sequencing of Mouse Embryos via Deterministic Barcoding in Tissue," BioRxiv, 2019, 55 pages.

Lizardi et al., "Mutation detection and single-molecule counting using isothermal rolling-circle amplification," Nat. Genet., 1998, 19(3):225-232.

Lundberg et al., "Multiplexed homogeneous proximity ligation assays for high-throughput protein biomarker research in serological material," Mol Cell Proteomics, 2011, 10(4):M110.004978, 11 pages.

MacBeath et al., "Printing proteins as microarrays for high-throughput function determination," Science, Sep. 2000, 289(5485):1760-1763.

Marx, "Method of the Year: spatially resolved transcriptomics," Nature Methods, 2021, 18(1):9-14.

Merritt et al., "Multiplex digital spatial profiling of proteins and RNA in fixed tissue," Nat Biotechnol, May 2020, 38(5):586-599.

Metzker, "Sequencing technologies—the next generation," Nature Reviews Genetics, 2010, 11(1):31-46.

Miller et al., "Basic concepts of microarrays and potential applications in clinical microbiology," Clinical Microbiology Reviews, 2009, 22(4):611-633.

Miner et al., "Molecular barcodes detect redundancy and contamination in hairpin-bisulfite PCR," Nucleic Acids Res., Sep. 2004, 32(17):e135, 4 pages.

Mishra et al., "Three-dimensional genome architecture and emerging technologies: looping in disease," Genome Medicine, 2017, 9(1):87, 14 pages.

Mitra et al., "Digital genotyping and haplotyping with polymerase colonies," Proc. Natl. Acad. Sci. USA, May 2003, 100(10):5926-5931.

Mizusawa et al., "A bacteriophage lambda vector for cloning with BamHI and Sau3A," Gene, 1982, 20(3):317-322.

Nikiforov et al., "The use of 96-well polystyrene plates for DNA hybridization-based assays: an evaluation of different approaches to oligonucleotide immobilization," Anal Biochem, May 1995, 227(1):201-9.

Nowak et al., "Entering the Postgenome Era," Science, 1995, 270(5235):368-71.

Pemov et al., "DNA analysis with multiplex microarray-enhanced PCR," Nucl. Acids Res., Jan. 2005, 33(2):e11, 9 pages.

Perler et al., "Intervening sequences in an Archaea DNA polymerase gen," Proc Natl Acad Sci USA, Jun. 1992, 89(12):5577-5581.

Petterson et al., "Generations of sequencing technologies," Genomics, 2009, 93(2):105-111.

Polsky-Cynkin et al., "Use of DNA immobilized on plastic and agarose supports to detect DNA by sandwich hybridization," Clin. Chem., 1985, 31(9):1438-1443.

Ranki et al., "Sandwich hybridization as a convenient method for the detection of nucleic acids in crude samples," Gene, 1983, 21(1-2):77-85.

Reinartz et al., "Massively parallel signature sequencing (MPSS) as a tool for in-depth quantitative gene expression profiling in all organisms," Brief Funct Genomic Proteomic, Feb. 2002, 1(1):95-104.

Ronaghi et al., "A sequencing method based on real-time pyrophosphate," Science, Jul. 1998, 281(5375):363-365.

Ronaghi et al., "Real-time DNA sequencing using detection of pyrophosphate release," Analytical Biochemistry, Nov. 1996, 242(1):84-89.

Ronaghi, "Pyrosequencing sheds light on DNA sequencing," Genome Res, Jan. 2001, 11(1):3-11.

Salmén et al., "Barcoded solid-phase RNA capture for Spatial Transcriptomics profiling in mammalian tissue sections," Nature Protocols, Oct. 2018, 13(11):2501-2534.

Saxonov et al., "10x Genomics, Mastering Biology to Advance Human Health," PowerPoint, 10x, 2020, 41 pages.

Schena et al., "Quantitative monitoring of gene expression patterns with a complementary DNA microarray," Science, Oct. 1995, 270(5235):467-470.

Shalon et al., "A DNA microarray system for analyzing complex DNA samples using two-color fluorescent probe hybridization," Genome Res., Jul. 1996, 6(7):639-45.

Stahl et al., "Visualization and analysis of gene expression in tissue sections by spatial transcriptomics," Science, Jun. 2016, 353(6294):78-82.

Stahl et al., "Visualization and analysis of gene expression in tissue sections by spatial transcriptomics," Supplementary Materials, Science, Jul. 2016, 353(6294):78-82, 41 pages.

Stimpson et al., "Real-time detection of DNA hybridization and melting on oligonucleotide arrays by using optical wave guides," Proc Natl Acad Sci USA, Jul. 1995, 92(14):6379-83.

Strell et al., "Placing RNA in context and space—methods for spatially resolved transcriptomics," The FEBS Journal, 2019, 286(8):1468-1481.

Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.

Twyman et al., "Techniques Patents for SNP Genotyping," Pharmacogenomics, Jan. 2003, 4(1):67-79.

Van Gelder et al., "Amplified RNA synthesized from limited quantities of heterogeneous cDNA," Proc. Natl. Acad. Sci. USA, 1990, 87(5):1663-1667.

Vasiliskov et al., "Fabrication of microarray of gel-immobilized compounds on a chip by copolymerization," Biotechniques, Sep. 1999, 27(3):592-606.

Vickovic et al., "High-definition spatial transcriptomics for in situ tissue profiling," Nat Methods, Oct. 2019, 16(10):987-990.

Vogelstein et al., "Digital PCR," Proceedings of the National Academy of Sciences, Aug. 1999, 96(16):9236-9241.

Walker et al., "Strand displacement amplification—an isothermal, in vitro DNA amplification technique," Nucleic Acids Research, 1992, 20(7):1691-1696.

Wang et al., "Imaging-based pooled CRISPR screening reveals regulators of lncRNA localization," Proc Natl Acad Sci USA, May 2019, 116(22):10842-10851.

Wang et al., "Tagmentation-based whole-genome bisulfite sequencing," Nature Protocols, Oct. 2013, 8(10):2022-2032.

Wang et al., "High-fidelity mRNA amplification for gene profiling," Nature Biotechnology, Apr. 2000, 18(4):457-459.

Worthington et al., "Cloning of random oligonucleotides to create single-insert plasmid libraries," Anal Biochem, 2001, 294(2):169-175.

Yershov et al., "DNA analysis and diagnostics on oligonucleotide microchips," Proc. Natl. Acad. Sci. USA, May 1996, 93(10):4913-4918.

Caliari et al., "A practical guide to hydrogels for cell culture," Nat Methods., Apr. 2016, 13(5):405-14.

Hanauer et al., "Separation of nanoparticles by gel electrophoresis according to size and shape," Nano Lett., Sep. 2007, 7(9):2881-5.

Ulery et al., "Biomedical Applications of Biodegradable Polymers," J Polym Sci B Polym Phys., Jun. 2011, 49(12):832-864.

Amidzadeh et al., "Assessment of different permeabilization methods of minimizing damage to the adherent cells for detection of intracellular RNA by flow cytometry," Avicenna J Med Biotechnol., Jan. 2014, 6(1):38-46.

Boulé et al., "Terminal deoxynucleotidyl transferase indiscriminately incorporates ribonucleotides and deoxyribonucleotides," J Biol Chem., Aug. 2001, 276(33):31388-93.

Evers et al., "The effect of formaldehyde fixation on RNA: optimization of formaldehyde adduct removal," J Mol Diagn., May 2011, 13(3):282-8.

Gansauge et al., "Single-stranded DNA library preparation from highly degraded DNA using T4 DNA ligase," Nucleic Acids Res., Jun. 2017, 45(10):e79, 10 pages.

(56) References Cited

OTHER PUBLICATIONS

Hafner et al., "Identification of microRNAs and other small regulatory RNAs using cDNA library sequencing," Methods, Jan. 2008, 44(1):3-12.

Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.

Slomovic et al., "Addition of poly(A) and poly(A)-rich tails during RNA degradation in the cytoplasm of human cells," Proc Natl Acad Sci USA, Apr. 2010, 107(16):7407-12

\* cited by examiner

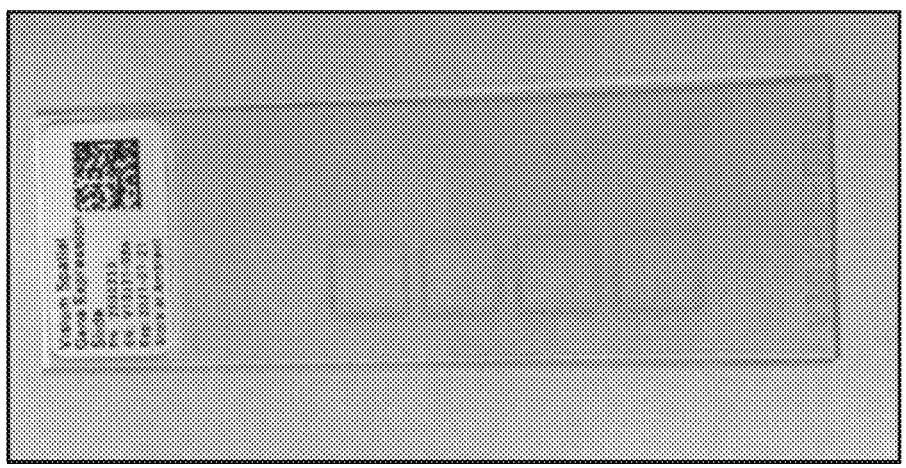
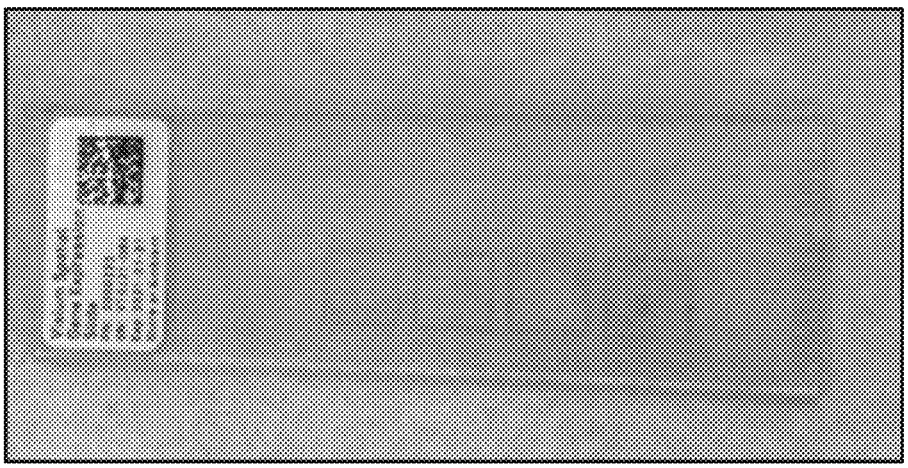
FIG. 2B

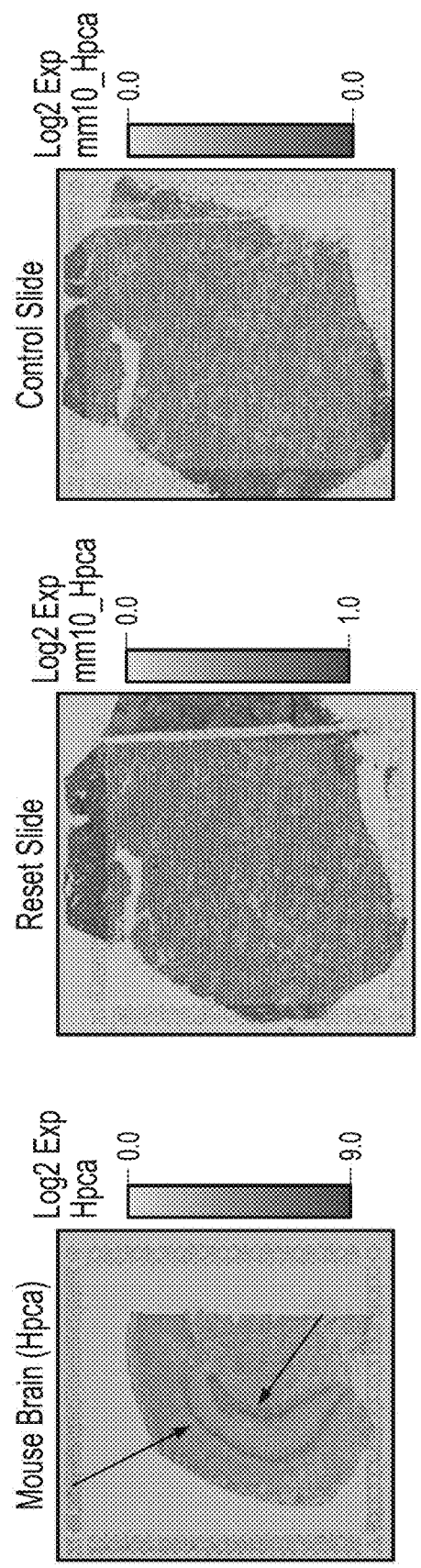

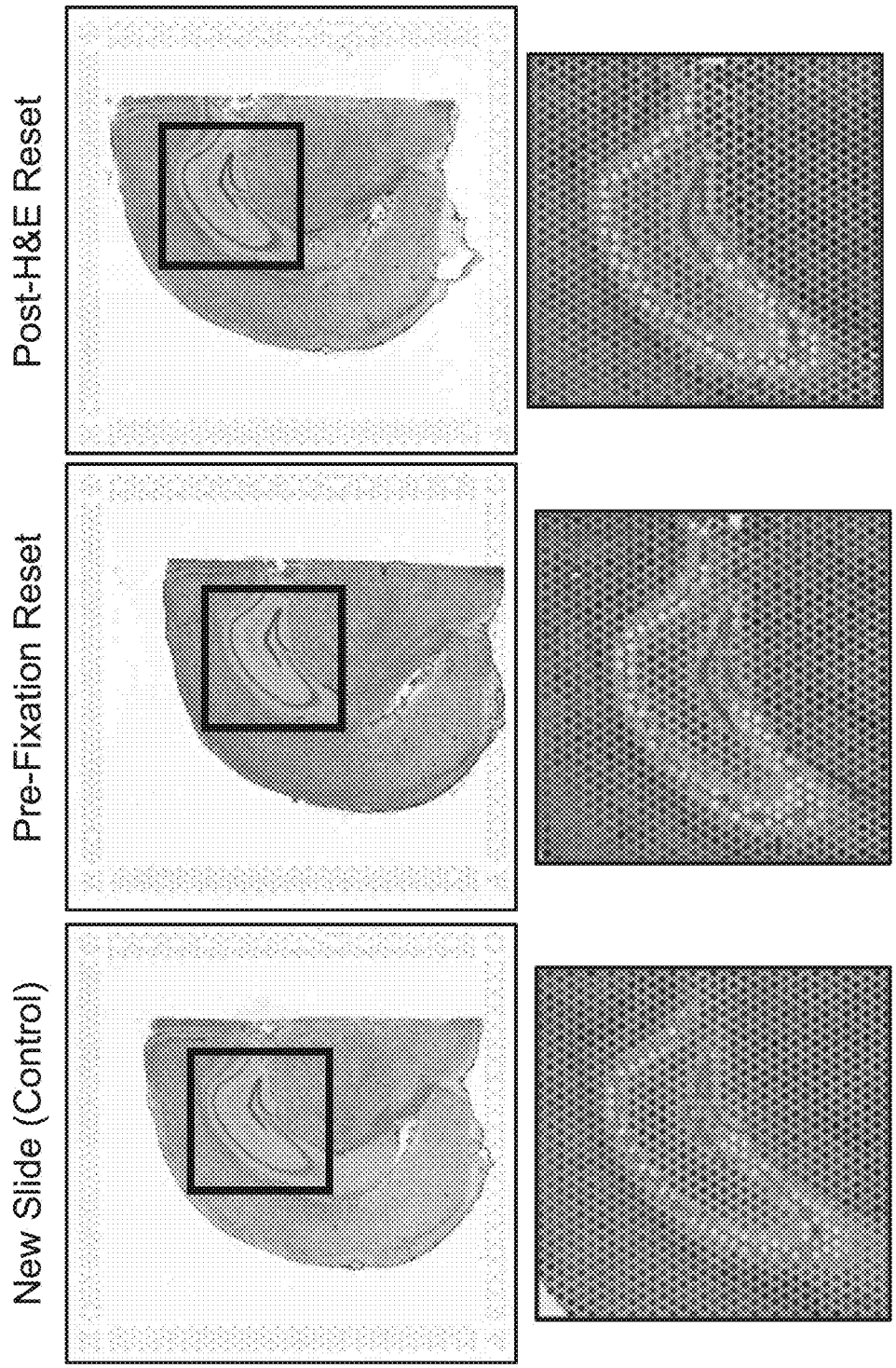

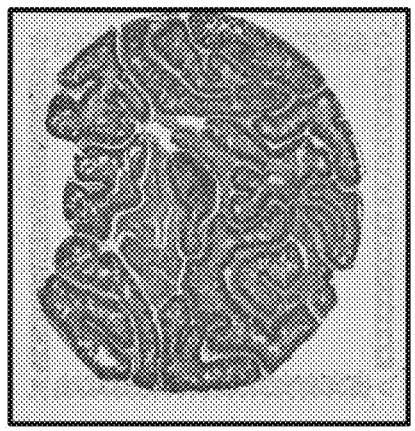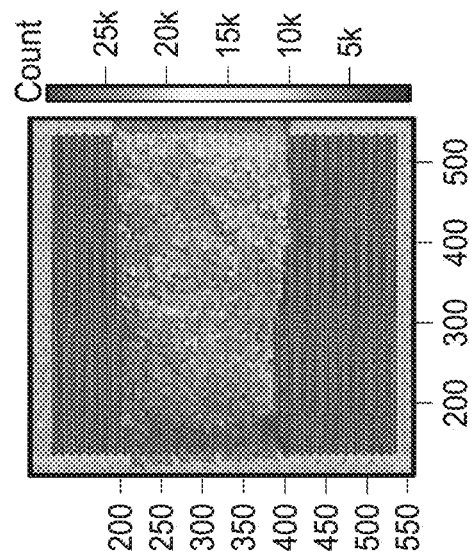
FIG. 16C
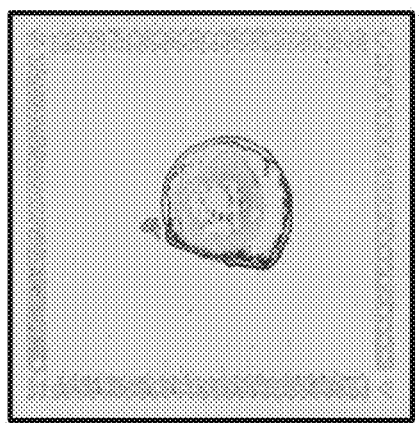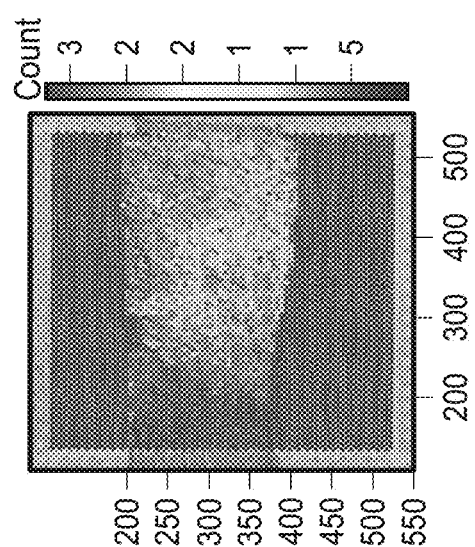
FIG. 16B
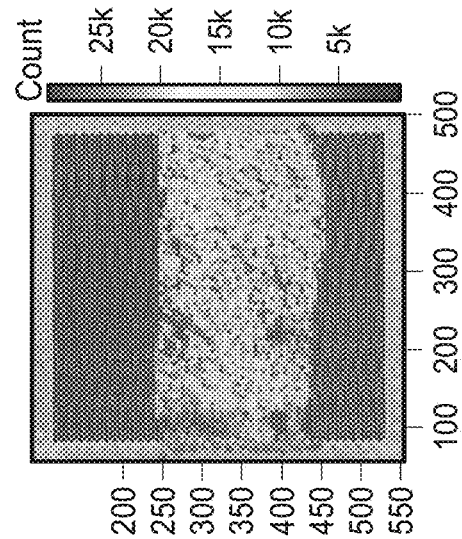
FIG. 16A

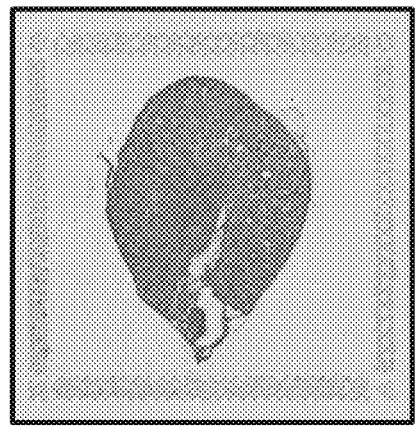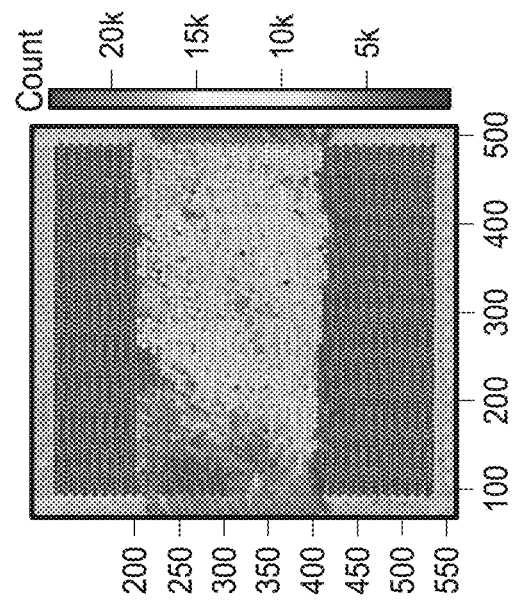
FIG. 16E
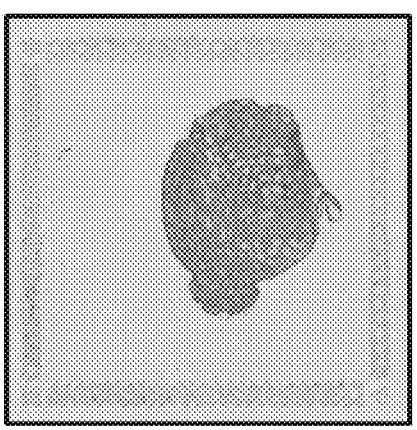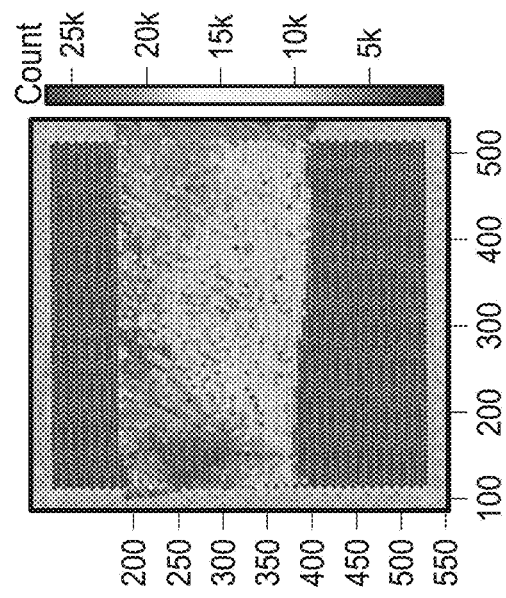
FIG. 16D

METHOD FOR RESETTING AN ARRAY

CROSS-REFERENCE TO RELATED APPLICATIONS

Pursuant to 35 U.S.C. § 119(e), this application is a continuation of International Patent Application PCT/US2021/034212, with an international filing date of May 26, 2021, which claims priority to U.S. Provisional Patent Application Ser. No. 63/030,190, filed on May 26, 2020 and U.S. Provisional Patent Application Ser. No. 63/041,481, filed on Jun. 19, 2020, each of which are hereby incorporated by reference in their entireties.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the context of an intact tissue or a portion of a tissue, or provide a lot of analyte data for single cells, but fail to provide information regarding the position of the single cell in a parent biological sample (e.g., tissue sample).

An array may be used to process a biological sample (e.g., tissue sample) for various purposes, such as identification or characterization of an analyte within the biological sample. However, incorrectly placing tissue sample within the capture area and/or placing damaged/folded tissue on the array have been proven to be a common issue when using arrays to study spatial organization of gene expression.

SUMMARY

Provided herein are methods of resetting an array, allowing removal of tissue from the array and reprocessing new tissue onto the array without seeing a significant decrease in sequencing metrics.

In one aspect, provided herein is a method for resetting an array, the method including: (a) applying a biological sample to an array wherein the array includes a plurality of capture probes, wherein a capture probe of the plurality of capture probes includes a capture domain that binds specifically to an analyte from the biological sample, (b) identifying that the biological sample has been applied to the array incorrectly or does not contain a region of interest, and (c) treating the array with a set of biological sample removal conditions, such that the biological sample is substantially removed from the array, wherein no reverse transcription has been performed prior to step (c), thereby resetting the array.

In another aspect, provided herein is a method for resetting an array to which a biological sample has been applied, the method including: (a) identifying that the biological sample has been applied to the array incorrectly or does not contain a region of interest, and (b) treating the array with a set of biological sample removal conditions, such that the biological sample is substantially removed from the array, wherein no reverse transcription has been performed on the array, wherein the array includes a plurality of capture probes, wherein a capture probe of the plurality of capture probes includes a capture domain that binds specifically to an analyte from the biological sample, thereby resetting the array.

In some embodiments, identifying that the biological sample has been applied to the array incorrectly can include identifying that one or more fiducial markers on the array is obscured by the biological sample. In some embodiments, identifying that the biological sample has been applied to the array incorrectly can include identifying that the biological sample is folded. In some embodiments, identifying that the biological sample has been applied to the array incorrectly can include identifying that the biological sample is torn or damaged. In some embodiments, identifying that the biological sample has been applied to the array incorrectly comprises identifying that the biological sample overlaps with a second biological sample. In some embodiments, identifying that the biological sample does not contain the region of interest can include imaging the biological sample after staining and/or immunofluorescence. In some embodiments, an image produced by imaging the biological sample demonstrates an incorrect application of a stain and/or an immunofluorescence antibody. In some embodiments, an image produced by imaging the biological sample demonstrates nonspecific staining of the biological sample.

Also provided herein is a method for resetting an array to which a biological sample has been applied, the method including: treating the array with a set of biological sample removal conditions, such that the biological sample is substantially removed from the array, wherein no reverse transcription has been performed on the array, wherein the array includes a plurality of capture probes, wherein a capture probe of the plurality of capture probes includes a capture domain that binds specifically to an analyte from the biological sample, thereby resetting the array.

Provided additionally herein is a method for resetting an array, the method including: (a) applying a biological sample to an array wherein the array includes a plurality of capture probes, wherein a capture probe of the plurality of capture probes includes a capture domain that binds specifically to an analyte from the biological sample, and (b) treating the array with a set of biological sample removal conditions, such that the biological sample is substantially removed from the array, wherein no reverse transcription has been performed prior to step (b), thereby resetting the array.

In some embodiments, the array can be a tissue optimization array. In some embodiments, treating the array with the set of biological sample removal conditions can include treating the array with a base. In some embodiments, the base can include a base selected from the group consisting of potassium hydroxide and sodium hydroxide. In some embodiments, treating the array with the base can include treating the array with about 40 mM to about 120 mM of the base. In some embodiments, treating the array with the base can include treating the array with about 75 mM to about 85 mM of the base. In some embodiments, treating the array with the base can include treating the array with the base for between about 1 minute and about 20 minutes. In some embodiments, treating the array with the base includes treating the array with the base for about 8 minutes to about 12 minutes. In some embodiments, treating the array with a base can include treating the array with a base for one, two, three, four or five cycles.

In some embodiments, treating the array with the set of biological sample removal conditions further can include washing the array with water one or more times. In some embodiments, the water can be nuclease-free water and/or ultrapure water.

In some embodiments, treating the array with the set of biological sample removal conditions further can include washing the array with a buffer one or more times. In some embodiments, the buffer can be selected from the group consisting of Tris, phosphate buffered saline (PBS), HEPES (4-(2-hydroxyethyl)-1-piperazineethanesulfonic acid), TES (2-[(2-Hydroxy-1,1-bis(hydroxymethyl)ethyl)amino]ethanesulfonic acid), and combinations thereof. In some embodiments, the buffer can have a concentration of about 1 mM to about 20 mM. In some embodiments, the buffer can have a concentration of about 8 mM to about 12 mM. In some embodiments, the buffer can have a pH of about 6.0 to about 8.0. In some embodiments, the buffer can have a pH of about 6.5 to about 7.5. In some embodiments, the buffer can have a pH of about 6.8 to about 7.2.

In some embodiments, treating the array with the set of biological sample removal conditions can further include drying the array.

In some embodiments treating the array with the set of biological sample removal conditions, the biological sample is not permeabilized.

In some embodiments, treating the array with the set of biological sample removal conditions can include, sequentially, treating the array with the base, washing the array with the buffer, washing the array with water, and optionally drying the array.

In some embodiments, treating the array with the set of biological sample removal conditions further can include treating the array with a proteinase. In some embodiments, treating the array with the proteinase precedes treating with the base. In some embodiments, the proteinase can be proteinase K. In some embodiments, treating the array with the proteinase can be for between 10 minutes and 2 hours. In some embodiments, treating the array with the proteinase can be for between 30 minutes and 90 minutes. In some embodiments, treating the array with the proteinase can be for about 55 minutes to about 65 minutes. In some embodiments, during treatment of the array with the proteinase, the biological sample can be incubated at between 40 degrees and 60 degrees Celsius. In some embodiments, during treatment of the array with proteinase, the biological sample can be incubated at between 45 degrees to about 55 degrees Celsius. In some embodiments, treating the array with the proteinase further can include treating the array with a surfactant and a proteinase buffer. In some embodiments, the surfactant can be sodium dodecyl sulfate. In some embodiments, the surfactant can be present in an amount of about 5% w/v to about 20% w/v. In some embodiments, the surfactant can be present in an amount of about 8% w/v to about 10% w/v. In some embodiments, the proteinase buffer can be Tris. In some embodiments, the proteinase buffer can have a concentration of about 1 mM to about 20 mM. In some embodiments, the proteinase buffer can have a concentration of about 8 mM to about 12 mM. In some embodiments, the proteinase buffer can have a pH of about 8.0 to about 10.0. In some embodiments, the proteinase buffer can have a pH of about 8.5 to about 9.5. In some embodiments, the proteinase buffer can have a pH of about 8.8 to about 9.2.

In some embodiments, treating the array with the set of biological sample removal conditions can include, sequentially, treating the array with the proteinease, washing the array with water, treating the array with the base, washing the array with the buffer, washing the array with water, and optionally drying.

In some embodiments, the array can include a slide. In some embodiments, the slide can be a glass slide.

In some embodiments, the biological sample can be an animal sample. In some embodiments, the biological sample can be a human sample. In some embodiments, the biological sample can be a rodent sample. In some embodiments, the biological sample can be a breast, brain, heart, small intestine, eye, testes, or kidney sample. In some embodiments, biological sample can be a cancerous sample or a sample suspected of having cancerous cells. In some embodiments, the biological sample can be a tissue section. In some embodiments, the tissue section can be a fresh frozen tissue section. In some embodiments, the biological sample can be fixed. In some embodiments, the biological sample can be formalin-fixed. In some embodiments, the biological sample can be fixed using methanol. In some embodiments, the biological sample can be fixed using acetone. In some embodiments, the biological sample can be stained. In some embodiments, the stain can be a histological stain. In some embodiments, the histological stain can be a hematoxylin and eosin stain. In some embodiments, the biological sample can be imaged using immunofluorescence.

Also provided herein is a method for capturing an analyte using an array, the method including: (a) resetting an array according to any one or more of the methods described herein, wherein the array is a spatial array and the capture probe further includes a spatial barcode, (b) contacting the spatial array with a biological sample, and (c) capturing an analyte from the biological sample on the spatial array. In some embodiments, the analyte can include RNA, DNA, a protein, a small molecule, or a metabolite. In some embodiments, the method can further include determining (i) all or a portion of a sequence corresponding to the spatial barcode, or a complement thereof, and (ii) all or a portion of a sequence corresponding to the analyte, or a complement thereof.

Also provided herein is a method for analyzing capture of a plurality of analytes on a tissue optimization array, the method including (a) resetting a tissue optimization array according to any of the tissue optimization resetting methods described herein, (b) contacting the tissue optimization array with a biological sample, (c) capturing a plurality of analytes from the biological sample on the tissue optimization array, and (d) analyzing the amount, distribution, and/or diffusion of the plurality of analytes based on the analytes from the biological sample captured on the tissue optimization array. In some embodiments, the plurality of analytes includes RNA, DNA, a protein, a small molecule, a metabolite, or a combination thereof. All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIG. 2B shows exemplary images of arrays after application of tissue removal conditions without potassium hydroxide (left) and tissue removal conditions including potassium hydroxide (right).

FIG. 5A-D shows plots and Dunnett's control data for spatial analyte data from control (non-reset) spatial arrays vs. reset spatial arrays for; FIG. 5A) Reads Mapped Confidently to Transcriptome, FIG. 5B) Fraction of Usable Reads, FIG. 5C) Median Genes/Spot and FIG. 5D) Median UMI Counts/Spot.

FIG. 6A-B show FIG. 6A) gene expression of HPCA, a gene highly expressed in the hippocampus region of mouse brain (indicated with arrows) and FIG. 6B) gene expression of HPCA on two arrays comprising ovarian tumor tissue sections: a reset array (left; wherein the array was previously in contact with mouse brain) and a control array (right; wherein the array had not been previously in contact with any other tissue); no detectable expression of mouse HPCA was observed in the reset array, indicating that there was no contamination or interference of mouse HPCA from mouse brain tissue section when analyzing the ovarian tumor tissue on the reset array.

FIGS. 7E-F demonstrate the affect of resetting a slide on the probes present on the slide. Blank OCT sections (containing no tissue samples) on array slides were processed through the reset workflow, FIG. 7F is exemplary of a reset slide and FIG. 7E is exemplary of a slide that was not reset (control). FIG. 7G shows the comparative fluoresence intensity of the Cy3 labelled Read 1 oligonucleotide binding to the reset and the control slides, showing minimal reduction in fluorescence and minimal affect of the reset protocol on the probes on the array.

FIG. 9B shows gene expression of MUCL1 on an array that originally had human breast cancer tissue on it, was subjected to tissue removal conditions including a single KOH wash, and a mouse brain tissue section was placed on it. Some spatial concentration of MUCL1 was observed on the reset array, indicating that there was some contamination or interference with MUCL1 from the human tissue with the mouse brain tissue of the reset array. FIG. 9C shows gene expression on an array that originally had human breast cancer tissue on it, was subjected to tissue removal conditions including two KOH washes, and mouse brain tissue was placed on it. No spatial concentration of MUCL1 was observed on the reset array, indicating that there was no contamination or interference with MUCL1 from the human tissue with the mouse brain tissue of the reset array.

FIG. 10A-F show box plots of control mouse brain data compared to reset arrays, with new human breast cancer or human heart tissue samples placed on the array with regard to: FIG. 10A) library quality, FIG. 10B) fraction of reads with primer, homopolymer, or switch oligo sequence, FIG. 10C) fraction of reads with ribosomal or mitochondrial UMI counts, and FIG. 10D) sensitivity. FIG. 10E shows overlaid UMAP plots of mouse brain data from a new array and reset arrays (either reset post H&E staining, reset prior to fixation, or a new slide control with no reset). FIG. 10F shows mouse brain tissue sections stained with hematoxylin and eosin (upper figures) and gene expression analysis of hippocalcin (HPCA) (lower figures) as determined on a new array and reset arrays (as conditions as found in FIG. 10E).

FIG. 11F shows overlaid UMAP plots of mouse brain data from a new (control) array and a reset array, both of which were processed using immunostaining. FIG. 11G shows a scatter plot of gene expression data from a new (control) array and a reset array, both of which were processed using immunostaining.

FIG. 16A-E show spatial gene analysis of human heart tissue on a FIG. 16A) new (control) array, and reset arrays that originally had FIG. 16B) mouse eye tissue, FIG. 16C) mouse small intestine tissue, FIG. 16D) mouse testes tissue, and FIG. 16E) mouse kidney tissue, placed on them.

DETAILED DESCRIPTION

Figure 1:
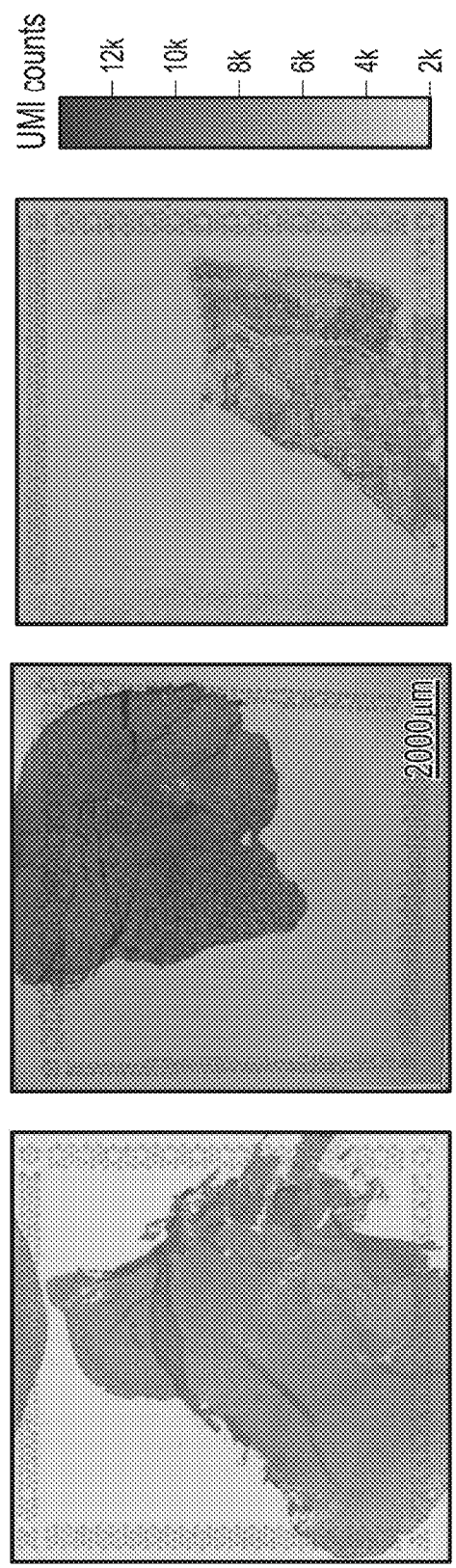
FIG. 1 shows images of fixed and stained tissue sections on an array. Tissue sections can be extremely thin and delicate, and positioning the tissue sections on an array with minimal folding or tearing of the tissue can be a difficult task. As seen in the images, parts of the tissue sections are not well positioned on the array (e.g., folded, torn, misaligned, or obscuring fiducials). A user may wish to remove such a tissue section from an array and either reposition the tissue section or apply a new tissue section to the array without interference or contamination from the first tissue section.

Placing a biological sample such as a tissue sample on a location on an array can be challenging. For example, tissue sections which are often around 5-10 µm thick can be difficult to handle. Tissue sections can fold back on themselves, they can tear or be damaged such that proceding with spatial assays to determine analyte locations within a tissue are compromised. In some cases, after imaging, a tissue sample can be determined not to contain a region of interest (e.g., tumor region or immune cell infiltrate). It would be very beneficial if, once placed on an array, a tissue sample could be removed, repositioned or altogether replaced with another tissue sample without compromising the downstream analysis (e.g., spatial assay). The present disclosure provides methods for repositioning, removing, replacing, or resetting a tissue sample on an array.

Spatial analysis methodologies and compositions described herein can provide a vast amount of analyte and/or expression data for a variety of analytes within a biological sample at high spatial resolution, while retaining native spatial context. Spatial analysis methods and compositions can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 10,774,374, 10,724,078, 10,480,022, 10,059,990, 10,041,949, 10,002,316, 9,879,313, 9,783,841, 9,727,810, 9,593,365, 8,951,726, 8,604,182, 7,709,198, U.S. Patent Application Publication Nos. 2020/239946, 2020/080136, 2020/0277663, 2020/024641, 2019/330617, 2019/264268, 2020/256867, 2020/224244, 2019/194709, 2019/161796, 2019/085383, 2019/055594, 2018/216161, 2018/051322, 2018/0245142, 2017/241911, 2017/089811, 2017/067096, 2017/029875, 2017/0016053, 2016/108458, 2015/000854, 2013/171621, WO 2018/091676, WO 2020/176788, Rodrigues et al., Science 363(6434):1463-1467, 2019; Lee et al., Nat. Protoc. 10(3):442-458, 2015; Trejo et al., PLoS ONE 14(2): e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev C, dated June 2020), and/or the Visium Spatial Tissue Optimization Reagent Kits User Guide (e.g., Rev C, dated July 2020), both of which are available at the 10× Genomics Support Documentation website, and can be used herein in any combination. Further non-limiting aspects of spatial analysis methodologies and compositions are described herein.

Some general terminology that may be used in this disclosure can be found in Section (I)(b) of WO 2020/176788 and/or U.S. Patent Application Publication No. 2020/0277663. Typically, a "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of WO 2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some embodiments, a biological sample can be a tissue section. In some embodiments, a biological sample can be a fixed and/or stained biological sample (e.g., a fixed and/or stained tissue section). Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of WO 2020/176788 and/or U.S. Patent Application Publication No. 2020/0277663.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of WO 2020/176788 and/or U.S. Patent Application Publication No. 2020/0277663.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of WO 2020/176788 and/or U.S. Patent Application Publication No. 2020/0277663. Generation of capture probes can be achieved by any appropriate method, including those described in Section (II)(d)(ii) of WO 2020/176788 and/or U.S. Patent Application Publication No. 2020/0277663.

In some embodiments, more than one analyte type (e.g., nucleic acids and proteins) from a biological sample can be detected (e.g., simultaneously or sequentially) using any appropriate multiplexing technique, such as those described in Section (IV) of WO 2020/176788 and/or U.S. Patent Application Publication No. 2020/0277663.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of WO 2020/176788 and/or Section (II)(b)(viii) U.S. Patent Application Publication No. 2020/0277663.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of WO 2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for a template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended using reverse transcription. In some embodiments, the capture probe is extended using one or more DNA polymerases. The extended capture probes include the sequence of the capture probe and the sequence of the spatial barcode of the capture probe.

In some embodiments, extended capture probes are amplified (e.g., in bulk solution or on the array) to yield quantities that are sufficient for downstream analysis, e.g., via DNA sequencing. In some embodiments, extended capture probes (e.g., DNA molecules) act as templates for an amplification reaction (e.g., a polymerase chain reaction).

Additional variants of spatial analysis methods, including in some embodiments, an imaging step, are described in Section (II)(a) of WO 2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of WO 2020/176788 and/or U.S. Patent Application Publication No. 2020/0277663. Some quality control measures are described in Section (II)(h) of WO 2020/176788 and/or U.S. Patent Application Publication No. 2020/0277663.

Spatial information can provide information of biological and/or medical importance. For example, the methods and compositions described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder.

Spatial information can provide information of biological importance. For example, the methods and compositions described herein can allow for: identification of transcriptome and/or proteome expression profiles (e.g., in healthy and/or diseased tissue); identification of multiple analyte types in close proximity (e.g., nearest neighbor analysis); determination of up- and/or down-regulated genes and/or proteins in diseased tissue; characterization of tumor microenvironments; characterization of tumor immune responses; characterization of cells types and their co-localization in tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A "feature" is an entity that acts as a support or repository for various molecular entities used in spatial analysis. In some embodiments, some or all of the features in an array are functionalized for analyte capture. Exemplary substrates are described in Section (II)(c) of WO 2020/176788 and/or U.S. Patent Application Publication No. 2020/0277663. Exemplary features and geometric attributes of an array can be found in Sections (II)(d)(i), (II)(d)(iii), and (II)(d)(iv) of WO 2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, "contact," "contacted," and/or "contacting," a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of WO 2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of WO 2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture domain (e.g., a poly(A) sequence, a non-homopolymeric sequence). After hybridization to the analyte, a ligase (e.g., SplintR ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). The released ligation product can then be captured by capture probes (e.g., instead of direct capture of an analyte) on an array, optionally amplified, and sequenced, thus determining the location and optionally the abundance of the analyte in the biological sample.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of WO 2020/176788 and/or U.S. Patent Application Publication No. 2020/0277663. See, for example, the Exemplary embodiment starting with "In some non-limiting examples of the workflows described herein, the sample can be immersed . . . " of WO 2020/176788 and/or U.S. Patent Application Publication No. 2020/0277663. See also, e.g., the Visium Spatial Gene Expression Reagent Kits User Guide (e.g., Rev C, dated June 2020), and/or the Visium Spatial Tissue Optimization Reagent Kits User Guide (e.g., Rev C, dated July 2020).

In some embodiments, spatial analysis can be performed using dedicated hardware and/or software, such as any of the systems described in Sections (II)(e)(ii) and/or (V) of WO 2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of WO 2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Application No. 2020/061064 and/or U.S. patent application Ser. No. 16/951,854.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Application No. 2020/053655 and spatial analysis methods are generally described in WO 2020/061108 and/or U.S. patent application Ser. No. 16/951,864.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of WO 2020/123320, PCT Application No. 2020/061066, and/or U.S. Patent Publication Serial No. 2021/0158522. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances. Arrays that can be reset using the methods described herein include, for example, tissue optimization arrays and spatial gene expression arrays. In some cases, an array can be a tissue optimization array used to evaluate analyte capture (e.g., by cDNA synthesis using fluorescent nucleotide analogs). In some cases an array can be a spatial array. Generally, capture probes on a spatial array include spatial barcodes, and capture probes on a tissue optimization array do not, though both include capture domains to capture analytes from a biological sample.

Provided herein are methods for resetting an array (e.g., a spatial array or a tissue optimization array). In some embodiments, the first biological sample is fixed, stained and imaged prior to removing the tissue sample from the array (e.g., a spatial array or a tissue optimization array). Also provided herein are methods of capturing an analyte using an array (e.g., a spatial array) that has been reset using any of the methods described herein. Also provided herein are methods for analyzing capture of a plurality of analytes on a tissue optimization array using a tissue optimization array that has been reset using any of the methods described herein. Array-based spatial analysis methods involve the use of a spatial array, where the spatial array includes an array of features on a substrate. In some embodiments, a biological sample (e.g., tissue sample) is contacted with the spatial array, generally allowing the transfer of one or more analytes from the biological sample to the array of features. In some embodiments, before a spatial analysis is performed, a biological sample is first analyzed using a tissue optimization array to determine the amount or presence of captured analyte for any given sample preparation and/or permeabilization condition.

In some embodiments, after contacting a biological sample with a substrate that includes an array of features (e.g., including a plurality of capture probes), a removal step can be performed to remove the biological sample from the substrate thereby resetting the array. Typically, array resetting occurs before a capture probe of the plurality of capture probes has been enzymatically extended to include a sequence complementary to all or a part of a sequence of an analyte from the biological sample. In some workflows, reverse transcription is used to enzymatically extend a capture probe of the plurality of capture probes to include a sequence complementary to all or part of a sequence of an analyte from the biological sample. Accordingly, in some embodiments, resetting an array occurs before reverse transcription has occurred on the array. In some embodiments, resetting an array occurs before an extension reaction (e.g., an enzymatic extension reaction) has occurred on the array (e.g., performed on a capture probe). In some embodiments, the biological sample is not permeabilized before the array is reset.

As used herein, "resetting" an array refers to the removal of a first tissue that was positioned on an array. In some embodiments, resetting an array can be followed by repositioning a first tissue on the array. In some embodiments, an array is reset in order to position another biological tissue sample on the array (e.g., a second portion of the same biological sample, or a biological sample from a different source, study, or organism). In some embodiments, an array may be reset once. In some embodiments, an array may be reset twice, three times, four times, or five times. In some embodiments, the array is reset in order to be used again, preferably before reverse transcription is performed on the array. In some embodiments, the array is reset in order to be used again, preferably before an extension reaction (e.g., an enzymatic extension reaction) has occurred on the array (e.g., performed on a capture probe).

In some embodiments, a method for resetting an array to which a biological sample has been applied includes treating the array with a set of biological sample removal conditions, such that the biological sample is substantially removed from the array.

In some embodiments, a method for resetting an array includes (a) applying a biological sample to an array comprising a plurality of capture probes, wherein a capture probe of the plurality of capture probes includes a capture domain that binds specifically to an analyte from the biological sample, and (b) treating the array with a set of biological sample removal conditions, such that the biological sample is substantially removed from the array, thereby resetting the array.

In some embodiments, a method for resetting an array to which a biological sample has been applied includes (a) identifying that the biological sample has been applied to the array incorrectly or does not contain a region of interest, and (b) treating the array with a set of biological sample removal conditions, thereby resetting the array.

As used herein, identifying that a biological sample has been applied to an array "incorrectly" can include identifying that one or more fiducial markers on the array is obscured by the biological sample, identifying that the biological sample is folded, identifying that the biological sample is torn or damaged, identifying that the biological sample was applied to the wrong array section, identifying that the biological sample overlaps with a second biological sample, or a combination thereof.

In some embodiments, identifying that the biological sample does not contain the region of interest includes imaging the biological sample after staining and/or immunofluorescence. In some cases, an image produced by imaging the biological sample demonstrates an incorrect application of a stain and/or an immunofluorescence antibody. In some cases, an image produced by imaging the biological sample demonstrates nonspecific staining of the biological sample.

In some embodiments, a method for resetting an array includes (a) applying a biological sample to an array including a plurality of capture probes, wherein a capture probe of the plurality of capture probes includes a capture domain that binds specifically to an analyte from the biological sample, (b) identifying that the biological sample has been applied to the array incorrectly or does not contain a region of interest, and (c) treating the array with a set of biological sample removal conditions, such that the biological sample is substantially removed from the array, thereby resetting the array.

In some embodiments of any of the methods described herein, resetting an array is performed before one or more potentially irreversible alterations to the array. In some embodiments, resetting an array occurs before reverse transcription has occurred on the array. In some embodiments, resetting an array occurs before an enzymatic extension reaction has occurred on the array (e.g., performed on a capture probe). In some embodiments, resetting an array occurs before an extension reaction has occurred on the array (e.g., performed on a capture probe).

In some embodiments, a biological sample is removed from an array to reset the array. In some embodiments, a method of removing a biological sample from an array comprises treating the array with a set of biological sample removal conditions, such that the biological sample is substantially removed from the array.

In some embodiments, resetting an array is performed before the biological sample is imaged; however, it may be easier for a user to identify that the biological sample was incorrectly placed or does not contain a region of interest with a visual aid. For example, it may be easier to identify that the biological sample obscures one or more fiducual markers on the array, or that the biological sample has been folded or torn using a visual aid. As another example, it may be easier to identify that the biological sample does not contain a region of interest after immunofluorescence. Accordingly, in some embodiments, resetting an array is performed after the biological sample is fixed and stained. In some embodiments, resetting an array is performed after the biological sample is fixed. In some embodiments, the biological sample can be fixed in any of the variety of fixatives described in, for example, in Section (I)(d)(ii)(3)-(6) of WO 2020/176788 and/or U.S. Patent Application Publication No. 2020/0277663. In some embodiments, the biological sample is stained. In some embodiments, the biological sample can be stained using known staining techniques, including but not limited to, Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. See, for example, Sections (I)(d)(ii)(3)-(6) of WO 2020/176788 and/or U.S. Patent Application Publication No. 2020/0277663 for fixing and staining techniques. In some embodiments, resetting an array is performed after the biological sample is evaluated using immunofluorescence. As such, resetting an array can be performed after fixing, immunofluorescence, staining, and/or imaging but prior to performing analyte capture and downstream enzymatic reactions on the captured analyte, for example reverse transcription of a captured mRNA molecule. Once analytes from a biological sample have been captured and extended on the array, the spatial barcodes are associated with the spatial location of the captured analyte in the biological sample. However, staining and/or fixing of a biological sample leaves the spatial barcodes intact thereby allowing for array resetting.

Treating an array (e.g., spatial array or tissue optimization array) to which a biological sample has been applied with a set of biological sample removal conditions can include treating the array with any appropriate reagents, temperatures, or other conditions. Typically, treating an array with a set of biological sample removal conditions includes treating the array with a base. In some embodiments, for example, treating the array with a base is the first part of the set of biological sample removal conditions. In some embodiments, the biological sample on the array is first treated enzymatically and/or chemically to degrade the biological sample prior to treating the array with a base.

In some embodiments, treating an array (e.g., spatial array or tissue optimization array) to which a biological sample has been applied with a set of biological sample removal conditions can include treating enzymatically and/or chemically to degrade the biological sample. For example, treating an array to which a biological sample has been applied with a set of biological sample removal conditions can include treating the array with an enzyme (e.g., a proteinase, e.g., proteinase K) to remove at least a portion of the biological sample from the array (e.g., on a glass slide). In some embodiments, treating an array to which a biological sample has been applied with a set of biological sample removal conditions can include ablation of the biological sample (e.g., laser ablation). In some embodiments, treating an array to which a biological sample has been applied with a set of biological sample removal conditions can include treating the array with a proteinase. In some embodiments, the proteinase is proteinase K. Treating with a proteinase can include any appropriate conditions, e.g., to allow the proteinase to function. In some embodiments, treating with a proteinase can include treating with a buffer (e.g., Tris, phosphate buffered saline (PBS), HEPES (4-(2-hydroxyethyl)-1-piperazineethanesulfonic acid), TES (2-[(2-Hydroxy-1,1-bis(hydroxymethyl)ethyl)amino]ethanesulfonic acid), and combinations thereof) at an appropriate pH (e.g., about pH 8.0 to about 10.0 (e.g., pH about 8.5 to about 9.5, about 8.8 to about 9.2, or about 9.0)) and appropriate concentration (e.g., about 1 mM to about 20 mM (e.g., about 5 mM to about 15 mM, about 8 mM to about 12 mM, or about 10 mM)), optionally with one or more additional reagents, such as a surfactant (e.g., sodium dodecyl sulfate) at any appropriate concentration (e.g., about 5% to about 15% w/v (e.g., about 8% to about 12% w/v, or about 10% w/v)).

In some embodiments, the array (e.g., spatial array or tissue optimization array) is treated with the proteinease (e.g., proteinase K) for between 10 minutes and 120 minutes (e.g., between 10 minutes and 100 minutes, between 10 minutes and 90 minutes, between 10 minutes and 80 minutes, between 10 minutes and 70 minutes, between 10 minutes and 60 minutes, between 10 minutes and 45 minutes, between 10 minutes and 30 minutes, between 30 minutes and 120 minutes, between 30 minutes and 100 minutes, between 30 minutes and 90 minutes, between 30 minutes and 80 minutes, between 30 minutes and 70 minutes, between 30 minutes and 60 minutes, between 30 minutes and 45 minutes, between 45 minutes and 120 minutes, between 45 minutes and 100 minutes, between 45 minutes and 90 minutes, between 45 minutes and 80 minutes, between 45 minutes and 70 minutes, between 45 minutes and 60 minutes, between 60 minutes and 120 minutes, between 60 minutes and 100 minutes, between 60 minutes and 90 minutes, between 60 minutes and 80 minutes, between 60 minutes and 70 minutes, between 70 minutes and 120 minutes, between 70 minutes and 100 minutes, between 70 minutes and 90 minutes, between 70 minutes and 80 minutes, between 80 minutes and 120 minutes, between 80 minutes and 100 minutes, between 80 minutes and 90 minutes, between 90 minutes and 120 minutes, between 90 minutes and 100 minutes, or between 100 minutes and 120 minutes). In some embodiments, the array is treated with proteinase K for approximately 60 minutes.

In some embodiments, the array (e.g., spatial array or tissue optimization array) is incubated during the treatment with a proteinase at a temperature between 40 degrees and 60 degrees (e.g., between 40 degrees and 58 degrees, between 40 degrees and 56 degrees, between 40 degrees and 54 degrees, between 40 degrees and 52 degrees, between 40 degrees and 50 degrees, between 40 degrees and 48 degrees, between 40 degrees and 46 degrees, between 40 degrees and 44 degrees, between 40 degrees and 42 degrees, between 42 degrees and 60 degrees, between 42 degrees and 58 degrees, between 42 degrees and 56 degrees, between 42 degrees and 54 degrees, between 42 degrees and 52 degrees, between 42 degrees and 50 degrees, between 42 degrees and 48 degrees, between 42 degrees and 46 degrees, between 42 degrees and 44 degrees, between 44 degrees and 60 degrees, between 44 degrees and 58 degrees, between 44 degrees and 56 degrees, between 44 degrees and 54 degrees, between 44 degrees and 52 degrees, between 44 degrees and 50 degrees, between 44 degrees and 48 degrees, between 44 degrees and 46 degrees, between 46 degrees and 60 degrees, between 46 degrees and 58 degrees, between 46 degrees and 56 degrees, between 46 degrees and 54 degrees, between 46 degrees and 52 degrees, between 46 degrees and 50 degrees, between 46 degrees and 48 degrees, between 48 degrees and 60 degrees, between 48 degrees and 58 degrees, between 48 degrees and 56 degrees, between 48 degrees and 54 degrees, between 48 degrees and 52 degrees, between 48 degrees and 50 degrees, between 50 degrees and 60 degrees, between 50 degrees and 58 degrees, between 50 degrees and 56 degrees, between 50 degrees and 54 degrees, between 50 degrees and 52 degrees, between 52 degrees and 60 degrees, between 52 degrees and 58 degrees, between 52 degrees and 56 degrees, between 52 degrees and 54 degrees, between 54 degrees and 60 degrees, between 54 degrees and 58 degrees, between 54 degrees and 56 degrees, between 56 degrees and 60 degrees, between 56 degrees and 58 degrees, or between 58 degrees and 60 degrees) Celsius. In some embodiments, the array is incubated during the application of a proteinase at a temperature of approximately 50 degrees Celsius.

In some embodiments, treating an array (e.g., spatial array or tissue optimization array) to which a biological sample has been applied with a set of biological sample removal conditions can include treating the array with a base (e.g., soaking the array in a base). In some embodiments, the base can be sodium hydroxide (NaOH), potassium hydroxide (KOH), or a combination thereof. Additional suitable bases that can be used in the methods described herein are known in the art. In some embodiments, the array is treated with the base for between 1 minute and 20 minutes (e.g., between 1 minute and 18 minutes, between 1 minute and 16 minutes, between 1 minute and 14 minutes, between 1 minute and 12 minutes, between 1 minute and 10 minutes, between 1 minute and 8 minutes, between 1 minute and 6 minutes, between 1 minute and 4 minutes, between 1 minute and 2 minutes, between 2 minutes and 20 minutes, between 2 minutes and 18 minutes, between 2 minutes and 16 minutes, between 2 minutes and 14 minutes, between 2 minutes and 12 minutes, between 2 minutes and 10 minutes, between 2 minutes and 8 minutes, between 2 minutes and 6 minutes, between 2 minutes and 4 minutes, between 4 minutes and 20 minutes, between 4 minutes and 18 minutes, between 4 minutes and 16 minutes, between 4 minutes and 14 minutes, between 4 minutes and 12 minutes, between 4 minutes and 10 minutes, between 4 minutes and 8 minutes, between 4 minutes and 6 minutes, between 6 minutes and 20 minutes, between 6 minutes and 18 minutes, between 6 minutes and 16 minutes, between 6 minutes and 14 minutes, between 6 minutes and 12 minutes, between 6 minutes and 10 minutes, between 6 minutes and 8 minutes, between 8 minutes and 20 minutes, between 8 minutes and 18 minutes, between 8 minutes and 16 minutes, between 8 minutes and 14 minutes, between 8 minutes and 12 minutes, between 8 minutes and 10 minutes, between 10 minutes and 20 minutes, between 10 minutes and 18 minutes, between 10 minutes and 16 minutes, between 10 minutes and 14 minutes, between 10 minutes and 12 minutes, between 12 minutes and 20 minutes, between 12 minutes and 18 minutes, between 12 minutes and 16 minutes, between 12 minutes and 14 minutes, between 14 minutes and 20 minutes, between 14 minutes and 18 minutes, between 14 minutes and 16 minutes, between 16 minutes and 20 minutes, between 16 minutes and 18 minutes, or between 18 minutes and 20 minutes). In some embodiments, the array is treated with the base for approximately 5 minutes. In some embodiments, the array is treated with the base for approximately 10 minutes.

In some embodiments, the array (e.g., spatial array or tissue optimization array) is treated with the base at a concentration of approximately 0.08 M. In some embodiments, the array is treated with the base (e.g., potassium hydroxide) at a concentration of about 0.01 M to 0.2 M, including, but not limited to, about 0.01 M, about 0.02 M, about 0.03 M, 0.04 M, about 0.05 M, about 0.06 M, about 0.07 M, about 0.08 M, about 0.09 M, about 0.10 M, about 0.11 M, about 0.12 M, about 0.13 M, about 0.14 M, about 0.15 M, about 0.16 M, about 0.17 M, about 0.18 M, about 0.19 M, or about 0.20 M, or any ranges included therein. In some embodiments, the biological sample is completely removed from the array after the array is treated with the base. In some embodiments, removing the biological sample from the array further comprises rinsing and drying the array. In some embodiments, the array is treated for a second time with base, using any of the times or concentrations of base described herein. In some cases, treating the array with the base can remove or help to remove any nucleic acid (e.g., RNA) hybridized to a capture probe on the array.

In some embodiments, treating an array (e.g., spatial array or tissue optimization array) to which a biological sample has been applied with a set of biological sample removal conditions can include washing the array with water (e.g., nuclease-free water and/or ultrapure water), washing the array with a buffer, and drying, or a combination thereof. A buffer can be any appropriate buffer, for example Tris, phosphate buffered saline (PBS), HEPES (4-(2-hydroxyethyl)-1-piperazineethanesulfonic acid), TES (2-[(2-Hydroxy-1,1-bis(hydroxymethyl)ethyl)amino]ethanesulfonic acid), at any appropriate pH (e.g., about 6.0 to about 8.0 (e.g., about 6.5 to about 7.5, about 6.8 to about 7.2, or about 7.0)) and any appropriate concentration (e.g., about 1 mM to about 20 mM (e.g., about 5 mM to about 15 mM, about 8 mM to about 12 mM, or about 10 mM)). Washing the array (e.g., with water or buffer) can include repeatedly washing the array (e.g., 10, 15, 20, or more times). In some embodiments, drying can include centrifugation and/or air drying. For example, in some embodiments, treating an array to which a biological sample has been applied with a set of biological sample removal conditions can include, sequentially, treating the array with a base (e.g., 0.08 M KOH for 10 minutes), optionally treating with a base for a second time (e.g., 0.08 M KOH for 5 minutes), washing with buffer (e.g., 10 mM Tris, pH 7.0, 15 times), washing with water (e.g, nuclease-free water and/or ultrapure water, 20 times), and optionally drying (e.g., via centrifugation or air drying). For example, in some embodiments, treating an array to which a biological sample has been applied with a set of biological sample removal conditions can include, sequentially, treating the array with a proteinase (e.g., at 3.3 mg/mL in 10 mM Tris, pH 9 and 10% sodium dodecyl sulfate) treating the array with a base (e.g., 0.08 M KOH for 10 minutes), optionally treating with a base for a second time (e.g., 0.08 M KOH for 5 minutes), washing with buffer (e.g., 10 mM Tris, pH 7.0, 15 times), washing with water (e.g, nuclease-free water and/or ultrapure water, 20 times), and optionally drying (e.g., via centrifugation or air drying).

A reset array (e.g., spatial array or tissue optimization array) can be stored at room temperature or 4° C. in a sealed container or a dessicator for up to 7 days before placing a new biological sample on the array.

Also provided herein are methods for using of an array (e.g., spatial array or tissue optimization array) reset using any of the methods described herein. In some embodiments, methods for using an array include resetting an array using any of the methods described herein, contacting the array with a biological sample (e.g., a second portion of a biological sample or a biological sample from a different source, study, or organism), and capturing an analyte from the biological sample on the array.

Also provided herein are methods for performing a spatial analysis using a spatial array reset using any of the methods described herein. In some embodiments, methods for performing a spatial analysis include resetting a spatial array using any of the methods described herein, contacting the spatial array with a biological sample (e.g., a second portion of a biological sample or a biological sample from a different source, study, or organism), and capturing an analyte from the biological sample on the spatial array. In some embodiments, the methods can further include determining (i) all or a portion of a sequence corresponding to the spatial barcode, or a complement thereof, and (ii) all or a portion of a sequence corresponding to the analyte, or a complement thereof.

Also provided herein are methods for analyzing analyte capture using a tissue optimization array reset using any of the methods described herein. In some embodiments, methods for analyzing analyte capture include resetting a tissue optimization array using any of the methods described herein, contacting the tissue optimization array with a biological sample (e.g., a second portion of a biological sample or a biological sample from a different source, study, or organism), capturing a plurality of analytes from the biological sample on the tissue optimization array, and analyzing the amount, distribution, diffusion, or a combination thereof, of the analytes.

Exemplary Embodiments

Embodiment 1 is a method for resetting an array, the method comprising:
(a) applying a biological sample to an array, wherein the array comprises a plurality of capture probes, wherein a capture probe of the plurality of capture probes comprises a capture domain that binds specifically to an analyte from the biological sample;
(b) identifying that the biological sample has been applied to the array incorrectly or does not contain a region of interest; and
(c) treating the array with a set of biological sample removal conditions, such that the biological sample is substantially removed from the array, thereby resetting the array.

Embodiment 2 is a method for resetting an array to which a biological sample has been applied, the method comprising:
(a) identifying that the biological sample has been applied to the array incorrectly or does not contain a region of interest; and
(b) treating the array with a set of biological sample removal conditions, such that the biological sample is substantially removed from the array,
wherein the array comprises a plurality of capture probes, wherein a capture probe of the plurality of capture probes comprises a capture domain that binds specifically to an analyte from the biological sample, thereby resetting the array.

Embodiment 3 is the method of embodiment 1 or embodiment 2, wherein identifying that the biological sample has been applied to the array incorrectly comprises identifying that one or more fiducial markers on the array is obscured by the biological sample.

Embodiment 4 is the method of any one of embodiments 1-3, wherein identifying that the biological sample has been applied to the array incorrectly comprises identifying that the biological sample is folded.

Embodiment 5 is the method of any one of embodiments 1-4, wherein identifying that the biological sample has been applied to the array incorrectly comprises identifying that the biological sample is torn or damaged.

Embodiment 6 is the method of any one of embodiments 1-5, wherein identifying that the biological sample has been applied to the array incorrectly comprises identifying that the biological sample overlaps with a second biological sample.

Embodiment 7 is the method of any one of embodiments 1-6, wherein identifying that the biological sample does not contain the region of interest comprises imaging the biological sample after staining and/or immunofluorescence.

Embodiment 8 is the method of embodiment 7, wherein an image produced by imaging the biological sample demonstrates an incorrect application of a stain and/or an immunofluorescence antibody.

Embodiment 9 is the method of embodiment 7 or embodiment 8, wherein an image produced by imaging the biological sample demonstrates nonspecific staining of the biological sample.

Embodiment 10 is a method for resetting an array to which a biological sample has been applied, the method comprising:
treating the array with a set of biological sample removal conditions, such that the biological sample is substantially removed from the array,
wherein the array comprises a plurality of capture probes, wherein a capture probe of the plurality of capture probes comprises a capture domain that binds specifically to an analyte from the biological sample, thereby resetting the array.

Embodiment 11 is a method for resetting an array, the method comprising:
(a) applying a biological sample to an array wherein the array comprises a plurality of capture probes, wherein a capture probe of the plurality of capture probes comprises a capture domain that binds specifically to an analyte from the biological sample; and
(b) treating the array with a set of biological sample removal conditions, such that the biological sample is substantially removed from the array, thereby resetting the array.

Embodiment 12 is the method of any one of embodiments 1-11, wherein the array is a tissue optimization array or a spatial array.

Embodiment 13 is the method of any one of embodiments 1-12, wherein prior to treating the array with the set of biological sample removal conditions, no reverse transcription has been performed on the array.

Embodiment 14 is the method of any one of embodiments 1-12, wherein prior to treating the array with the set of biological sample removal conditions, no enzymatic extension reaction has been performed on the capture probe.

Embodiment 15 is the method of embodiment 14, wherein no extension reaction has been performed on the capture probe.

Embodiment 16 is the method of any one of embodiments 1-15, wherein treating the array with the set of biological sample removal conditions comprises treating the array with a base.

Embodiment 17 is the method of embodiment 16, wherein the base comprises a base selected from the group consisting of potassium hydroxide, sodium hydroxide, and combinations thereof.

Embodiment 18 is the method of embodiment 16 or 17, wherein treating with the base comprises treating the array with about 40 mM to about 120 mM of the base.

Embodiment 19 is the method of any one of embodiments 16-18, wherein treating the array with the base comprises treating the array with about 75 mM to about 85 mM of the base.

Embodiment 20 is the method of any one of embodiments 16-19, wherein treating the array with the base comprises treating the array with the base for between about 1 minute and about 20 minutes.

Embodiment 21 is the method of any one of embodiments 16-20, wherein treating the array with the base comprises treating the array with the base for about 8 minutes to about 12 minutes.

Embodiment 22 is the method of any one of embodiments 16-21, wherein treating the array with a base comprises treating the array with a base for one, two, three, four or five times.

Embodiment 23 is the method of any one of embodiments 16-22, wherein treating the array with the set of biological sample removal conditions further comprises washing the array one or more times.

Embodiment 24 is the method of embodiment 23, wherein the washing comprises water that is nuclease-free water and/or ultrapure water.

Embodiment 25 is the method of any one of embodiments 16-24, wherein treating the array with the set of biological sample removal conditions further comprises washing the array with a buffer one or more times.

Embodiment 26 is the method of embodiment 25, wherein the buffer is selected from the group consisting of Tris, phosphate buffered saline (PBS), HEPES (4-(2-hydroxyethyl)-1-piperazineethanesulfonic acid), TES (2-[(2-Hydroxy-1,1-bis(hydroxymethylethyl)amino]ethanesulfonic acid), and combinations thereof.

Embodiment 27 is the method of embodiment 25 or 26, wherein the buffer has a concentration of about 1 mM to about 20 mM.

Embodiment 28 is the method of any one of embodiments 25-27, wherein the buffer has a concentration of about 8 mM to about 12 mM.

Embodiment 29 is the method of any one of embodiments 25-28, wherein the buffer has a pH of about 6.0 to about 8.0.

Embodiment 30 is the method of any one of embodiments 25-29, wherein the buffer has a pH of about 6.5 to about 7.5.

Embodiment 31 is the method of any one of embodiments 25-30, wherein the buffer has a pH of about 6.8 to about 7.2.

Embodiment 32 is the method of any one of embodiments 16-31, wherein treating the array with the set of biological sample removal conditions further comprises drying the array.

Embodiment 33 is the method of any one of embodiments 1-32, wherein, before treating the array with the set of biological sample removal conditions, the biological sample is not permeabilized.

Embodiment 34 is the method of embodiment 33, wherein treating the array with the set of biological sample removal conditions comprises, sequentially, treating the array with the base, washing the array with the buffer, washing the array with water, and optionally drying the array.

Embodiment 35 is the method of any one of embodiments 16-34, wherein treating the array with the set of biological sample removal conditions further comprises treating the array with a proteinase.

Embodiment 36 is the method of embodiment 35, wherein treating the array with the proteinase precedes treating with the base.

Embodiment 37 is the method of embodiment 35 or 36, wherein the proteinase is proteinase K.

Embodiment 38 is the method of any one of embodiments 35-37, wherein treating the array with the proteinase is for between 10 minutes and 2 hours.

Embodiment 39 is the method of any one of embodiments 35-38, wherein treating the array with the proteinase is for between 30 minutes and 90 minutes.

Embodiment 40 is the method of any one of embodiments 35-38, wherein treating the array with the proteinase is for about 55 minutes to about 65 minutes.

Embodiment 41 is the method of any one of embodiments 35-40, wherein during treatment of the array with the proteinase, the biological sample is incubated at between 40 degrees and 60 degrees Celsius.

Embodiment 42 is the method of any one of embodiments 35-40, wherein during treatment of the array with proteinase, the biological sample is incubated at between 45 degrees to about 55 degrees Celsius.

Embodiment 43 is the method of any one of embodiments 35-42, wherein treating the array with the proteinase further comprises treating the array with a surfactant and a proteinase buffer.

Embodiment 44 is the method of embodiment 43, wherein the surfactant is sodium dodecyl sulfate.

Embodiment 45 is the method of embodiment 43 or 44, wherein the surfactant is present in an amount of about 5% w/v to about 20% w/v.

Embodiment 46 is the method of embodiment 43 or 44, wherein the surfactant is present in an amount of about 8% w/v to about 10% w/v.

Embodiment 47 is the method of any one of embodiments 43-46, wherein the proteinase buffer is Tris.

Embodiment 48 is the method of any one of embodiments 43-47, wherein the proteinase buffer has a concentration of about 1 mM to about 20 mM.

Embodiment 49 is the method of any one of embodiments 43-48, wherein the proteinase buffer has a concentration of about 8 mM to about 12 mM.

Embodiment 50 is the method of any one of embodiments 43-49, wherein the proteinase buffer has a pH of about 8.0 to about 10.0.

Embodiment 51 is the method of any one of embodiments 43-49, wherein the proteinase buffer has a pH of about 8.5 to about 9.5.

Embodiment 52 is the method of any one of embodiments 43-49, wherein the proteinase buffer has a pH of about 8.8 to about 9.2.

Embodiment 53 is the method of any one of embodiments 43-52, wherein treating the array with the set of biological sample removal conditions comprises, treating the array with the proteinease, washing the array with water, treating the array with the base, washing the array with the buffer, washing the array with water, and optionally drying.

Embodiment 54 is the method of any one of embodiments 1-53, wherein the array comprises a slide.

Embodiment 55 is the method of embodiment 54, wherein the slide is a glass slide.

Embodiment 56 is the method of any one of embodiments 1-55, wherein the biological sample is an animal sample.

Embodiment 57 is the method of any one of embodiments 1-55, wherein the biological sample is a human sample.

Embodiment 58 is the method of any one of embodiments 1-55, wherein the biological sample is a rodent sample.

Embodiment 59 is the method of any one of embodiments 1-58, wherein the biological sample is a breast, brain, heart, small intestine, eye, testes, or kidney sample.

Embodiment 60 is the method of any one of embodiments 1-59, wherein the biological sample is a cancerous sample or a sample suspected of having cancerous cells.

Embodiment 61 is the method of any one of embodiments 1-60, wherein the biological sample is a tissue section.

Embodiment 62 is the method of embodiment 61, wherein the tissue section is a fresh frozen tissue section.

Embodiment 63 is the method of any one of embodiments 1-62, wherein the biological sample is fixed.

Embodiment 64 is the method of any one of embodiments 1-63, wherein the biological sample is formalin-fixed.

Embodiment 65 is the method of any one of embodiments 1-63, wherein the biological sample is fixed using methanol.

Embodiment 66 is the method of any one of embodiments 1-63, wherein the biological sample is fixed using acetone.

Embodiment 67 is the method of any one of embodiments 1-66, wherein the biological sample is stained.

Embodiment 68 is the method of embodiment 67, wherein the stain is a histological stain.

Embodiment 69 is the method of embodiment 68, wherein the histological stain is a hematoxylin and eosin stain.

Embodiment 70 is the method of any one of embodiments 1-69, wherein the biological sample is imaged using immunofluorescence.

Embodiment 71 is a method for capturing an analyte using an array, the method comprising:
(a) resetting an array according to any one of embodiments 1-70, wherein the array is a spatial array and the capture probe further comprises a spatial barcode;
(b) contacting the spatial array with a biological sample; and
(c) capturing an analyte from the biological sample on the spatial array.

Embodiment 72 is the method of embodiment 71, wherein the analyte comprises RNA, DNA, a protein, a small molecule, or a metabolite.

Embodiment 73 is the method of embodiment 71 or 72, further comprising determining (i) all or a portion of a sequence corresponding to the spatial barcode, or a complement thereof, and (ii) all or a portion of a sequence corresponding to the analyte, or a complement thereof.

Embodiment 74 is a method for analyzing capture of a plurality of analytes on a tissue optimization array, the method comprising:
(a) resetting a tissue optimization array according to any one of embodiments 1-70;
(b) contacting the tissue optimization array with a biological sample;
(c) capturing a plurality of analytes from the biological sample on the tissue optimization array; and
(d) analyzing the amount, distribution, and/or diffusion of the plurality of analytes based on the analytes from the biological sample captured on the tissue optimization array.

Embodiment 75 is the method of embodiment 74, wherein the plurality of analytes comprises RNA, DNA, a protein, a small molecule, a metabolite, or a combination thereof.

Examples

Example 1—Methods for Removing a Tissue Sample from an Array

Figure 2A:
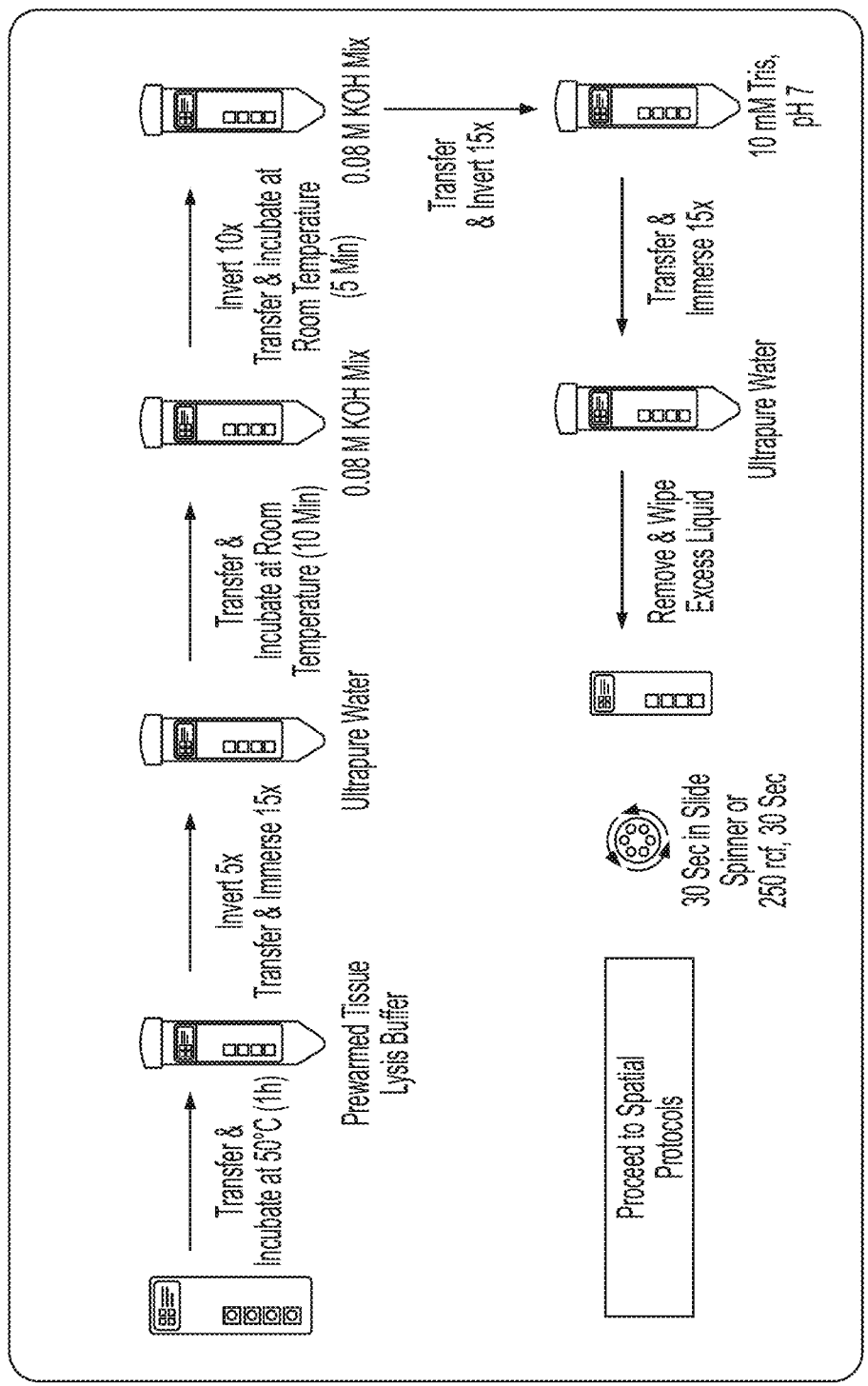
FIG. 2A shows an exemplary workflow for resetting a slide containing multiple arrays.

In a non-limiting example, an array is reset by removing tissue that had been placed the array (FIG. 1), using a variety of reagents and consumables. For examples, tissues that were folded when positioned on the array, tissues that covered fiducial markings, tissues that were torn or otherwise compromised and tissues that were not placed in the correct designated area. The reagents and consumables can include proteinase K, Tris buffer, 20% SDS, potassium hydroxide, and a water bath or heat block that can heat up to 50 degrees Celsius. For example, a method for resetting an array can include: (a) soaking a fixed and stained tissue slice on an array for 1 hour in 30 mL of proteinase K buffer (10 mM Tris, pH 9, 10% SDS, 3.3 mg/mL ProK) at 50° C.; (b) removing the array from the proteinase K buffer and rinsing in nuclease-free water; (c) soaking the array for 10 minutes in 30 mL of 0.08M potassium hydroxide; (d) removing the array and rinsing in 10 mM Tris, pH 7.0; (e) rinsing the array in nuclease-free water; and (f) spinning down or air drying. See, e.g., FIG. 2A for an exemplary workflow.

While tissue removal incubation step (a) may not remove tissue completely and trace amounts of tissue may still remain on the array (FIG. 2B, left), in such instances soaking the array in a basic solution such as 0.08M potassium hydroxide has been shown to remove any remaining tissue (FIG. 2B, right).

Example 2—Methods for Removing a Tissue Sample from an Array

Arrays on a slide are reset prior to tissue permeabilization. When immersing a slide in a solution, the slide is typically completely immersed for about 3 seconds.

Reagent volumes described in this Example can accommodate up to two slides. If resetting two slides, slides are placed back to back so that tissue sections are facing outwards.

A water bath or heat block is preheated to 50° C. to warm 30 mL proteinase K buffer (1 mM Tris, pH 9; 10% SDS, 3.3 mg/mL proteinease K). An array including a tissue sample on a slide is transferred to a 50 mL centrifuge tube containing the warmed proteinase K buffer and incubated for 1 hour at 50° C. The tube is inverted and some tissue may remain on the array. The slide is immersed in ultrapure water. The slide is transferred to a 50-mL centrifuge tube containing 30 mL 0.08M potassium hydroxide (KOH) and incubated for 10 minutes at room temperature. The tube is inverted. The slide is transferred to a new 50 mL centrifuge tube containing 30 mL 0.08 M KOH and incubated at room temperature for 5 minutes. The slide is transferred to a 50 mL centrifuge tube containing 10 mM Tris, pH 7 and inverted slowly. The slide is immersed in fresh ultrapure water. Excess water is removed using a laboratory wipe on the back of the slide, without touching the active surface of the slide. The slide is dried, optionally for 30 seconds in a slide spinner, or in a 50 mL centrifuge tube centrifuged at 250 relative centrifugal force (rcf) for 30 seconds in a swinging bucket rotor.

The slide, and each array within the slide, is examined for any remaining tissue. If tissue remains, the reset protocol above is repeated.

A slide where tissue is removed, thus resetting the slide, can be stored in a sealed container or dessicator at room temperature or at 4° C. for up to 7 days before placing a new tissue section on one or more of the active arrays on the slide.

Example 3—Resetting an Array with a Different Tissue Sample

Figure 3:
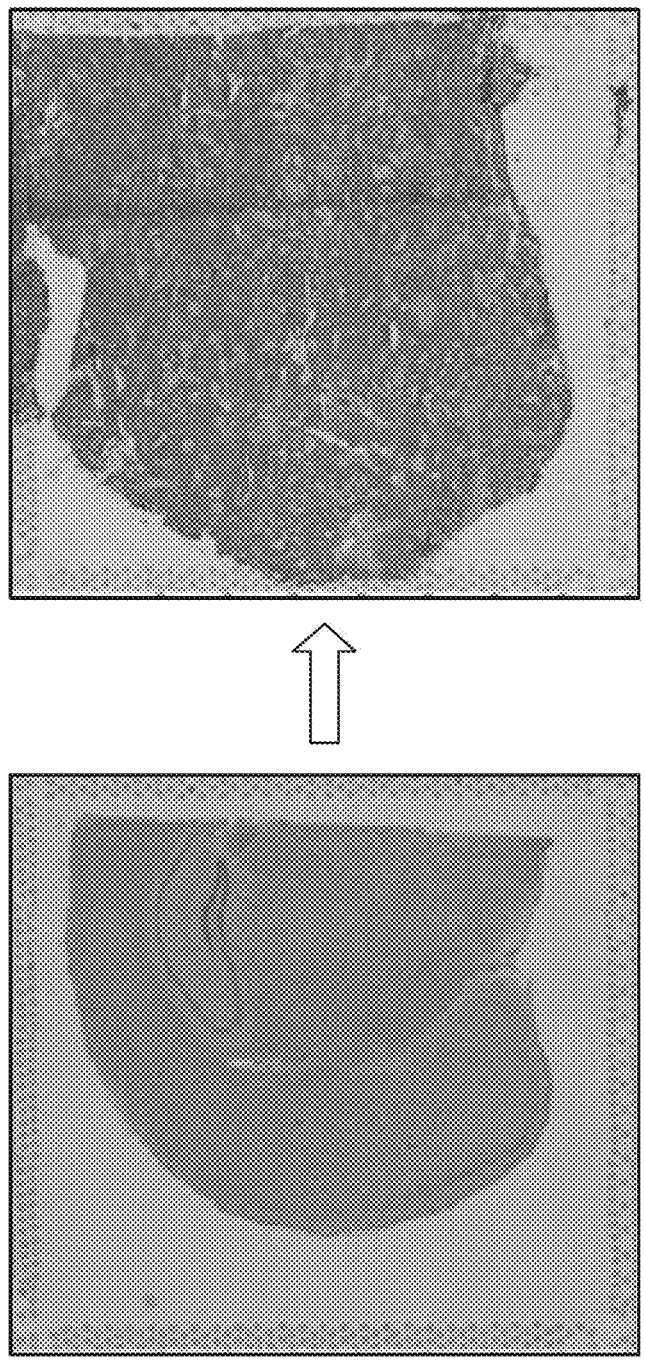
FIG. 3 shows exemplary images of an array originally in contact with mouse brain tissue (left) and the same array after removing the mouse brain tissue and replacing it with a sample of sectioned human ovarian tumor (right).

In a non-limiting example, a tissue sample is removed from an array as described above in Example 1. For this example, the array was originally in contact with mouse brain tissue, wherein the mouse brain tissue was removed, thereby resetting the array and replaced with a section of a human ovarian tumor tissue (FIG. 3).

The mouse brain tissue, which was first stained and imaged (FIG. 3, left panel) and was removed from the array by (a) soaking the fixed and stained tissue slice on the array for 1 hour in 30 mL of proteinase K buffer (10 mM Tris, pH9, 10% SDS, 3.3 mg/mL ProK) at 50° C.; (b) removing the array and rinsing 15 times in nuclease-free water; (c) soaking the array for 10 minutes in 30 mL of 0.08M potassium hydroxide; (d) removing the array and rinsing 15 times in 10 mM Tris, pH 7.0; (e) rinsing the array 20 times in nuclease-free water; and (f) spinning down or air drying the array. A tissue section from a human ovarian tumor was then placed on the same array, stained and imaged (FIG. 3, right panel).

Figure 4:
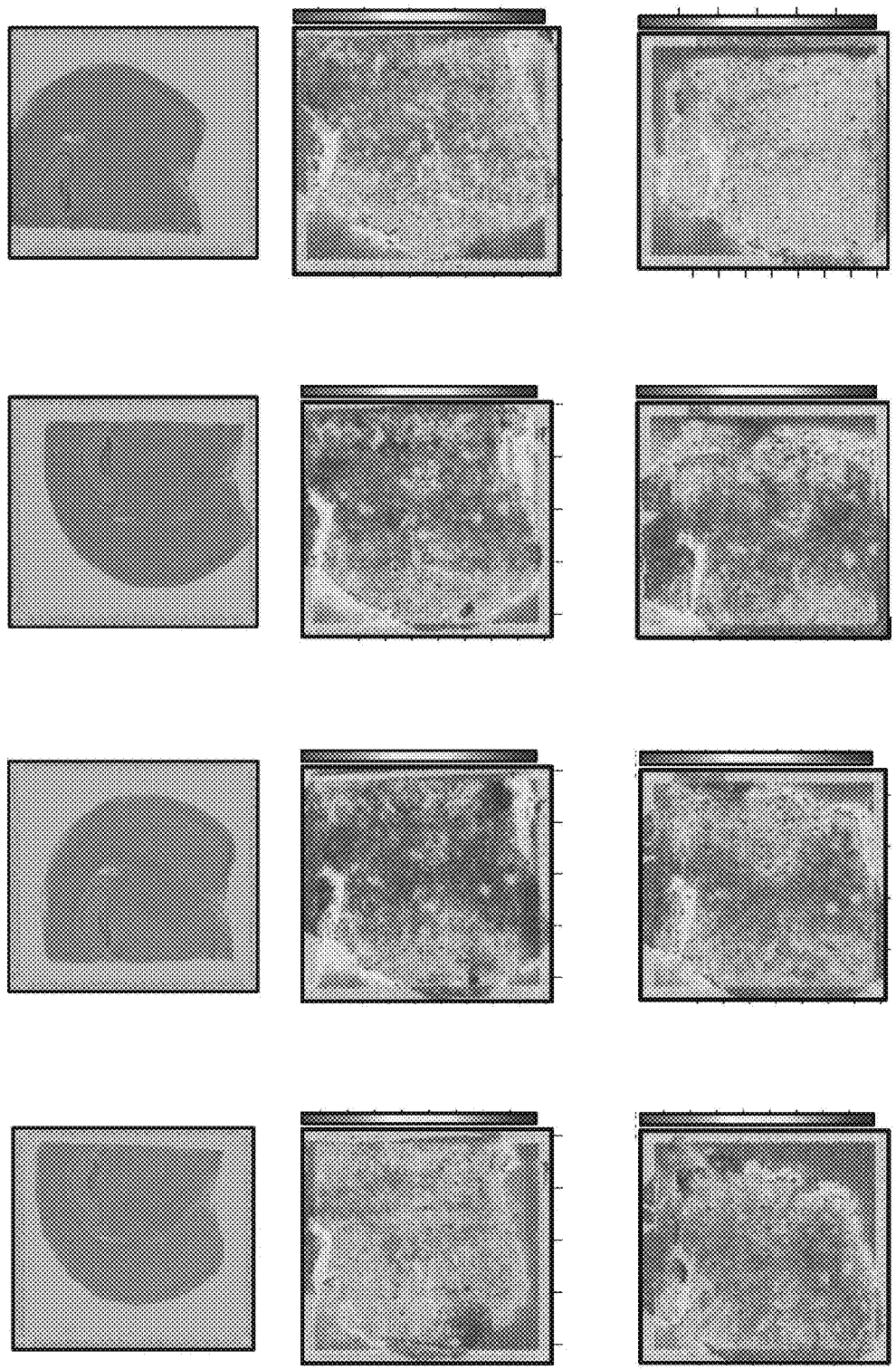
FIG. 4 shows exemplary images of four replicates of reset arrays originally in contact with mouse brain tissue (top row). The middle row shows exemplary imaging results after performing spatial analysis on the replicate arrays after resetting the replicate arrays to remove the associated mouse brain tissue and replacing it with sectioned ovarian tumor tissue. The bottom row shows exemplary control array imaging results after performing spatial analysis on arrays with ovarian tumor tissue, which have not been reset.
Figure 5A:
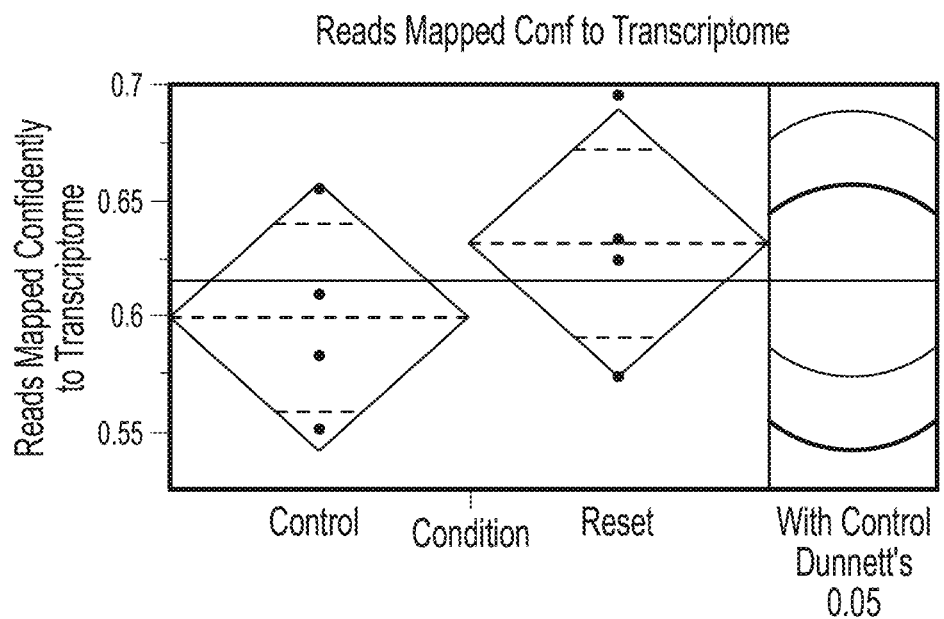
Figure 5B:
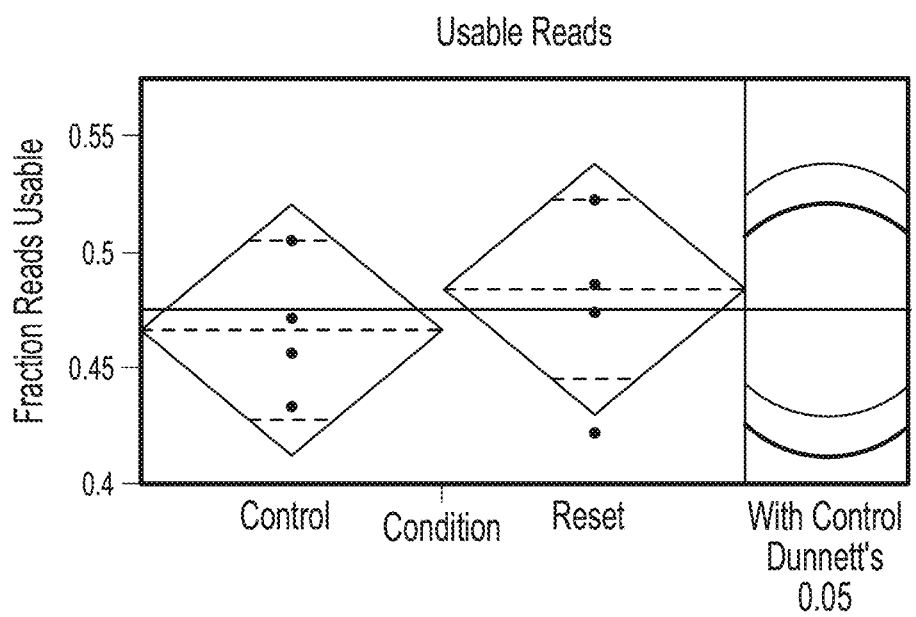
Figure 5C:
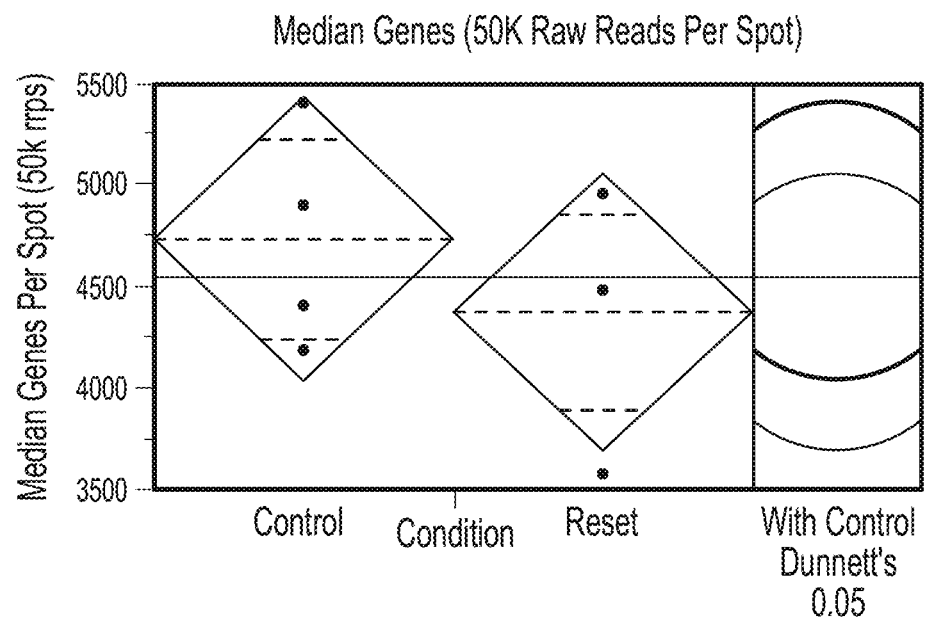
Figure 5D:
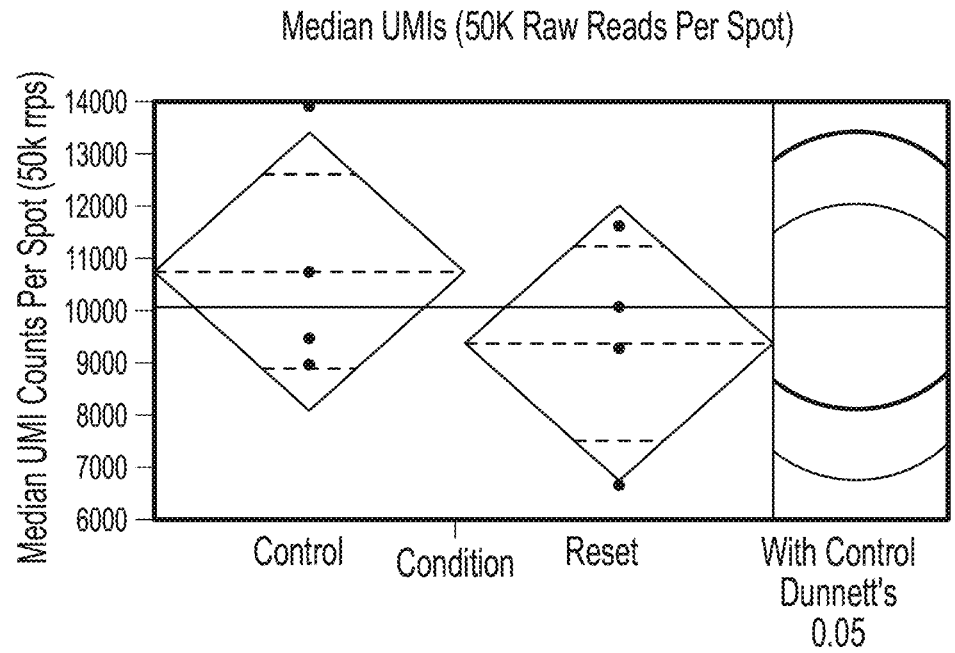

FIG. 4 shows exemplary images of replicate experiments where spatial analysis was performed and analyte gene expression information was obtained. FIG. 4 top row shows four replicates of an array with stained and imaged mouse brain tissue samples. The middle row shows exemplary imaging results after resetting the arrays from the top row by removing the mouse tissues as previously described and replacing the mouse tissue sections with sectioned ovarian tumor tissue followed by spatial analyte analysis of the ovarian tumor tissue samples. The bottom row shows positive control imaging results after performing spatial analyte analysis on ovarian tumor tissue samples that were not reset (i.e., the spatial arrays were new and had not been contacted with tissue prior to the application of the ovarian tumor tissue sections). The reset arrays demonstrate similar spatial analyte data (gene expression intensity) as the control arrays thereby demonstrating negligible or no visible contamination or analyte carry over from the original mouse brain tissue samples to the human ovarian sections on the reset arrays.

FIG. 5A-D show exemplary data analysis and Dunnett's control data demonstrating no significant difference between human ovarian tumor control spatial array analyte determination and that of the reset array data with regards to the A) reads mapped to the human ovarian tumor transcriptome, B) the fraction of usable reads, C) the median of genes per array spot and D) median UMI count per array spot. While there was a slight decrease seen in the median genes and UMIs per spot from the reset arrays vs control arrays (FIGS. 5C and 5D) it was not significant.

The reset array was also compared to a control array for the potential contamination of the HPCA gene. The hippocalcin gene, or HPCA, is highly expressed in the hippocampus region of mouse brain but not in human ovarian tumors. The results shown in FIG. 6A identify the location of the HPCA cluster in mouse brain, HPCA gene expression is not seen in the reset array FIG. 6B (left panel) nor in the control (non-reset) array (right panel). As such, there was no detectable contamination noted on the reset array.

Example 4—Effect of the Reset Protocol on Capture Probes on an Array

Figure 7B:
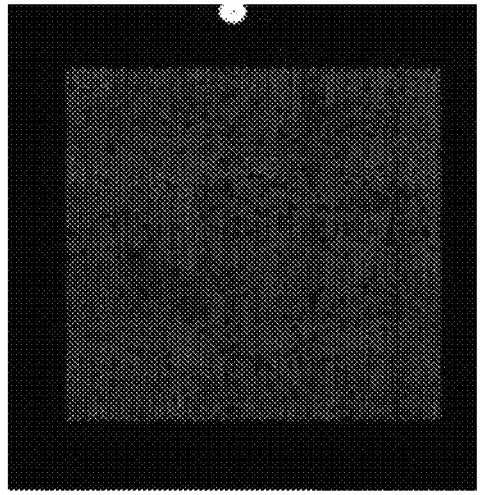
FIG. 7A-G shows imaging results from a reset array (FIG. 7B; previous tissue shown in FIG. 7A), new array (FIG. 7D), followed by hybridizing a Cy3 labeled-partial Read 1 oligonucleotide to the spots, rinsing and imaging the arrays. The negative control array (FIG. 7C) was processed through an entire spatial workflow protocol without any tissue. In the absence of tissue, no gene expression should be detected. Imaging each of the three arrays for 200 milliseconds shows that the overall fluorescence is comparable between the reset array and new array. Both the reset array and the new array demonstrate a similar level of fluorescence (ability to bind the Cy3-partial Read 1 oligonucleotide) as compared to the no tissue, full spatial workflow control array.
Figure 7D:
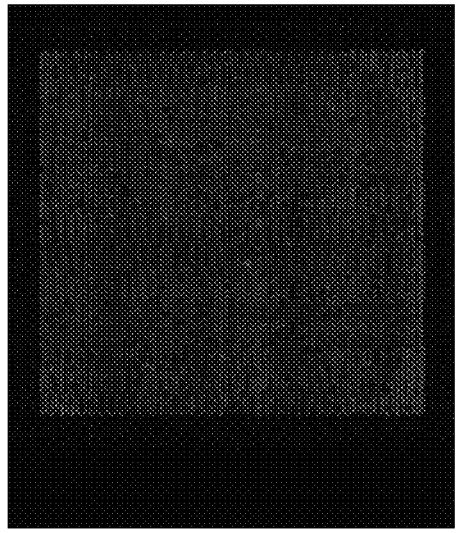
Figure 7A:

In a non-limiting example, experiments were performed to analyze the hybridization of a fluorescently labeled oligonucleotide to the capture probes on three different arrays: (1) an array slide that had fixed and stained tissue on it and was reset, (2) an array that had been processed through the entire spatial analyte localization workflow as described herein, and (3) a new array. An image of the tissue on the control array (which was reset for array (1)) is seen in FIG. 7A.

Figure 7C:
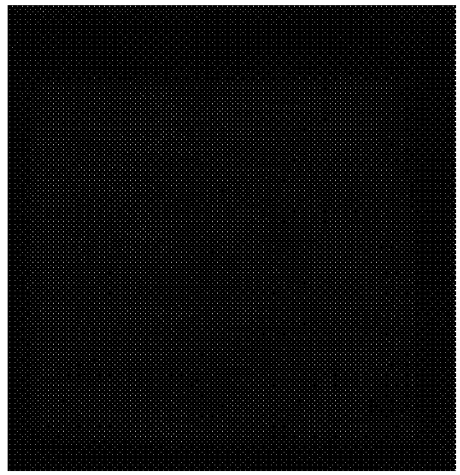

Briefly, the array having fixed and stained tissue was exposed to the previously described reset protocol, and oligonucleotides containing partial Read 1 sequences complexed with Cy3 fluorescent moieties were hybridized to the array. The fluorescently labeled oligonucleotides were also hybridized to the array that had been processed through the entire spatial analyte detection workflow (lacking tissue), as well as a new array. Fluorescent imaging results from the reset array (FIG. 7B) which was processed using the reset protocol, and a new array (FIG. 7D), hybridized to Cy3 labelled-partial Read 1 oligonucleotides applied to the arrays, rinsed, and imaged demonstrates that the partial Read 1 portion of the oligonucleotide hybridized to its complementary region on the capture probe on the array. Imaging the three arrays for 200 miliseconds (ms) show that overall fluorescence from the locations of the capture probes are comparable between the reset array and new array. Both the reset array and the new array demonstrate a similar level of fluorescence (ability to bind the Cy3-partial Read 1) as compared to the array that was processed according to the spatial workflows described herein (FIG. 7C). The negative fluorescence of the spatial workflow slide provides evidence that once the spatial workflow involving enzymatic actions such as, for example, reverse transctiption of mRNA analytes, slide reset is not possible using the tissue removal conditions described in the prior examples.

Figure 7E:
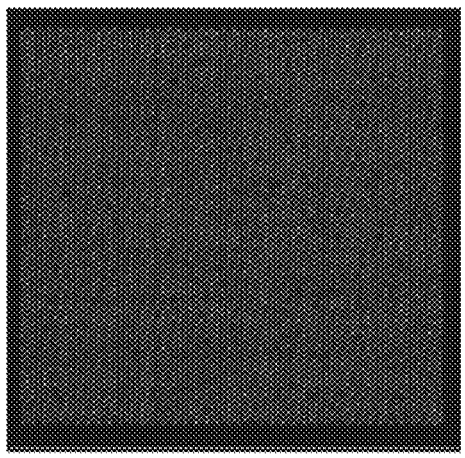
Figure 7F:
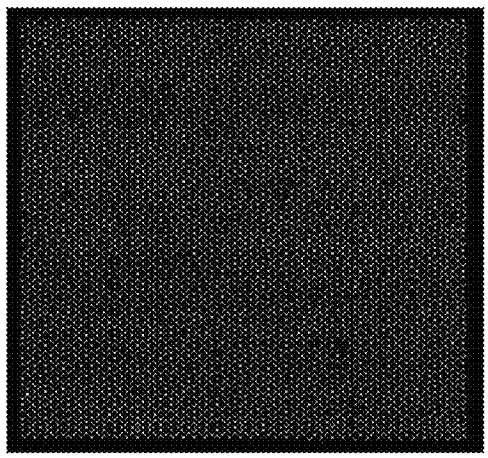
Figure 7G:
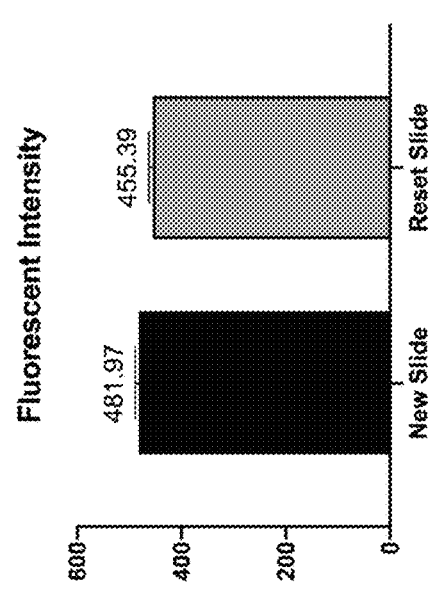

In experiments to demonstrate the affect of the reset methods on probes affixed to the array slide, blocks of OCT medium without tissue were created and slices places on spatial array slides. Some slides were reset (FIG. 7E) and some were not (FIG. 7F, control slides), after which Cy3 labelled-Read 1 oligos were applied to the arrays and binding of the labelled oligos to the probes on the arrays were measured via fluorescence. FIG. 7G demonstrates that the fluorescence intensity of the reset versus the control new (non-reset) slides was comparable, as such the oligos on the array slides were not adversely affected by the reset protocol.

Example 5—Fixation Analysis

Figure 8:
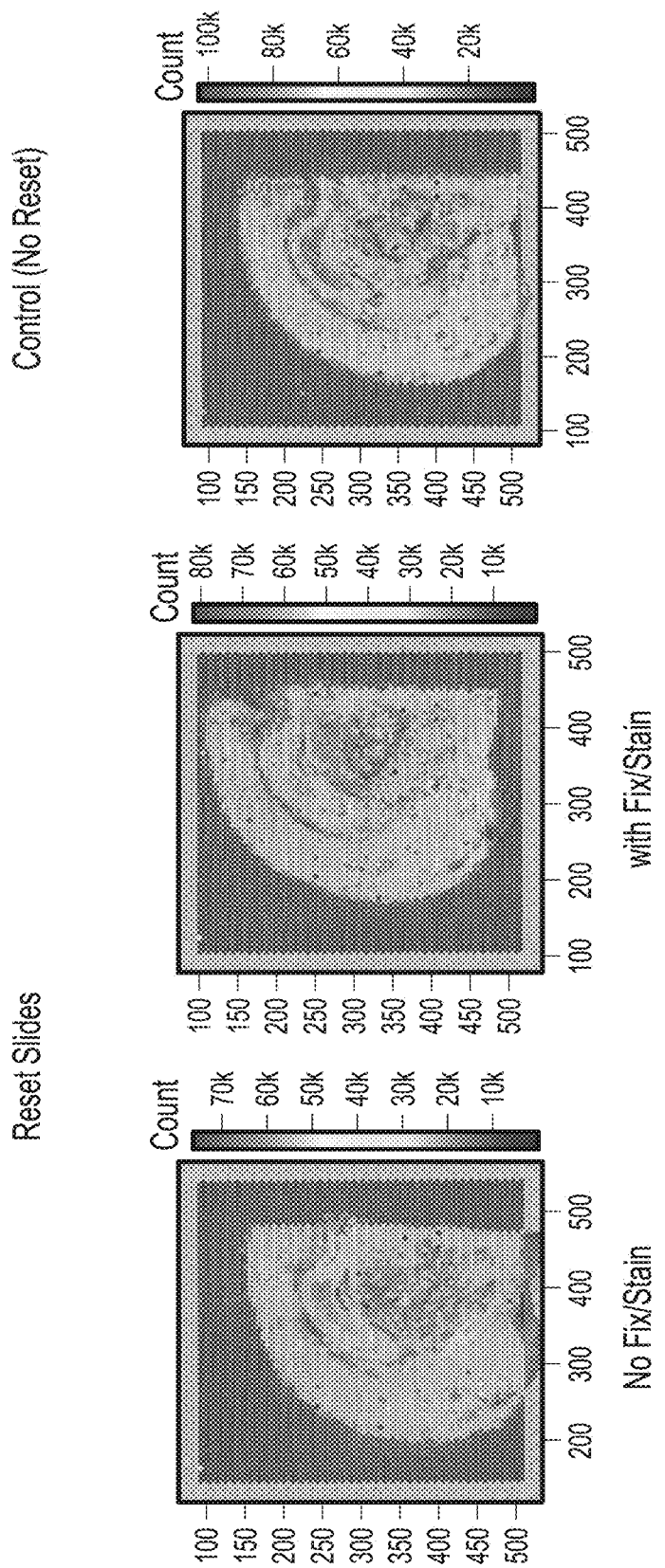
FIG. 8 shows gene expression intensity results for reset arrays when comparing an unstained and unfixed tissue sample (left) to a fixed and stained tissue sample (middle). The control array is an array not previously contacted with tissue (e.g., new array) UMI counts were similar between arrays that were reset with fresh frozen tissue (left), fixed and stained tissue (center), and an array that was not reset (right).

Reset arrays can be used with both fixed and stained tissue as well as fresh frozen cryostat tissue sections. Breast cancer tissue was originally applied to a spatial array (exemplary tissue shown in FIG. 9A). The array was reset, and coronal mouse brain sections, either fixed and stained or fresh frozen sections, were applied to the reset arrays (FIG. 8). The reset array on the left of FIG. 8 shows exemplary imaging results after performing spatial analysis on a cryosectioned tissue that had not been fixed or stained but was reset and mouse brain reapplied to the reset slide. The reset array in the middle image of FIG. 8 shows exemplary imaging results after performing spatial analysis on a fixed and stained mouse brain section after resetting the array. The control array on the right of FIG. 8 shows exemplary imaging results after performing spatial analysis of a brain section on a slide that has not been reset. The UMI counts for tissue sections on the reset arrays are similar to the control section on the new array.

Figures 9A, 9B, 9C:
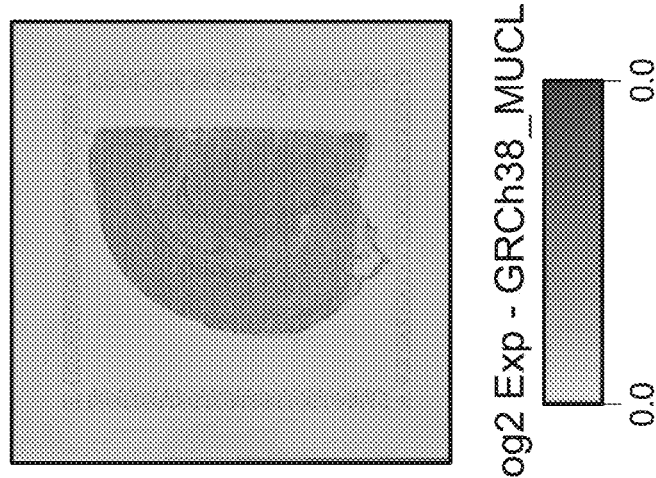
FIG. 9A-C shows FIG. 9A) gene expression of MUCL1, a gene highly expressed in an exemplary human breast cancer tissue section.

MUCL1 is a gene highly expressed in human breast cancer tissue (exemplary expression shown in FIG. 9A). The biological sample removal conditions reduced MUCL1 gene expression when 1 KOH wash was used to reset the slide following removal of the original breast cancer tissue (FIG. 9B), and no MUCL1 expression was observed when 2 KOH washes were used to reset the slide following removal of the original breast cancer tissue (FIG. 9C).

Figure 10A:
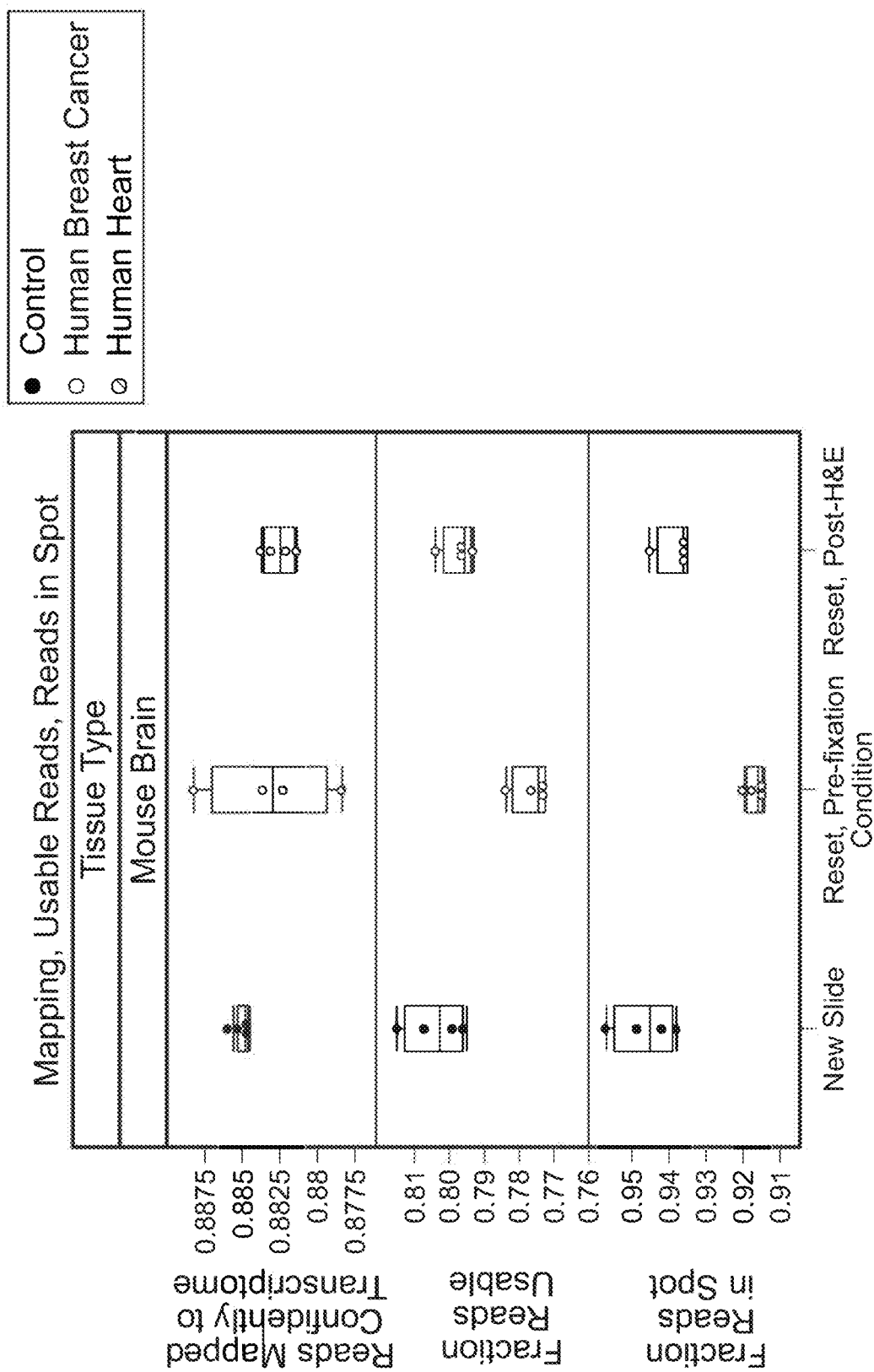
Figure 10B:
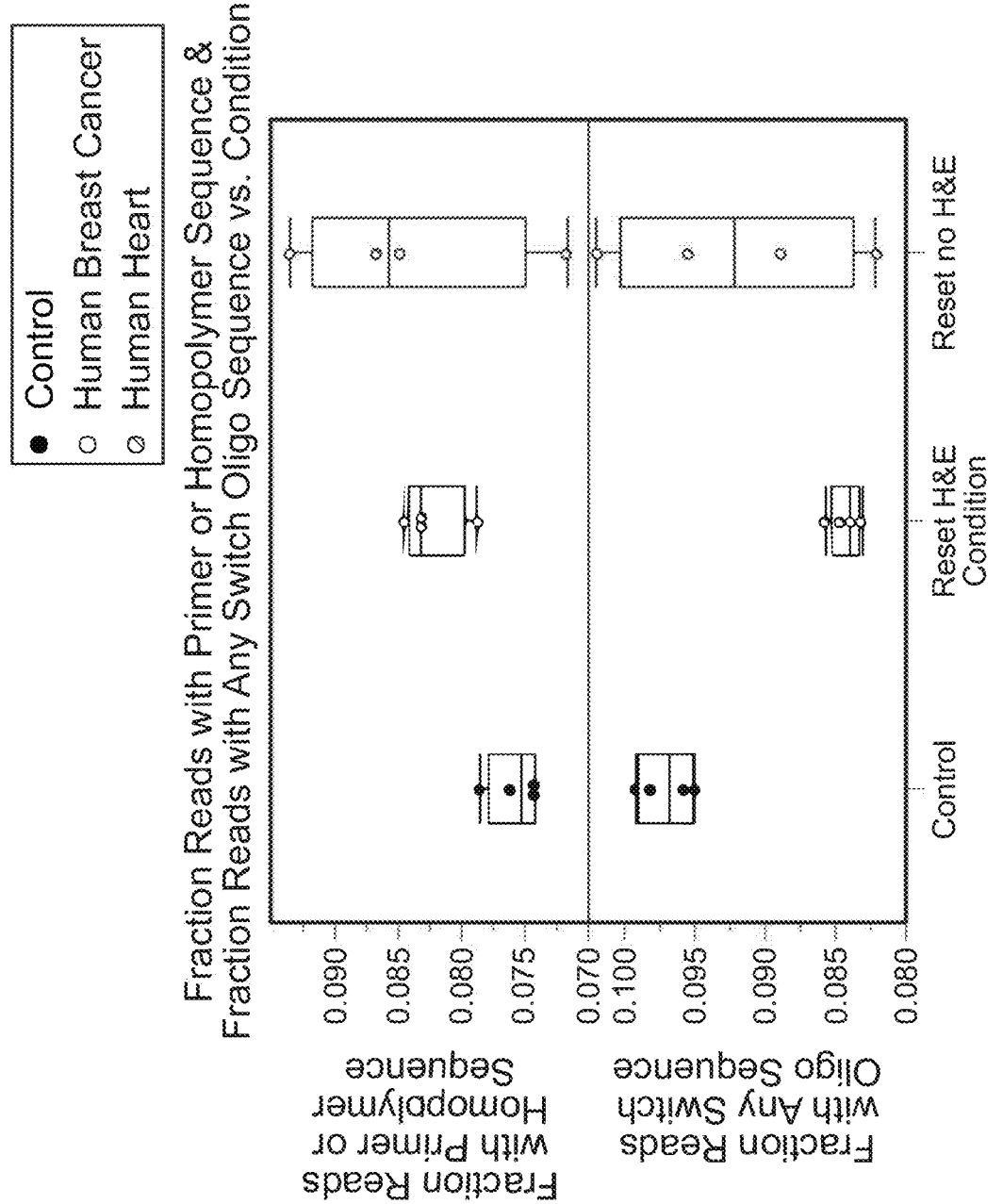
Figure 10C:
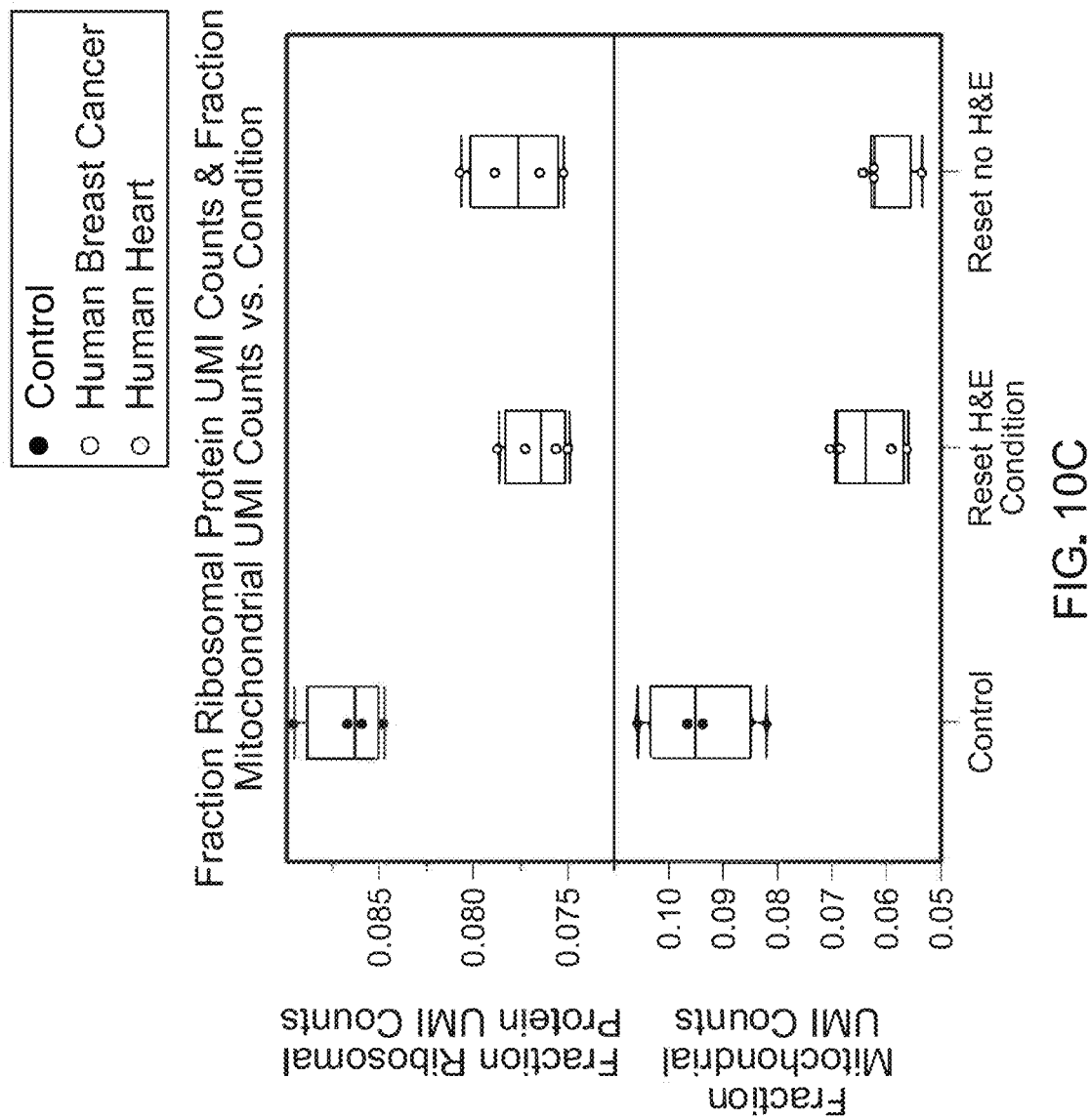
Figure 10D:
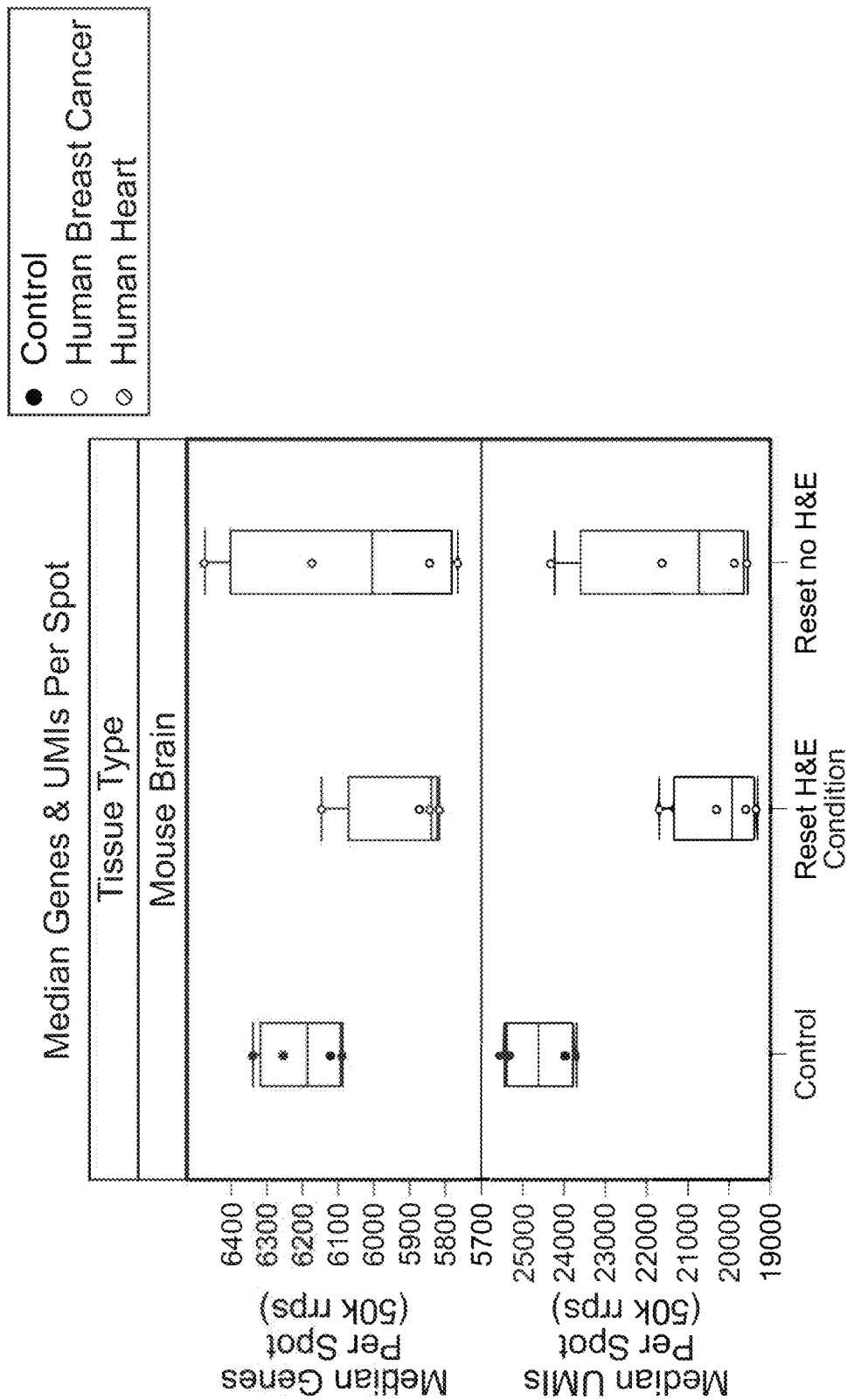
Figure 10E:
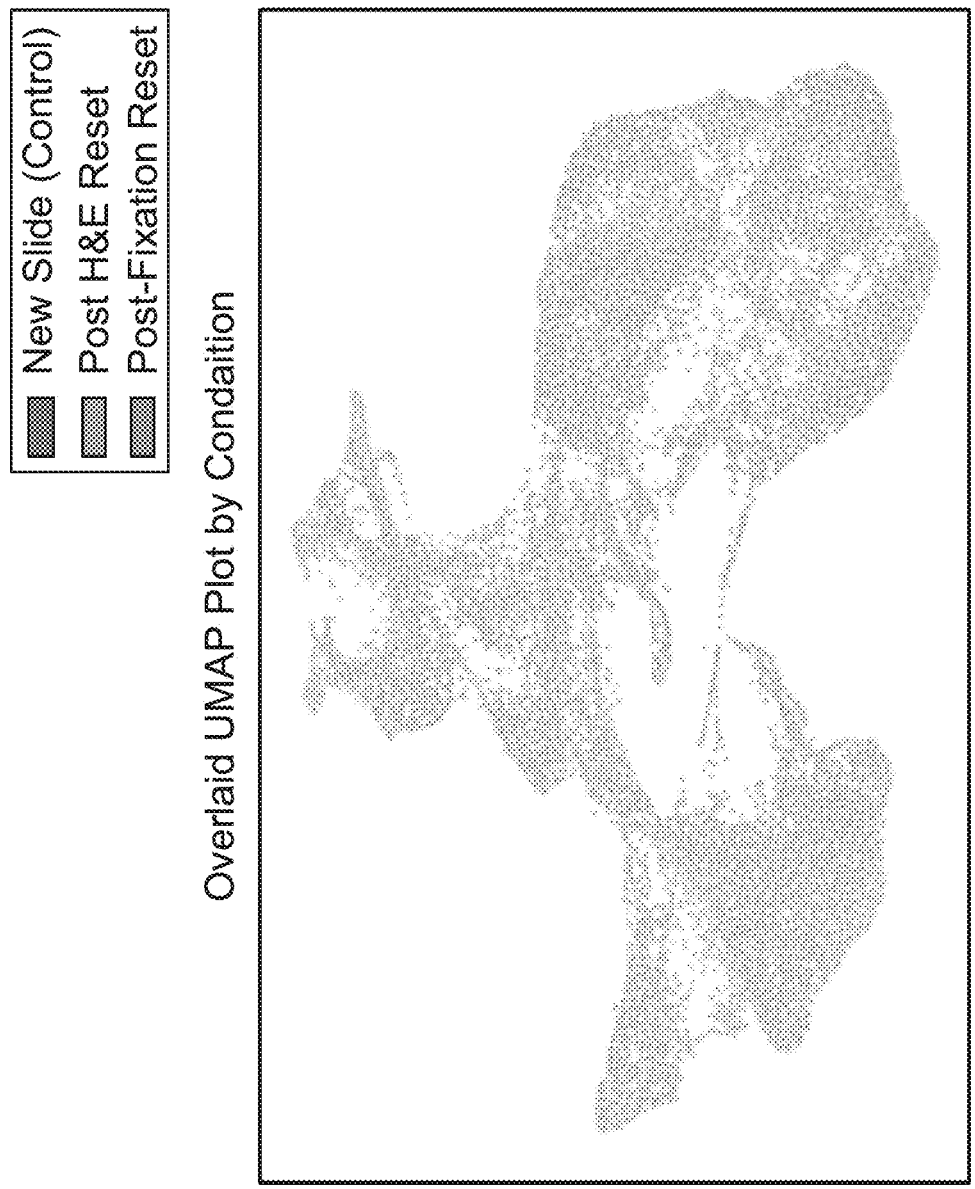

Similarly, when a mouse brain tissue section was applied to a spatial array, the array was reset, and human breast cancer or human heart tissue sections (either fixed and stained or fresh frozen tissue samples), were applied to the reset arrays. Various sequencing metrics were analyzed. FIGS. 10A-D show box plots of control mouse brain data compared to the reset arrays having human breast cancer or human heart tissue sections on the arrays, with regard to A) library quality, B) fraction reads with primer, homopolymer, or switch oligo sequence, C) fraction reads with ribosomal or mitochondrial UMI counts, and D) sensitivity. In FIG. 10A, the mapping was very consistent between the control and reset slides. In FIGS. 10B-C, the fraction reads with primer or homopolymer sequence, or any TSO oligo sequence, as well as the fraction ribosomal protein UMI counts and fraction mitochondrial UMI counts were consistent between reset and control slides. In FIG. 10D, there was no significant difference in median genes in the reset arrays (either fixed and stained or not) and the control arrays, though there was a slight drop in median UMIs for reset slides (about 18% and about 13% for fixed and stained and non-fixed and stained, respectively). The fixed and stained tissue sections and the fresh frozen tissue sections performed about equally on reset arrays. In FIG. 10E, overlaid UMAP plots are shown for mouse brain sections analyzed on a new non-reset array and reset arrays (either fixed and stained or not). In FIG. 10F, analysis of HPCA is shown for mouse brain sections on a new non-reset array and reset arrays (either fixed and stained or not); in the upper figures, H&E staining is shown, with a box around the hippocampal region, and in the lower figures, gene expression analysis is shown, focused on the boxed hippocampal region. The data in FIGS. 10A-F demonstrate that the reset arrays are equally sensitive as a control non-reset array with respect to the fraction of usable reads. There was no significant difference in median genes between reset (pre-fixation or H&E) and control arrays, though there was a slight decrease in median UMIs for the reset arrays.

Example 6—Immunofluorescence Analysis

Figure 11A:
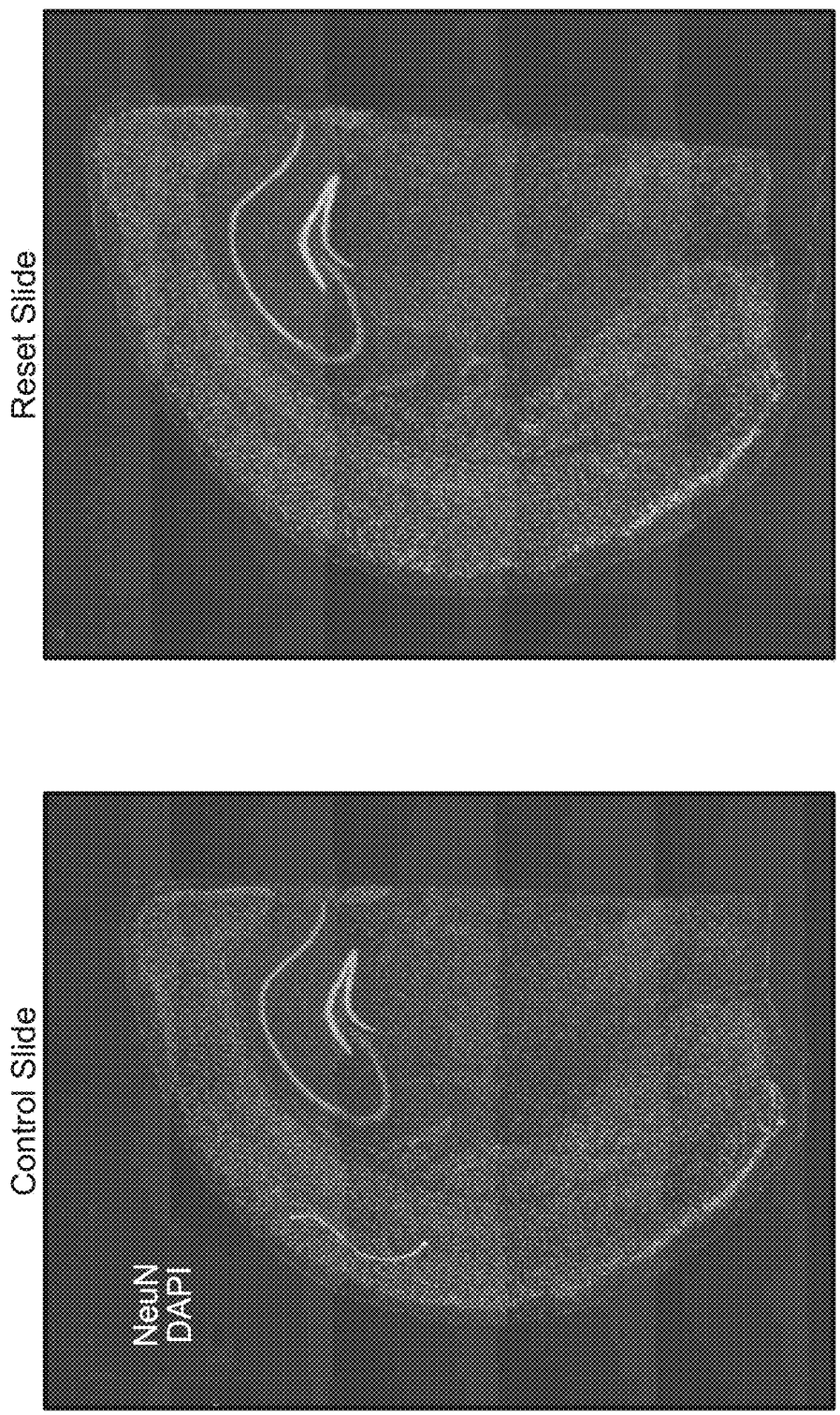
FIG. 11A-G show analysis of immunofluorescence staining on array reset with regard to FIG. 11A) immunofluorescence imaging, FIG. 11B) UMI count, FIG. 11C) library quality, FIG. 11D) contamination of primers in the library, and FIG. 11E) sensitivity.

Resetting arrays is compatible with use of immunofluorescence, both before reset, and when using a new biological sample on an array. Human breast cancer tissue was initially placed on a spatial array and stained with DAPI, an Alexa 647-conjugated anti-CD3 antibody (Biolegend), and an Alexa 488-conjugated anti-CD8 antibody (Biolegend). The array was reset as described in Example 1, and a mouse brain tissue sample was placed on the reset array. The mouse brain tissue was stained with DAPI, an Alexa 555-conjugated anti-NeuN antibody (Abcam), and a FITC-conjugated anti-GFAP antibody (Abcam). There was no difference observed in immunofluorescence images of the reset array (FIG. 11A, left) and a non-reset array (control) having mouse brain tissue stained the same way (FIG. 11A, right).

Figure 11B:
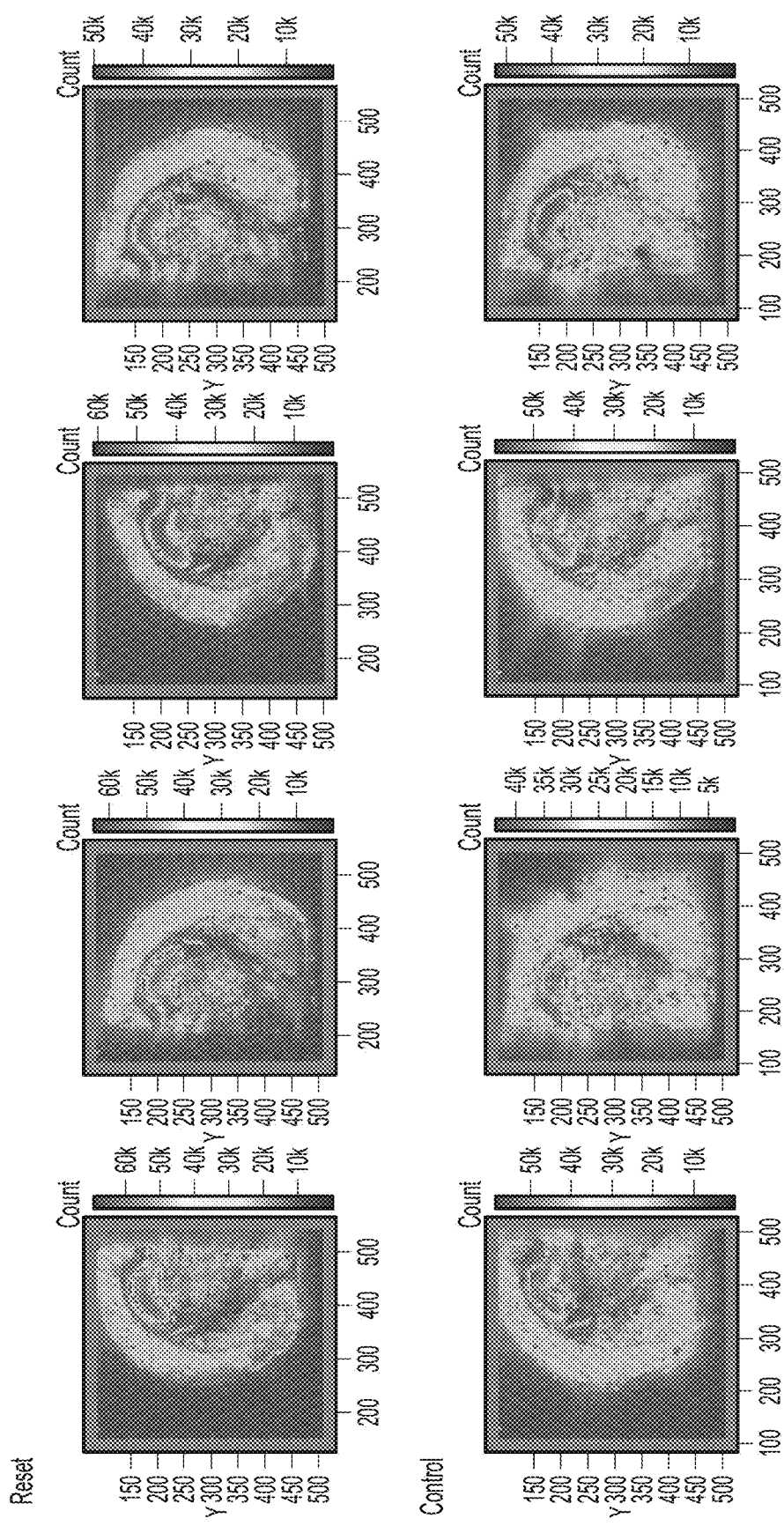
Figure 11C:
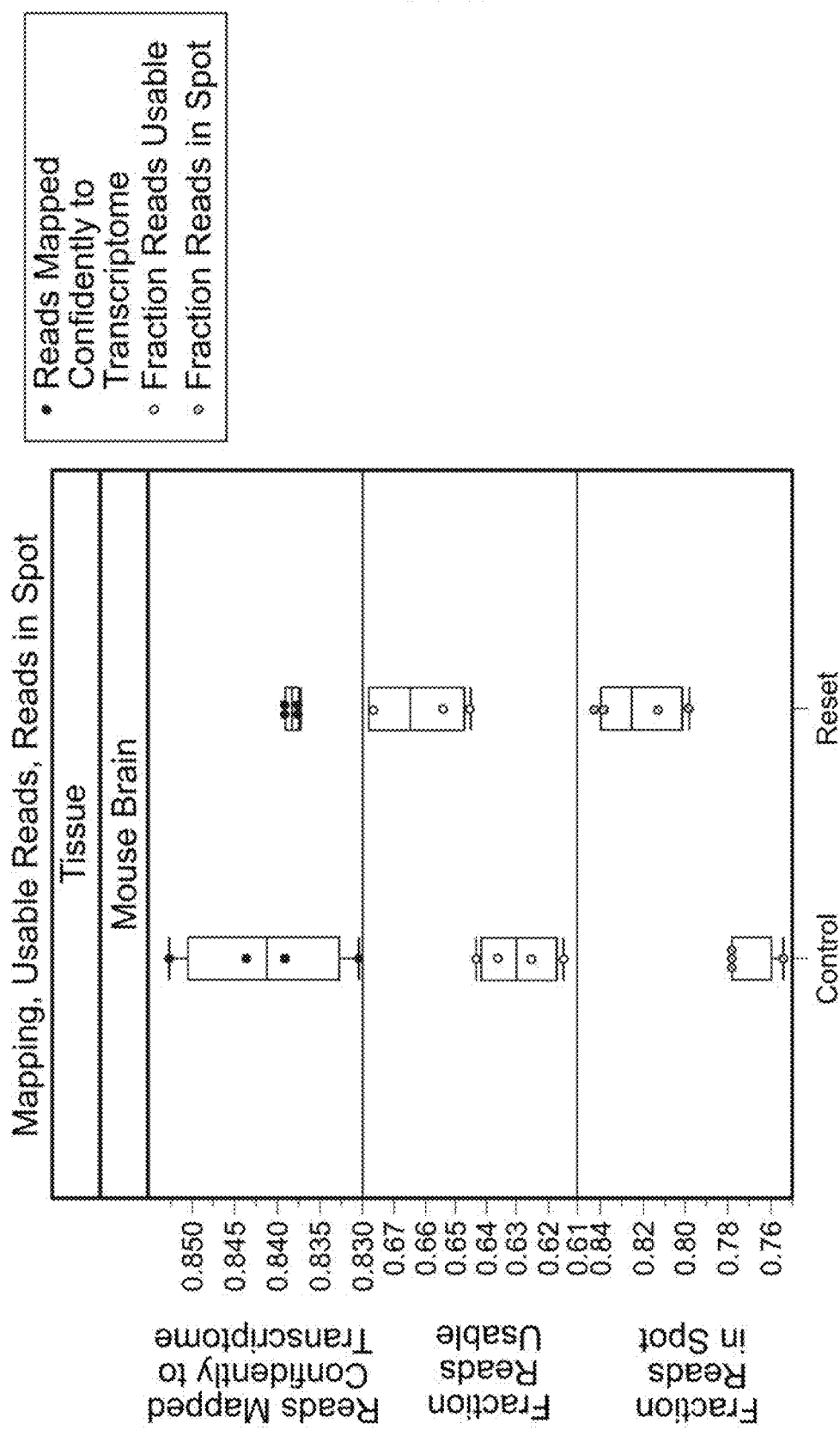
Figure 11D:
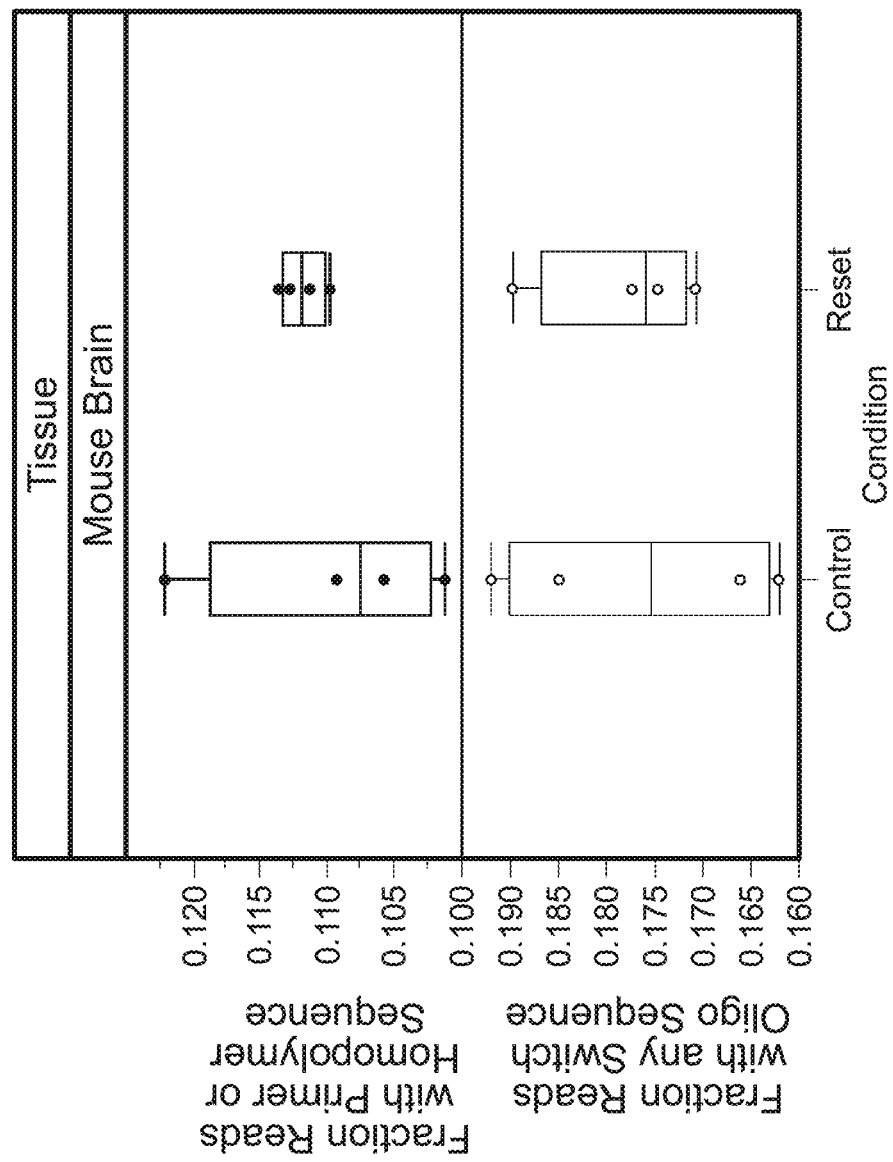
Figure 11E:
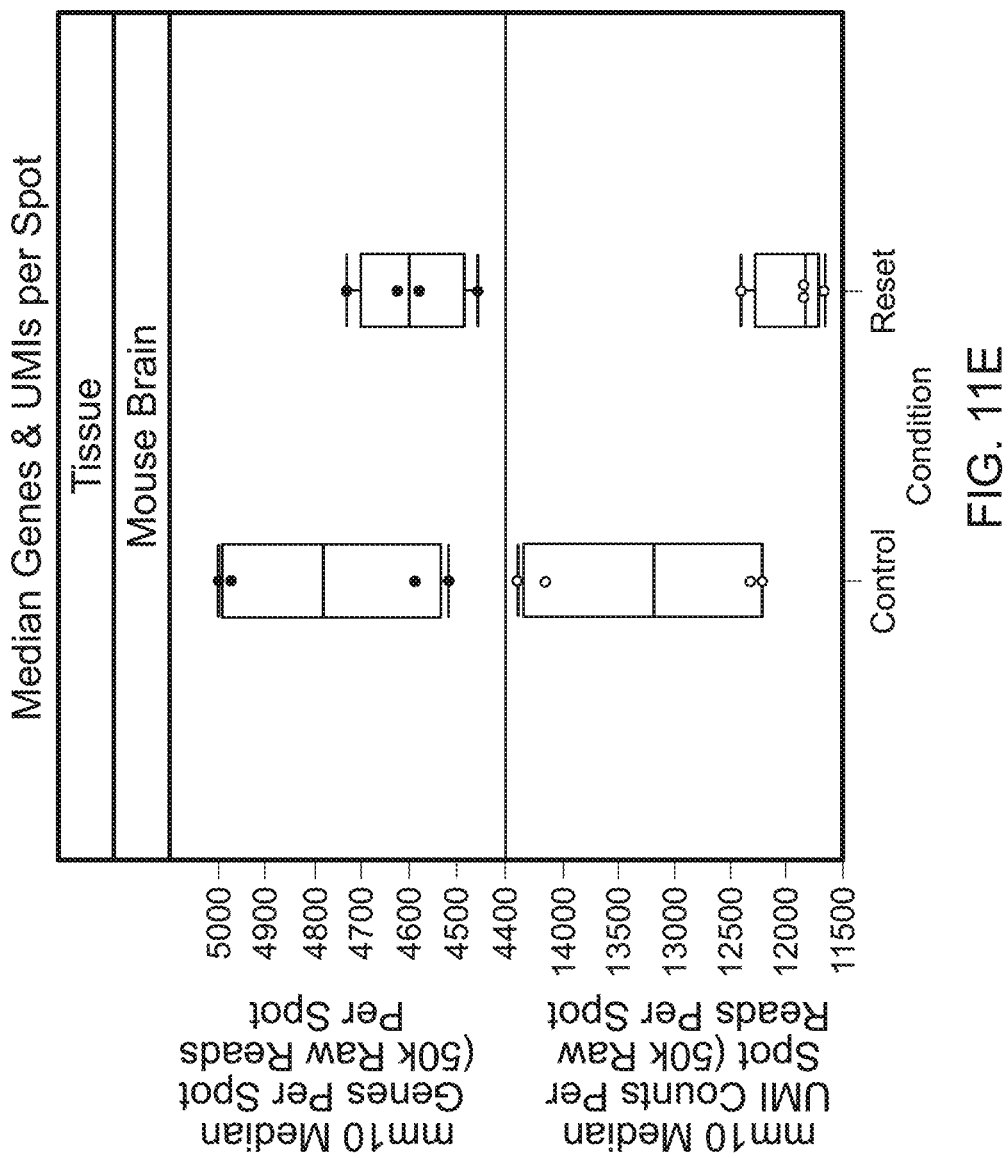
Figure 11G:
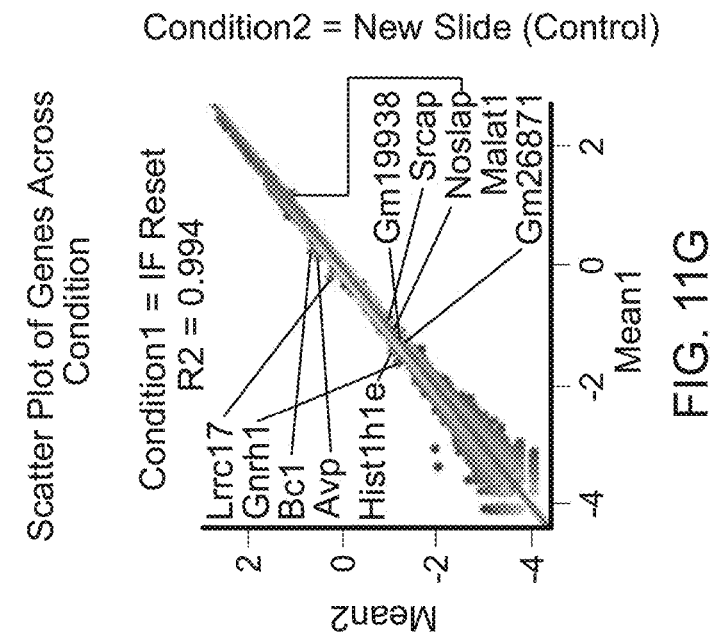
Figure 11F:
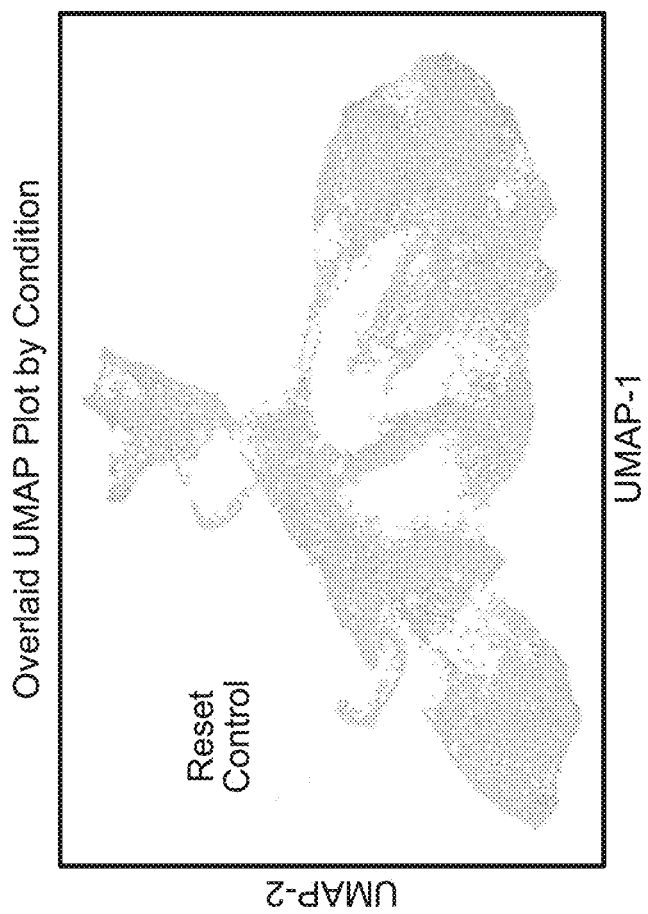

Transcript capture and sequencing metrics of the reset array were similar to the control array following removal of an IF-stained biological sample. FIG. 11B shows that the UMI count appears similar between reset (top row) and control (bottom row) of replicate samples, with a potentially visible decrease of UMI counts in the reset slides. FIGS. 11C-E show box plots of mouse brain tissue on control slides and mouse brain tissue on slides that previously had IF-stained biological samples on them, were reset, and a mouse brain sample placed on the reset array: C) library quality, D) contamination of primers in the library, and E) sensitivity. In FIG. 11C, the metrics for mapping, usable reads, and fraction of reads per spot were very comparable between the control sample (on a non-reset array) and a sample on a reset array. In FIG. 11D, the metrics for homopolymer or template switching oligonucleotide (TSO) were very comparable between the control sample (on a non-reset array) and a sample on a reset array. In FIG. 11E, no significant difference was observed in median genes between the control sample (on a non-reset array) and a sample on a reset array, though a slight decrease was observed in the number of UMIs detected for the sample on a reset array compared to the control sample (on a non-reset array). In FIG. 11F, overlaid UMAP plots are shown for the reset and non-reset (control) arrays. In FIG. 11G, a scatter plot of gene expression is shown. Both UMAP and scatter plot data demonstrate good correlation between the reset and non-reset (control) arrays. The data in FIGS. 11A-G demonstrate that the reset array provided for similar imaging, library quality and UMI counts as compared to a non-reset array.

Example 7— Multiple Resets

It was determined through experimentation that arrays could be reset multiple times without compromising the array capture probes. A mouse brain tissue sample was evaluated on arrays that had been reset one, two, or three times as in Example 1 and compared to a mouse brain tissue sample on a non-reset array (control). The first tissue set on the arrays was a human breast cancer tissue. The arrays were reset, and for the twice and three-times reset arrays, a human lung tissue sample was placed on the array. The arrays were reset, for the three-times reset array, a human cerebellum tissue sample was placed on the array. The array was reset. All slides were fixed with methanol and stained with hematoxylin and eosin.

Figure 12A:
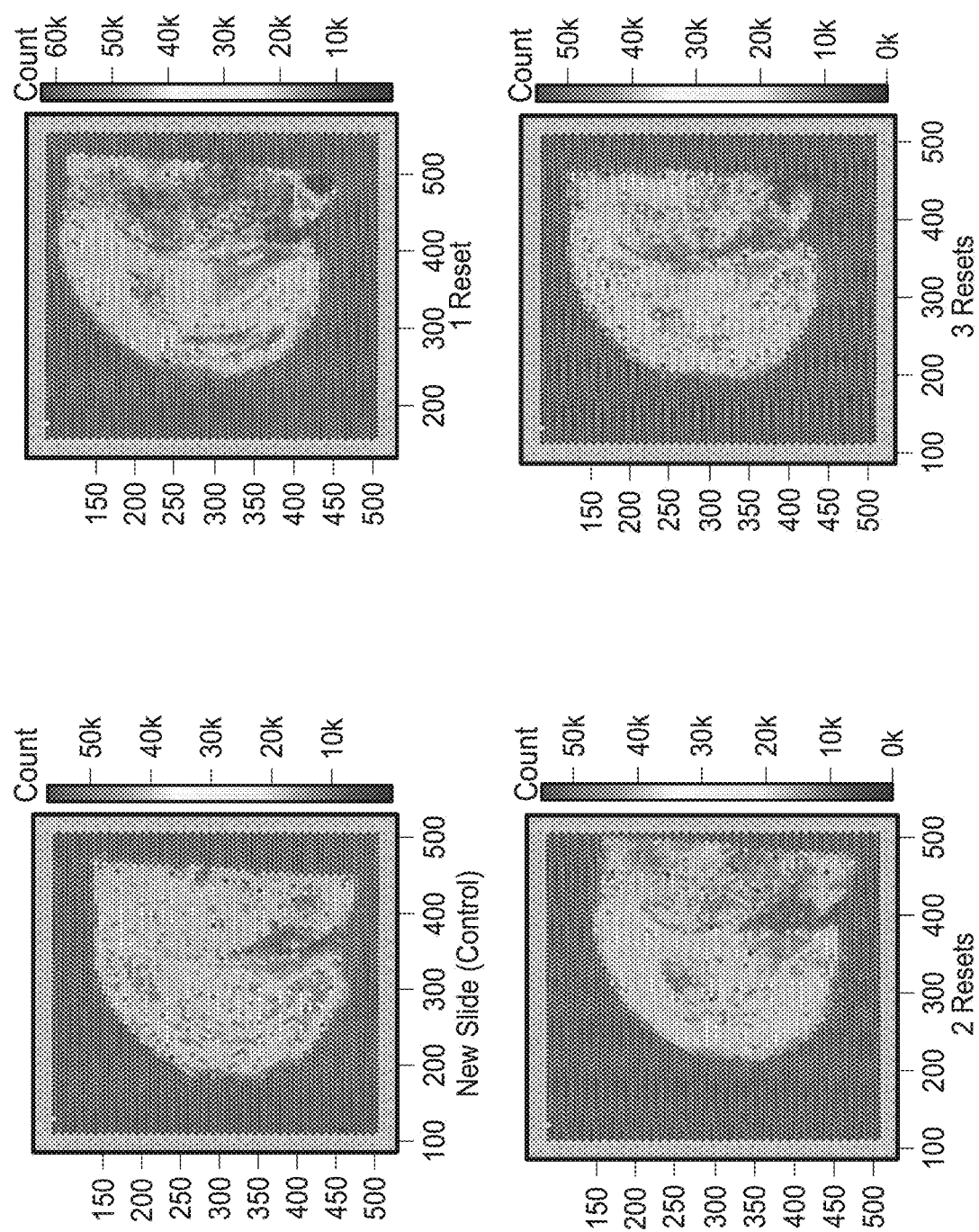
FIG. 12A-D show the effect of resetting an array multiple times with regard to FIG. 12A) UMI count, FIG. 12B) library quality, FIG. 12C) contamination of primers in the library, and FIG. 12D) sensitivity.
Figure 12B:
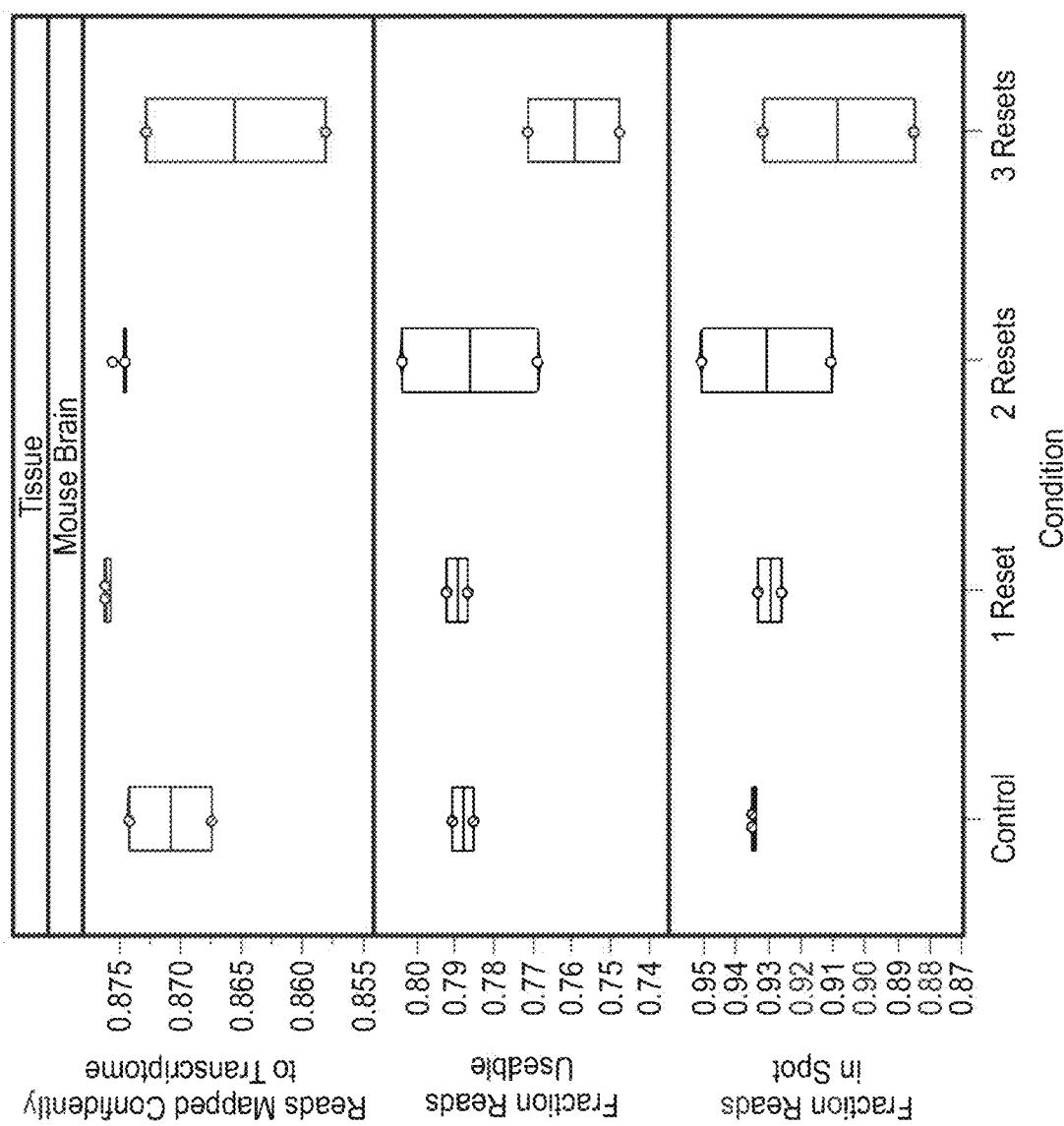
Figure 12C:
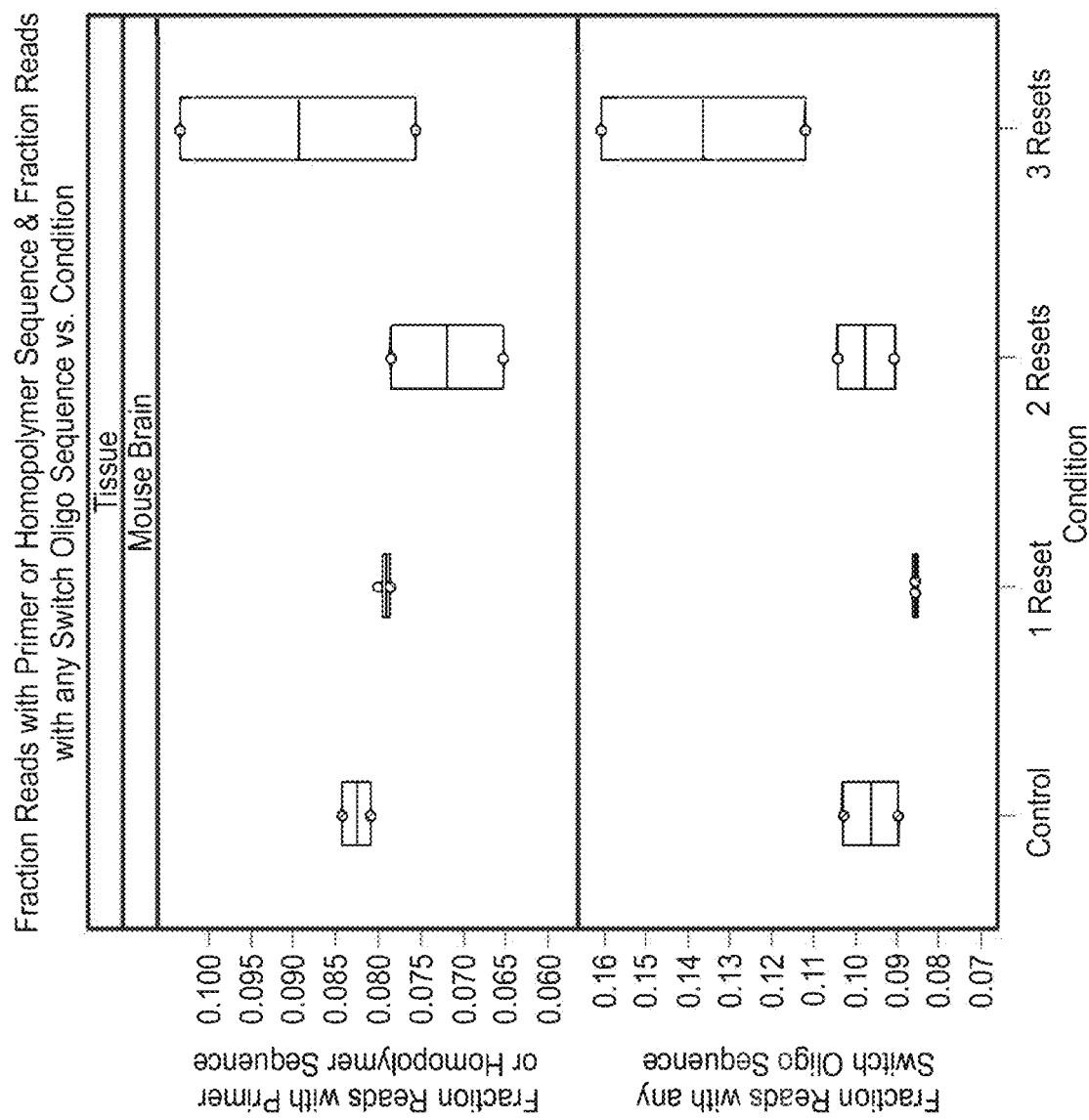
Figure 12D:
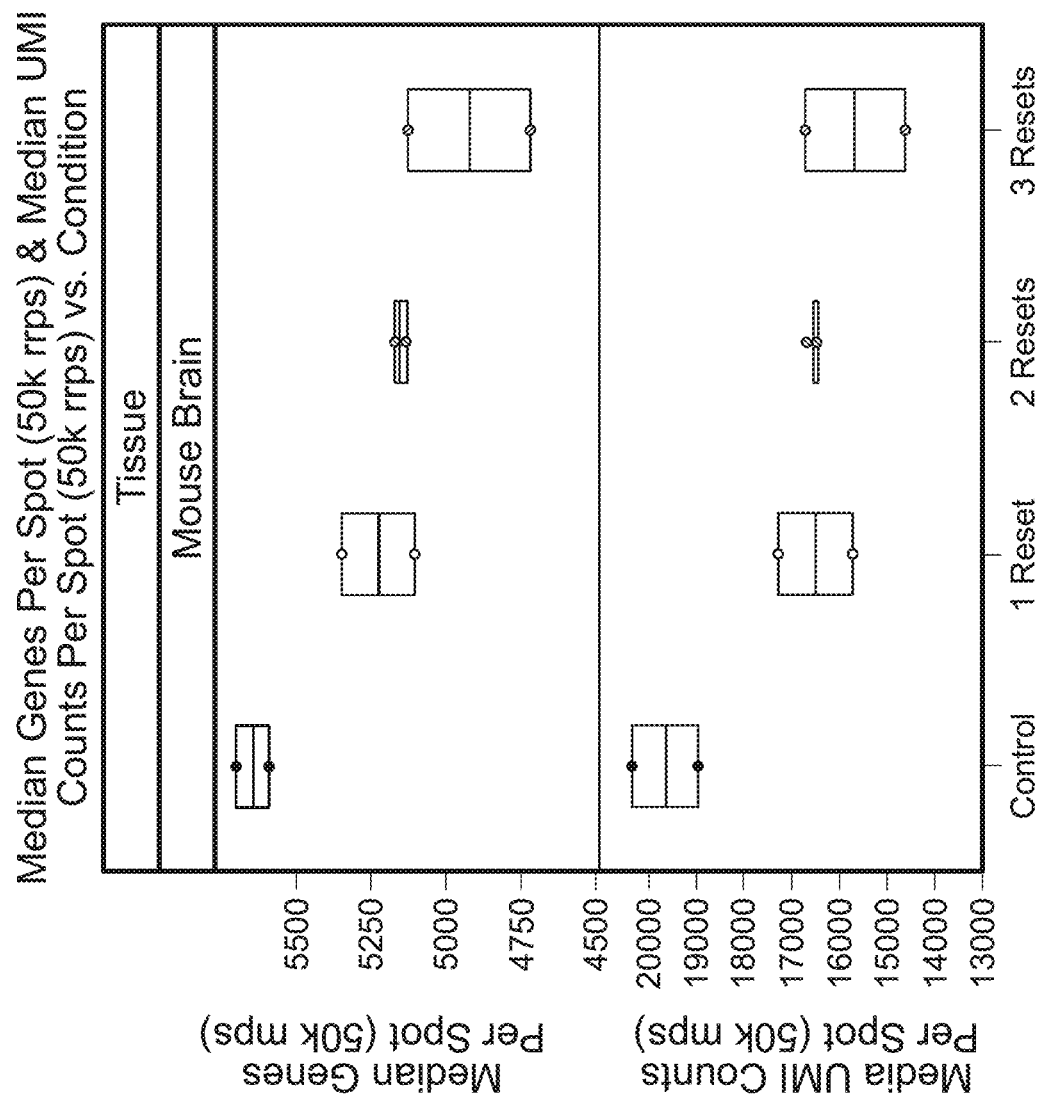

Transcript capture and sequencing metrics of the reset arrays were similar to control following multiple resets. FIG. 12A shows that the UMI count appears similar for the control and multiple-reset samples, with a potentially visible decrease of UMI counts in the reset slides. FIGS. 12B-D show plots of mouse brain tissue on control slides and mouse brain tissue on slides that had been reset one, two, or three times: B) library quality, C) contamination of primers in the library, and D) sensitivity. In FIG. 12B, the metrics for mapping, usable reads, and fraction of reads per spot are very comparable between the control sample (on a non-reset array) and samples on reset arrays. In FIG. 12C, the metrics for homopolymer or template switching oligonucleotide (TSO) are very comparable between the control sample (on a non-reset array) and samples on reset arrays. In FIG. 12D, no significant difference was observed in median genes between the control sample (on a non-reset array) and samples on reset arrays, though a slight decrease was observed in the number of UMIs detected for the sample on reset arrays compared to the control sample (on a non-reset array). In sum, FIGS. 12A-D demonstrate that an array can be reset one or more times without substantially impacting library quality, UMI count, and sensitivity.

Example 8— Effect of Array Reset on Analyte Capture

Resetting arrays can be performed on tissue optimization arrays, for example, for determining conditions for permeabilization and/or analyte capture following removal of a first biological sample. Three tissues were tested for the effect of reset on permeabilization of the second biological sample and/or the capture of transcripts therefrom on non-spatially barcoded (i.e., tissue optimization) arrays: mouse brain, mouse liver, and mouse spleen. In each case, the arrays initially had human lung tumor samples covering the entire capture area of the arrays, and the slides were reset as in Example 1, and the new tissues were placed on the slide, stained with H&E, permeabilized, and the transcripts were captured. Capture was evaluated by fluorescence microscopy of reverse-transcribed cDNA using fluorescent nucleotides.

Figures 13A, 13B:
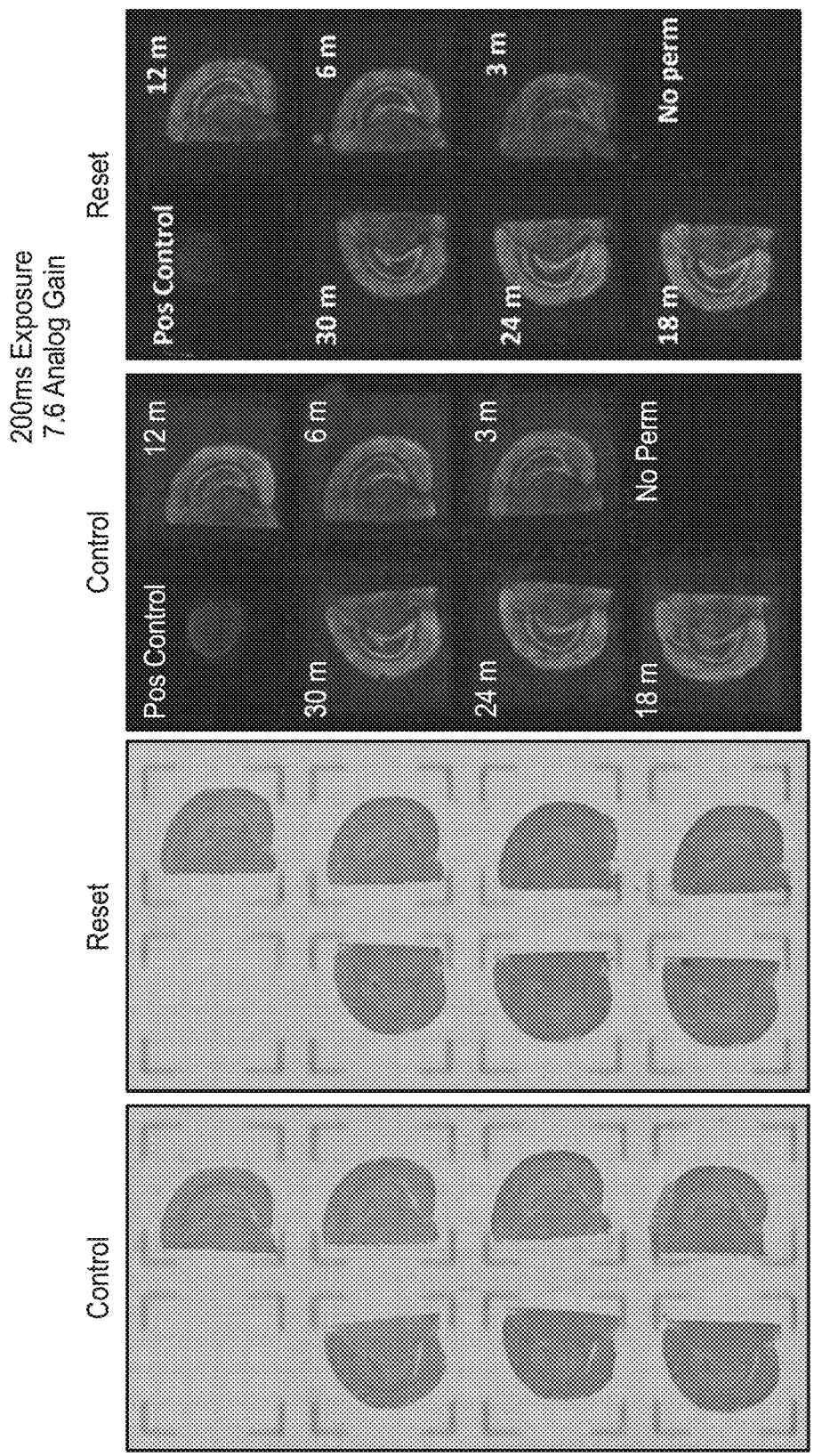
FIG. 13A-C show the effect of array reset using mouse brain samples using FIG. 13A) H&E staining, FIG. 13B) fluorescence imaging of cDNA reverse transcribed from captured analytes (time in minutes (m) is time of permeabilization), and FIG. 13C) the mean fluorescence intensity from FIG. 13B of a control versus reset array for different tissue permeabilization times.
Figure 13C:
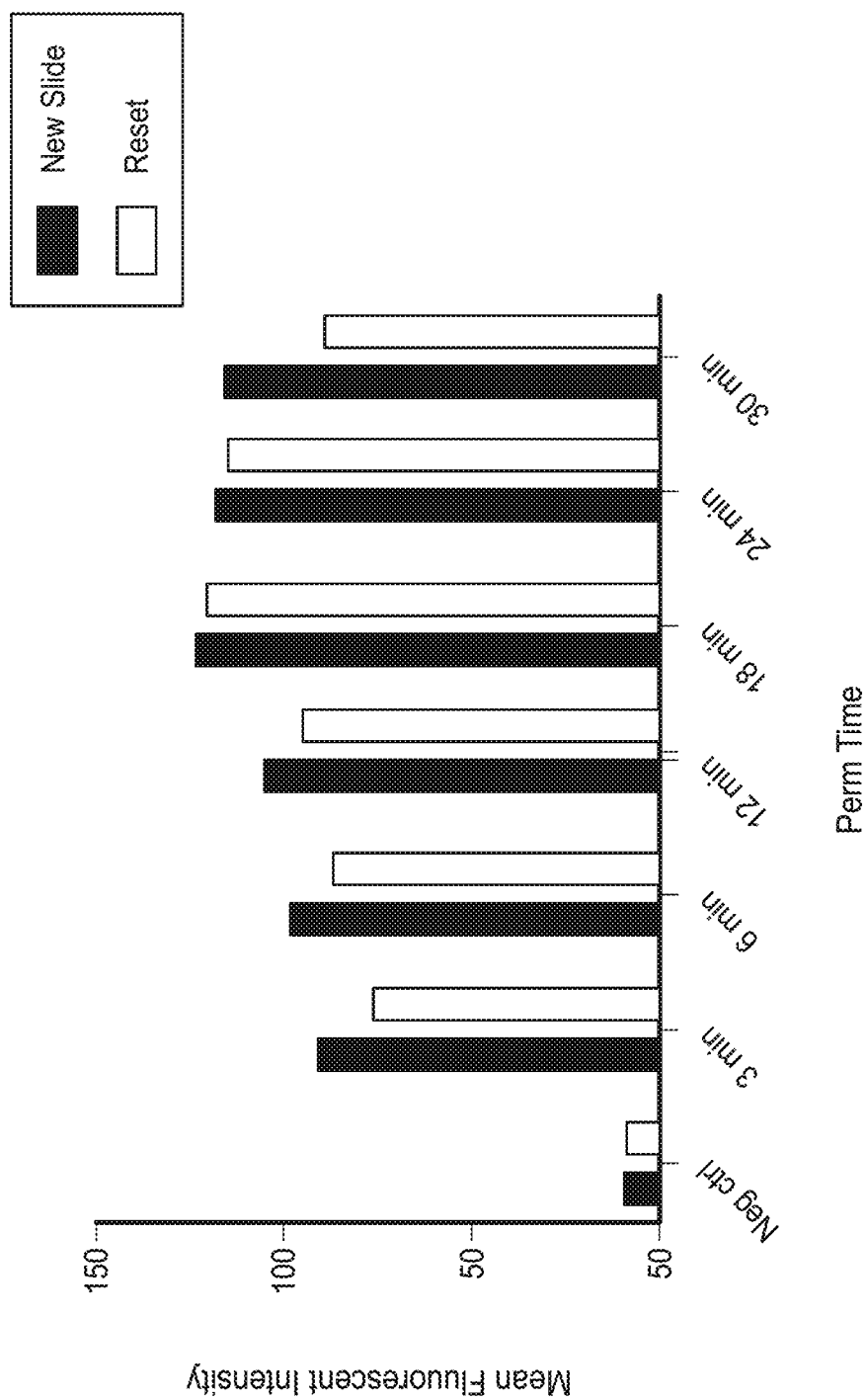
Figures 14A, 14B:
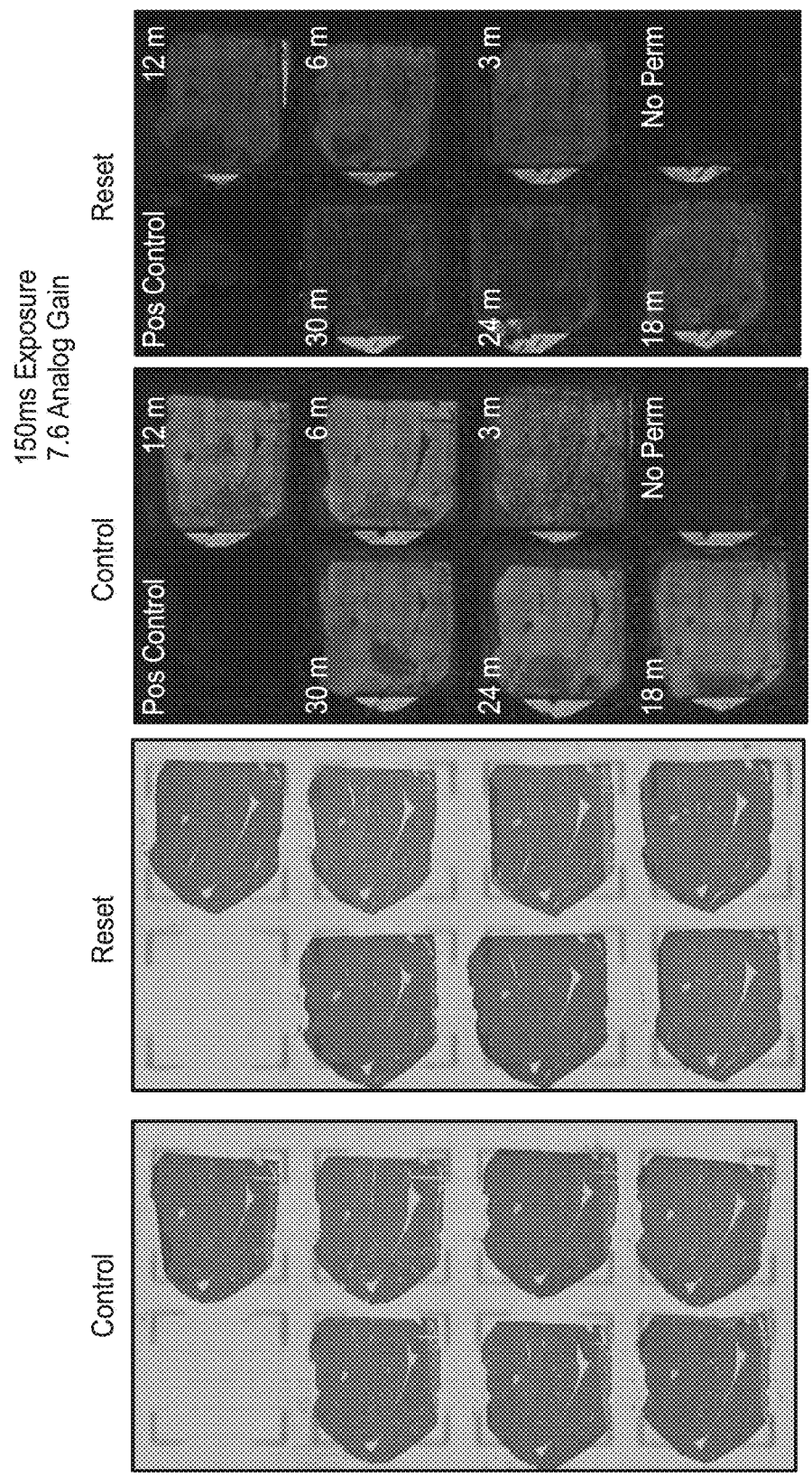
FIG. 14A-B show the effect of array reset using mouse liver samples using FIG. 14A) H&E staining and FIG. 14B) fluorescence imaging of cDNA reverse transcribed from captured analytes.
Figures 15A, 15B:
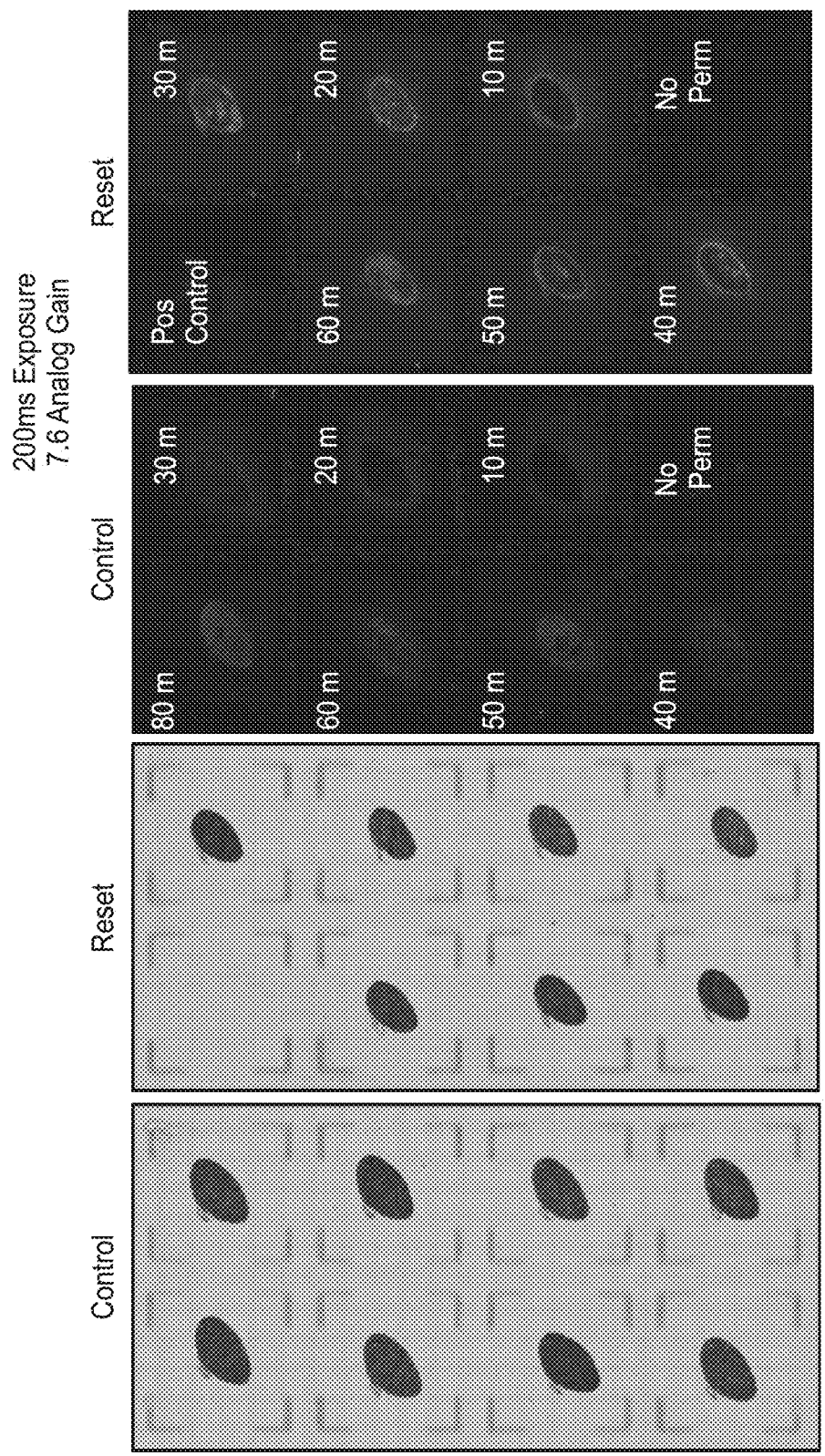
FIG. 15A-B show the effect of array reset using mouse spleen samples using FIG. 15A) H&E staining and FIG. 15B) fluorescence imaging of cDNA reverse transcribed from captured analytes.
Figure 17B:
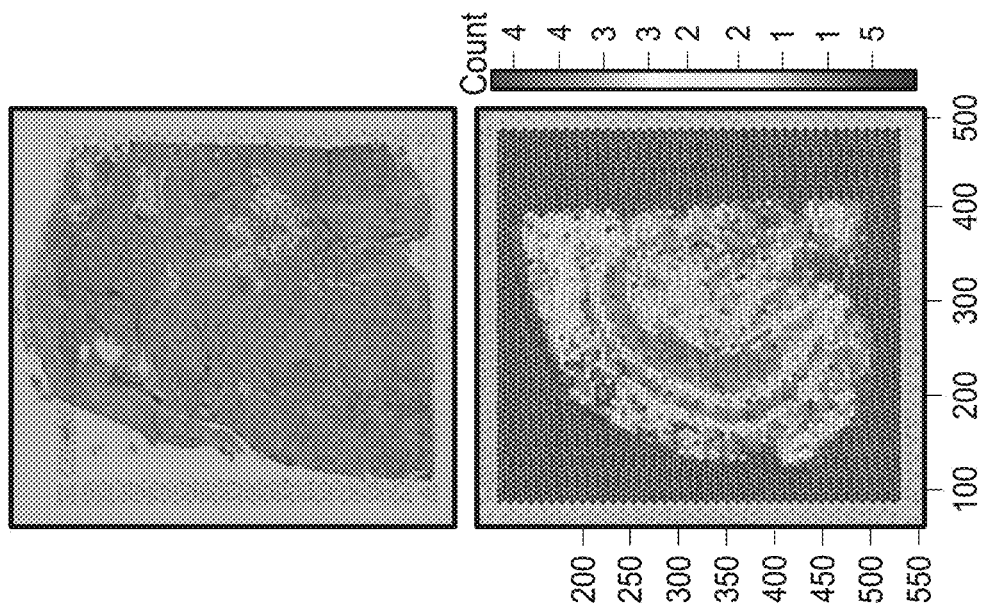
FIG. 17A-D show spatial gene analysis of mouse brain tissue on FIG. 17A) a new (control) array, and reset arrays that originally had FIG. 17B) human breast cancer tissue, FIG. 17C) human heart tissue, and FIG. 17D) human brain tissue, placed on them.
Figure 17A:
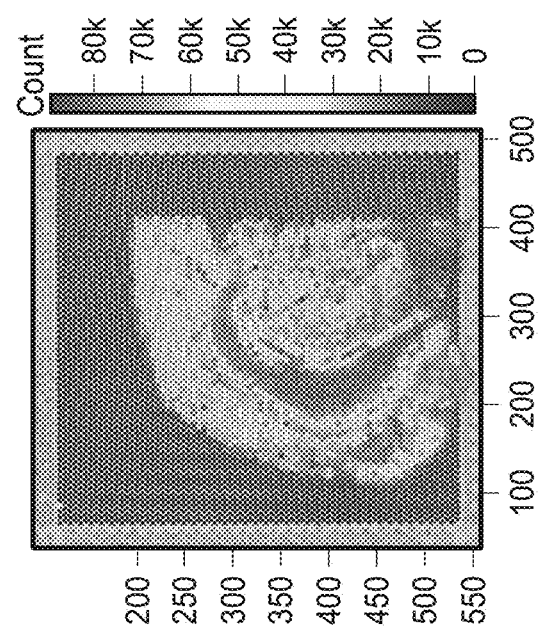
Figures 17C, 17D:
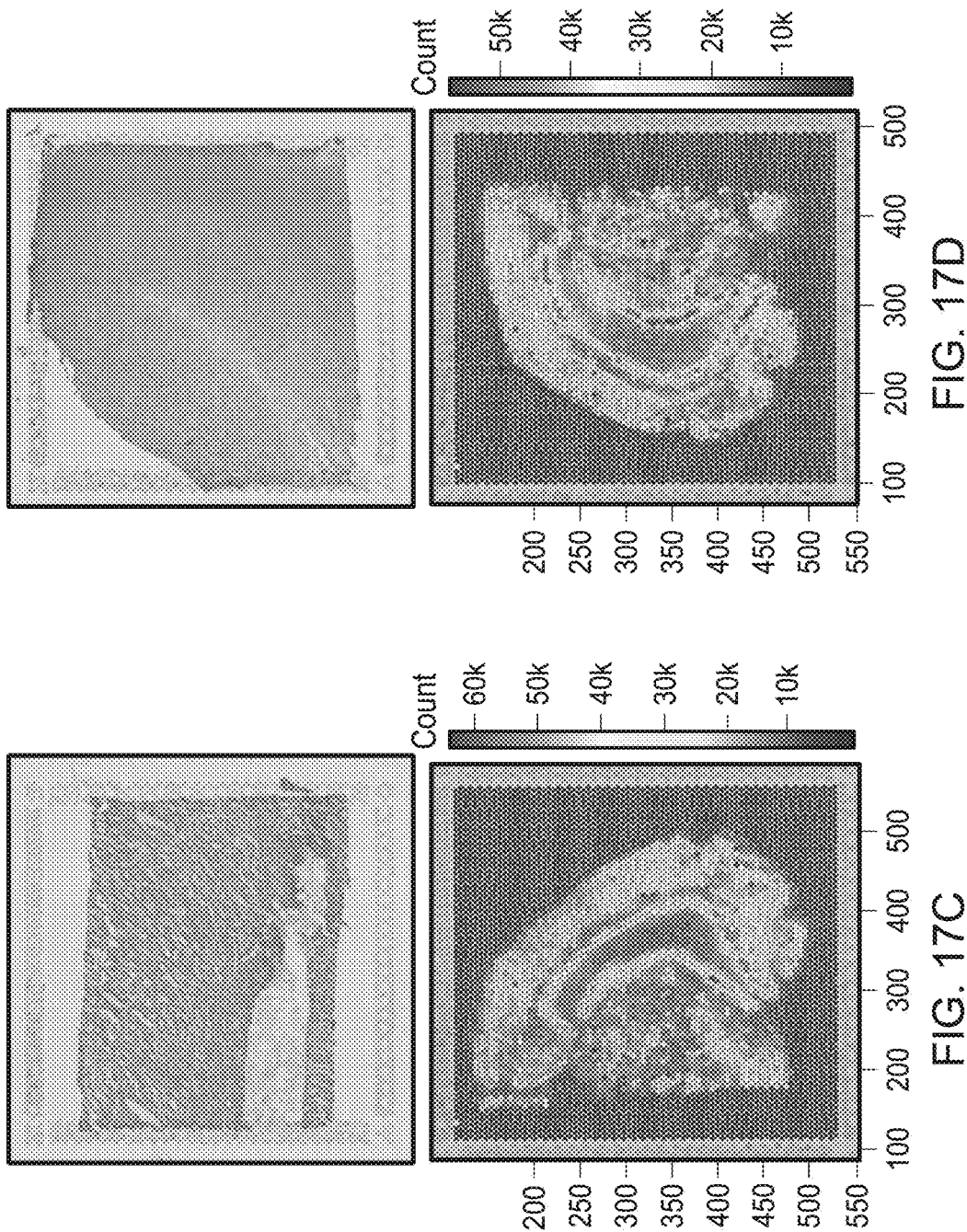

In FIG. 13A, the H&E stained mouse brain samples can be compared to the fluorescence images in FIG. 13B, and the mean fluorescence intensity is shown in FIG. 13C. In FIG. 14A, the H&E stained mouse liver samples can be compared to the fluorescence images in FIG. 14B. In FIG. 15A, the H&E stained mouse spleen samples can be compared to the fluorescence images in FIG. 15B. In each image, the control samples (on non-reset arrays) are shown on the left, while the samples on reset arrays are shown on the right. While some of the reset fluorescence appeared to be less than that of the control (FIG. 14B), or more than the control (FIG. 15B), no specific trend was observed in differences in transcript capture between the control samples and samples on reset arrays for the three tissue types.

Example 9— Array Reset with Different Tissue Types

Resetting arrays can be performed with multiple tissue types as the initial biological sample. To demonstrate this, different types of fixed and stained mouse or human tissues were originally placed on an array (upper figures in FIGS. 16B-E and 17B-D), and each array was reset according to Example 1. A new tissue sample was placed on each array, and the sample was analyzed using a spatial gene expression analysis (lower figures in FIGS. 16B-E and 17B-D). Control samples can be seen in FIG. 16A (human heart tissue) and 17A (mouse brain tissue) In FIG. 16A-E, the reset process is shown mouse eye as the original tissue sample (FIG. 16B), mouse small intestine as the original tissue sample (FIG. 16C), mouse testes as the original tissue sample (FIG. 16D), and mouse kidney as the original tissue sample (FIG. 16E), where human heart tissue was used as the tissue on the reset slides. In FIG. 17A-D, the reset process is shown for human breast cancer as the original tissue sample (FIG. 17B), human heart as the original tissue sample (FIG. 17C), and human brain as the original tissue sample (FIG. 17D), where mouse brain tissue was used as the tissue on the reset slides.

For those reset slides where mouse tissue was the original tissue, it was determined that the mouse tissues were removed completely or substantially completely wherein the gene expression of the control versus the reset slides was comparable. The same results were seen when the original tissue was of human origin. It was determined that multiple tissue types could be removed, slides reset, and new, different tissues applied to reset slides without compromising gene expression analysis.

What is claimed is:

1. A method for resetting an array, the method comprising:
    (a) applying an animal tissue section to an array, wherein the array comprises a plurality of capture probes, wherein a capture probe of the plurality of capture probes comprises a capture domain that binds to a nucleic acid from the animal tissue section; and
    (b) treating the array with a set of biological sample removal conditions, such that the animal tissue section is substantially removed from the array, wherein prior to said treating the array with the set of biological sample removal conditions, the animal tissue section applied on the array is permeabilized and no enzymatic extension reaction has been performed on the capture probes, and said treating the array with the set of biological sample removal conditions comprises treating the array with a base having a particular concentration, wherein the base is a base selected from potassium hydroxide, sodium hydroxide, and a combination thereof,
    thereby resetting the array.

2. The method of claim 1, wherein the array is a tissue optimization array or a spatial array.

3. The method of claim 1, wherein the nucleic acid is mRNA.

4. The method of claim 1, wherein the nucleic acid is DNA.

5. The method of claim 1, wherein said treating the array with the set of biological sample removal conditions further comprises washing the array one or more times.

6. The method of claim 5, wherein said treating the array with the set of biological sample removal conditions further comprises washing the array with a buffer one or more times.

7. The method of claim 6, wherein the buffer is selected from the group consisting of: Tris, phosphate buffered saline (PBS), HEPES (4-(2-hydroxyethyl)-1-piperazineethanesulfonic acid), TES (2-[(2-Hydroxy-1, 1-bis(hydroxymethyl)ethyl)amino]ethanesulfonic acid), and combinations thereof.

8. The method of claim 5, wherein said treating the array with the set of biological sample removal conditions further comprises drying the array.

9. The method of claim 5, wherein said treating the array with the set of biological sample removal conditions comprises, sequentially, treating the array with a proteinase, washing the array with water, treating the array with the base, washing the array with a buffer, and washing the array with water, and optionally, drying the array.

10. The method of claim 9, wherein the proteinase is proteinase K.

11. The method of claim 5, wherein the method further comprises, between step (a) and step (b), a step of identifying whether the animal tissue section has been applied to the array incorrectly or does not contain a region of interest.

12. The method of claim 11, wherein said identifying whether the animal tissue section has been applied to the array incorrectly or does not contain a region of interest comprises: identifying whether one or more fiducial markers on the array is obscured by the animal tissue section, identifying whether the animal tissue section is folded, identifying whether the animal tissue section is torn or damaged, identifying whether the animal tissue section overlaps with a different animal tissue section if a plurality animal tissue sections is applied to the array, imaging the animal tissue section after staining or immunofluorescence staining the array, or a combination thereof.

13. The method of claim 5, wherein the array is a spatial array and the method further comprises after step (b):
    (c) contacting the spatial array with a different animal tissue section.

14. The method of claim 5, wherein the array is a tissue optimization array and the method further comprises after step (b):
    (c) contacting the tissue optimization array with a different animal tissue section.

15. A method for resetting an array to which an animal tissue section has been applied, the method comprising:
    treating the array with a set of biological sample removal conditions, such that the animal tissue section is substantially removed from the array, wherein the array comprises a plurality of capture probes, wherein a capture probe of the plurality of capture probes comprises a capture domain that binds specifically to a nucleic acid from the animal tissue section, and wherein prior to said treating the array with the set of biological sample removal conditions, the animal tissue section applied on the array is permeabilized and no enzymatic extension reaction has been performed on the capture probes, and said treating the array with the set of biological sample removal conditions comprises treating the array with a base having a particular concentration, wherein the base is a base selected from potassium hydroxide, sodium hydroxide, and a combination thereof, thereby resetting the array.

16. The method of claim 15, wherein the array is a tissue optimization array or a spatial array.

17. The method of claim 15, wherein the nucleic acid is mRNA.

18. The method of claim 15, wherein the nucleic acid is DNA.

19. The method of claim 15, wherein said treating the array with the set of biological sample removal conditions further comprises washing the array one or more times.

20. The method of claim 15, wherein said treating the array with the set of biological sample removal conditions further comprises washing the array with a buffer one or more times.

21. The method of claim 20, wherein the buffer is selected from the group consisting of: Tris, phosphate buffered saline (PBS), HEPES (4-(2-hydroxyethyl)-1-piperazineethanesulfonic acid), TES (2-[(2-Hydroxy-1, 1-bis(hydroxymethyl)ethyl)amino]ethanesulfonic acid), and combinations thereof.

22. The method of claim 15, wherein said treating the array with the set of biological sample removal conditions further comprises drying the array.

23. The method of claim 15, wherein said treating the array with the set of biological sample removal conditions comprises, sequentially, treating the array with a proteinase, washing the array with water, treating the array with the base, washing the array with a buffer, and washing the array with water, and optionally, drying the array.

24. The method of claim 23, wherein the proteinase is proteinase K.

25. The method of claim 15, wherein the method further comprises, between step (a) and step (b), a step of identifying whether the animal tissue section has been applied to the array incorrectly or does not contain a region of interest.

26. The method of claim 25, wherein said identifying whether the animal tissue section has been applied to the array incorrectly or does not contain a region of interest comprises: identifying whether one or more fiducial markers on the array is obscured by the animal tissue section, identifying whether the animal tissue section is folded, identifying whether the animal tissue section is torn or damaged, identifying whether the animal tissue section overlaps with a different animal tissue section if the different animal tissue section is also applied to the array, imaging the animal tissue section after staining or immunofluorescence staining the array, or a combination thereof.

27. The method of claim 15, wherein the array is a spatial array and the method further comprises after said treating the array with a set of biological sample removal conditions:

contacting the spatial array with a different animal tissue section.

28. The method of claim 15, wherein the array is a tissue optimization array and the method further comprises after said treating the array with a set of biological sample removal conditions:

contacting the tissue optimization array with a different animal tissue section.

* * * * *

UNITED STATES PATENT AND TRADEMARK OFFICE
CERTIFICATE OF CORRECTION

PATENT NO. : 11,560,592 B2
APPLICATION NO. : 17/548047
DATED : January 24, 2023
INVENTOR(S) : Jennifer Chew, Zachary Bent and Alvaro J Gonzalez Lozano It is certified that error appears in the above-identified patent and that said Letters Patent is hereby corrected as shown below:

In the Claims

Column 32, Approximately Line 15, in Claim 6, delete "5," and insert -- 1, --.

Column 32, Line 25, in Claim 8, delete "5," and insert -- 1, --.

Column 32, Approximately Line 28, in Claim 9, delete "5," and insert -- 1, --.

Column 32, Approximately Line 37, in Claim 11, delete "5," and insert -- 1, --.

Column 32, Line 49, in Claim 12, after "plurality" insert -- of --.

Column 32, Line 53, in Claim 13, delete "5," and insert -- 1, --.

Column 32, Line 57, in Claim 14, delete "5," and insert -- 1, --.

Signed and Sealed this
Twenty-eighth Day of March, 2023

Katherine Kelly Vidal
*Director of the United States Patent and Trademark Office*